(12) United States Patent
Harding et al.

(10) Patent No.: US 9,079,953 B2
(45) Date of Patent: Jul. 14, 2015

(54) ANTI-VEGF ANTIBODIES AND THEIR USES

(75) Inventors: Fiona A. Harding, Santa Clara, CA (US); Yoshiko Akamatsu, Palo Alto, CA (US); Robert B. DuBridge, Belmont, CA (US); David B. Powers, Fairfax, CA (US)

(73) Assignee: AbbVie Biotherapeutics Inc., Redwood City, CA (US)

( * ) Notice: Subject to any disclaimer, the term of this patent is extended or adjusted under 35 U.S.C. 154(b) by 379 days.

(21) Appl. No.: 12/817,800

(22) Filed: Jun. 17, 2010

(65) Prior Publication Data

US 2010/0322931 A1    Dec. 23, 2010

Related U.S. Application Data

(60) Provisional application No. 61/218,005, filed on Jun. 17, 2009.

(51) Int. Cl.
C07K 16/22     (2006.01)
A61K 39/395    (2006.01)

(52) U.S. Cl.
CPC ............. *C07K 16/22* (2013.01); *C07K 2317/24* (2013.01); *C07K 2317/565* (2013.01); *C07K 2317/92* (2013.01)

(58) Field of Classification Search
CPC ............... C07K 16/22; C07K 2317/92; C07K 2317/565; C07K 2317/24; A61K 47/48376
See application file for complete search history.

(56) References Cited

U.S. PATENT DOCUMENTS

| | | |
|---|---|---|
| 6,632,926 B1 | 10/2003 | Chen et al. |
| 6,828,121 B2 | 12/2004 | Chen |
| 6,884,879 B1 | 4/2005 | Baca et al. |
| 6,979,559 B2 | 12/2005 | Harris, Jr. et al. |
| 7,117,096 B2 | 10/2006 | Luo et al. |
| 7,820,165 B2 | 10/2010 | McKenna et al. |
| 8,314,213 B2 | 11/2012 | Bernett et al. |
| 2002/0032315 A1 | 3/2002 | Baca et al. |
| 2002/0177170 A1 | 11/2002 | Luo et al. |
| 2003/0022240 A1 | 1/2003 | Luo et al. |
| 2003/0224397 A1 | 12/2003 | Lowman et al. |
| 2004/0010376 A1 | 1/2004 | Luo et al. |
| 2004/0133357 A1 | 7/2004 | Zhong et al. |
| 2004/0229310 A1 | 11/2004 | Simmons |
| 2005/0038231 A1 | 2/2005 | Fahrner et al. |
| 2005/0053599 A1 | 3/2005 | Van Bruggen et al. |
| 2005/0170464 A1 | 8/2005 | Simmons et al. |
| 2006/0067930 A1 | 3/2006 | Adams et al. |
| 2006/0088523 A1 | 4/2006 | Andya et al. |
| 2006/0182783 A1 | 8/2006 | Hughes et al. |
| 2007/0037214 A1 | 2/2007 | Luo et al. |
| 2007/0037217 A1 | 2/2007 | Luo et al. |
| 2007/0059336 A1 | 3/2007 | Hughes et al. |
| 2007/0128111 A1 | 6/2007 | Reilly et al. |
| 2007/0196374 A1 | 8/2007 | Baca et al. |
| 2007/0248610 A1 | 10/2007 | Baca et al. |
| 2008/0015194 A1 | 1/2008 | Errico et al. |
| 2008/0166351 A1 | 7/2008 | Fyfe et al. |
| 2008/0187186 A1 | 8/2008 | Baca et al. |
| 2008/0207467 A1 | 8/2008 | Moore et al. |
| 2008/0226629 A1 | 9/2008 | Baca et al. |
| 2008/0268051 A1 | 10/2008 | Hughes et al. |
| 2008/0292628 A1 | 11/2008 | Hui |
| 2008/0299115 A1 | 12/2008 | Lowman et al. |
| 2009/0053786 A1 | 2/2009 | Kao et al. |
| 2009/0311251 A1 | 12/2009 | Auf Der Maur et al. |
| 2009/0318297 A1 | 12/2009 | Cappucilli et al. |

FOREIGN PATENT DOCUMENTS

| | | |
|---|---|---|
| EP | 1695985 | 8/2006 |
| EP | 1950300 | 7/2008 |
| WO | WO 02/48376 | 6/2002 |
| WO | WO 02/061090 | 8/2002 |
| WO | WO 00/29584 | 9/2002 |
| WO | WO 03/068801 | 8/2003 |
| WO | WO 03/099999 | 12/2003 |
| WO | WO 2004/042017 | 5/2004 |
| WO | WO 2005/016968 | 2/2005 |
| WO | WO 2006/043972 | 4/2006 |
| WO | WO 2007/059336 | 5/2007 |

OTHER PUBLICATIONS

Skolnick and Fetrow. From genes to protein structure and function: novel applications of computational approaches in the genomic era. Trends in Biotechnology, 2000. vol. 18, pp. 34-39.*
Mac Callum, Martin, and Thornton. Antibody antigen interactions: contact analysis and binding site topography. Journal of Molecular Biology, 1996. vol. 262, pp. 732-745.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Vajdos, Adams, Breece, Presta, De Vos, and Sidhu. Comprehensive functional maps of the antigen binding site of an anti-ErbB2 antibody obtained with shotgun scanning mutagenesis. Journal of Molecular Biology, 2002. vol. 320, pp. 415-428.*
Wu, Nie, Huse, and Watkins. Humanization of a murine monoclonal antibody by simultaneous optimization of framework and CDR residues. Journal of Molecular Biology, 1999. vol. 294, pp. 151-162.*
Sathish et al., Nature Reviews 12: 306-324, Apr. 2013.*
Rudikoff et al., Proc. Natl. Acad. Sci. USA, 79(6): 1979-1983.*
Winkler et al., J Immunology 165: 4505-4514, 2000.*
Aiello et al., "Vascular endothelial growth factor in ocular fluid of patients with diabetic retinopathy and other retinal disorders," N. Engl. J. Med., 331, 1480 (1994).
Baca et al., "Antibody humanization using monovalent phage display," J. Biol. Chem., 272, 10678-10684 (1997).
Berkman et al., "Expression of the vascular permeability factor/vascular endothelial growth factor gene in central nervous system neoplasms," J. Clin. Invest., 91, 153 (1993).
Blowers & Hall, "Managing adverse events in the use of bevacizumab and chemotherapy," Br. J. Nurs., 18, 351 (2009).
Chen et al., "Selection and Analysis of an Optimized Anti-VEGF Antibody: Crystal Structure of an Affinity-matured Fab in Complex with Antigen," J. Mol. Biol., 293, 865-881 (1999).

(Continued)

*Primary Examiner* — Phuong Huynh
(74) *Attorney, Agent, or Firm* — Dechert LLP

(57) ABSTRACT

The present disclosure relates to antibodies directed to vascular endothelial growth factor ("VEGF") and uses of such antibodies, for example to treat diseases associated with the activity and/or overproduction of VEGF.

11 Claims, 39 Drawing Sheets

(56) References Cited

OTHER PUBLICATIONS

Dvorak et al., "Vascular permeability factor/vascular endothelial growth factor, microvascular hyperpermeability, and angiogenesis," Am. J. Pathol., 146, 1029 (1995).

Ferrara et al., "The biology of VEGF and its receptors," Nature Medicine, 9, 669 (2003).

Folkman et al., "Angiogenesis," J. Biol. Chem., 267, 10931 (1992).

Lien et al., "In: Chernajovsky, 2008, Therapeutic Antibodies," Handbook of Experimental Pharmacology, 181, 131-150 (2008).

Lopez et al., "Transdifferentiated retinal pigment epithelial cells are immunoreactive for vascular endothelial growth factor in surgically excised age-related macular degeneration-related choroidal neovascular membranes," Invest. Ophtalmo.Vis. Sci., 37, 855 (1996).

Muller et al., "VEGF and the Fab fragment of a humanized neutralizing antibody: crystal structure of the complex at 2.4 Å resolution and mutational analysis of the interface," Structure, 6, 1153-1167 (1998).

Partial International Search Report mailed Sep. 6, 2010 corresponding to related International Patent Application No. PCT/2010/039029.

Presta et al., "Humanization of an anti-vascular endothelial growth factor monoclonal antibody for the therapy of solid tumors and other disorders," Cancer Res., 57, 4593 (1997).

Ferrara et al., May 2004 "Discovery and Development of Bevacizumab, an Anti-VEGF Antibody for Treating Cancer," *Nature Reviews* 3:391-400.

Lee et al., 2004, "High-affinity Human Antibodies from Phage-displayed Synthetic Fab Libraries with a Single Framework Scaffold," *J. Mol. Biol.* 340:1073-1093.

Search Report and Written Opinion mailed Feb. 28, 2013 from Singapore patent application No. 201109347-3.

Ferrara et al., "Heterozygous embryonic lethality by targeted inactivation of the VEGF gene," Nature, 380, 439 (1996).

International Search Report and Written Opinion mailed Jan. 5, 2011 corresponding to related International Patent Application No. PCT/US2010/039029.

Correspondence from Castillo Grau & Associates regarding oppositions filed against Colombian counterpart of U.S. Appl. No. 12/817,800, Colombian Application No. 11179622 dated Feb. 12, 2013.

EPO Communication pursuant to Article 94(3) EPC from EP 10725590.3 (European application corresponding to PCT/US10/039029) dated Oct. 10, 2012.

Opposition lodged by Asociación Industrial de Laboratorios Farmacéuticos AG against Chilean counterpart of U.S. Appl. No. 12/817,800, Chilean Application No. 3182-2011.

* cited by examiner

Bevacizumab (Avastin®) VH (SEQ ID NO:1)

EVQLVESGGGLVQPGGSLRLSCAASGYTFTNYGMNWVRQAPGKGLEWVG**WINTYTGEPT
YAADFKRRFTFSLDTSKSTAYLQMNSLRAEDTAVYYCAKYPHYYGSSHWYFDV**WGQGTL
VTVSS

Bevacizumab (Avastin®) VL (SEQ ID NO:2)

DIQMTQSPSSLSASVGDRVTITCSASQDISNYLNWYQQKPGKAPKVLIYFTSSLHSGVP
SRFSGSGSGTDFTLTISSLQPEDFATYYCQQYSTVPWTFGQGTKVEIKR

FIGURE 1A

| Antibody Chain | CDR No. | Sequence | SEQ ID NO. |
|---|---|---|---|
| Heavy | 1 | GYTFTNYGMN | 3 |
| Heavy | 2 | WINTYTGEPTYAADFKR | 4 |
| Heavy | 3 | YPHYYGSSHWYFDV | 5 |
| Light | 1 | SASQDISNYLN | 6 |
| Light | 2 | FTSSLHS | 7 |
| Light | 3 | QQYSTVPWT | 8 |

FIGURE 1B

Ranibizumab (Lucentis®) VH (SEQ ID NO:9)

EVQLVESGGGLVQPGGSLRLSCAASGYDFTHYGMNWVRQAPGKGLEWVG**WINTYTGEPT
YAADFKRRFTFSLDTSKSTAYLQMNSLRAEDTAVYYCAKYPYYYGTSHWYFDV**WGQGTL
VTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKKVEPKSCDKTHL

Ranibizumab (Lucentis®) VL (SEQ ID NO:10)

DIQLTQSPSSLSASVGDRVTITCSASQDISNYLNWYQQKPGKAPKVLIYFTSSLHSGVP
SRFSGSGSGTDFTLTISSLQPEDFATYYCQQYSTVPWTFGQGTKVEIKRTVAAPSVFIF
PPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC

FIGURE 1C

| Antibody Chain | CDR No. | Sequence | SEQ ID NO. |
|---|---|---|---|
| Heavy | 1 | GYDFTHYGMN | 11 |
| Heavy | 2 | WINTYTGEPTYAADFKR | 4 |
| Heavy | 3 | YPYYYGTSHWYFDV | 12 |
| Light | 1 | SASQDISNYLN | 6 |
| Light | 2 | FTSSLHS | 7 |
| Light | 3 | QQYSTVPWT | 8 |

FIGURE 1D

| Antibody Chain | CDR No. | Residue | Position in CDR | Kabat No. |
|---|---|---|---|---|
| Heavy | 1 | G | 1 | 26 |
| | | Y | 2 | 27 |
| | | T | 3 | 28 |
| | | F | 4 | 29 |
| | | T | 5 | 30 |
| | | N | 6 | 31 |
| | | Y | 7 | 32 |
| | | G | 8 | 33 |
| | | M | 9 | 34 |
| | | N | 10 | 35 |
| Heavy | 2 | W | 1 | 50 |
| | | I | 2 | 51 |
| | | N | 3 | 52 |
| | | T | 4 | 52a |
| | | Y | 5 | 53 |
| | | T | 6 | 54 |
| | | G | 7 | 55 |
| | | E | 8 | 56 |
| | | P | 9 | 57 |
| | | T | 10 | 58 |
| | | Y | 11 | 59 |
| | | A | 12 | 60 |
| | | A | 13 | 61 |
| | | D | 14 | 62 |
| | | F | 15 | 63 |
| | | K | 16 | 64 |
| | | R | 17 | 65 |
| Heavy | 3 | Y | 1 | 95 |
| | | P | 2 | 96 |
| | | H | 3 | 97 |
| | | Y | 4 | 98 |
| | | Y | 5 | 99 |
| | | G | 6 | 100 |
| | | S | 7 | 100a |
| | | S | 8 | 100b |
| | | H | 9 | 100c |
| | | W | 10 | 100d |
| | | Y | 11 | 100e |
| | | F | 12 | 100f |
| | | D | 13 | 101 |
| | | V | 14 | 102 |

FIGURE 5

| Antibody Chain | CDR No. | Residue | Position in CDR | Kabat No. |
|---|---|---|---|---|
| Light | 1 | S | 1 | 24 |
| | | A | 2 | 25 |
| | | S | 3 | 26 |
| | | Q | 4 | 27 |
| | | D | 5 | 28 |
| | | I | 6 | 29 |
| | | S | 7 | 30 |
| | | N | 8 | 31 |
| | | Y | 9 | 32 |
| | | L | 10 | 33 |
| | | N | 11 | 34 |
| Light | 2 | F | 1 | 50 |
| | | T | 2 | 51 |
| | | S | 3 | 52 |
| | | S | 4 | 53 |
| | | L | 5 | 54 |
| | | H | 6 | 55 |
| | | S | 7 | 56 |
| Light | 3 | Q | 1 | 89 |
| | | Q | 2 | 90 |
| | | Y | 3 | 91 |
| | | S | 4 | 92 |
| | | T | 5 | 93 |
| | | V | 6 | 94 |
| | | P | 7 | 95 |
| | | W | 8 | 96 |
| | | T | 9 | 97 |

FIGURE 6

| SEQ ID NO: | VL Peptide |
|---|---|
| 13. | DIQMTQSPSSLSASV |
| 14. | MTQSPSSLSASVGDR |
| 15. | SPSSLSASVGDRVTI |
| 16. | SLSASVGDRVTITCS |
| 17. | ASVGDRVTITCSASQ |
| 18. | GDRVTITCSASQDIS |
| 19. | VTITCSASQDISNYL |
| 20. | TCSASQDISNYLNWY |
| 21. | ASQDISNYLNWYQQK |
| 22. | DISNYLNWYQQKPGK |
| 23. | NYLNWYQQKPGKAPK |
| 24. | NWYQQKPGKAPKVLI |
| 25. | QQKPGKAPKVLIYFT |
| 26. | PGKAPKVLIYFTSSL |
| 27. | APKVLIYFTSSLHSG |
| 28. | VLIYFTSSLHSGVPS |
| 29. | YFTSSLHSGVPSRFS |
| 30. | SSLHSGVPSRFSGSG |
| 31. | HSGVPSRFSGSGSGT |
| 32. | VPSRFSGSGSGTDFT |
| 33. | RFSGSGSGTDFTLTI |
| 34. | GSGSGTDFTLTISSL |
| 35. | SGTDFTLTISSLQPE |
| 36. | DFTLTISSLQPEDFA |
| 37. | LTISSLQPEDFATYY |
| 38. | SSLQPEDFATYYCQQ |
| 39. | QPEDFATYYCQQYST |
| 40. | DFATYYCQQYSTVPW |
| 41. | TYYCQQYSTVPWTFG |
| 42. | CQQYSTVPWTFGQGT |
| 43. | YSTVPWTFGQGTKVE |
| 44. | VPWTFGQGTKVEIKR |

FIGURE 7

| SEQ ID NO: | VH Peptide |
|---|---|
| 45. | EVQLVESGGGLVQPG |
| 46. | LVESGGGLVQPGGSL |
| 47. | SGGGLVQPGGSLRLS |
| 48. | GLVQPGGSLRLSCAA |
| 49. | QPGGSLRLSCAASGY |
| 50. | GSLRLSCAASGYTFT |
| 51. | RLSCAASGYTFTNYG |
| 52. | CAASGYTFTNYGMNW |
| 53. | SGYTFTNYGMNWVRQ |
| 54. | TFTNYGMNWVRQAPG |
| 55. | NYGMNWVRQAPGKGL |
| 56. | MNWVRQAPGKGLEWV |
| 57. | VRQAPGKGLEWVGWI |
| 58. | APGKGLEWVGWINTY |
| 59. | KGLEWVGWINTYTGE |
| 60. | EWVGWINTYTGEPTY |
| 61. | GWINTYTGEPTYAAD |
| 62. | NTYTGEPTYAADFKR |
| 63. | TGEPTYAADFKRRFT |
| 64. | PTYAADFKRRFTFSL |
| 65. | AADFKRRFTFSLDTS |
| 66. | FKRRFTFSLDTSKST |
| 67. | RFTFSLDTSKSTAYL |
| 68. | FSLDTSKSTAYLQMN |
| 69. | DTSKSTAYLQMNSLR |
| 70. | KSTAYLQMNSLRAED |
| 71. | AYLQMNSLRAEDTAV |
| 72. | QMNSLRAEDTAVYYC |
| 73. | SLRAEDTAVYYCAKY |
| 74. | AEDTAVYYCAKYPHY |
| 75. | TAVYYCAKYPHYYGS |
| 76. | YYCAKYPHYYGSSHW |
| 77. | AKYPHYYGSSHWYFD |
| 78. | PHYYGSSHWYFDVWG |
| 79. | YGSSHWYFDVWGQGT |
| 80. | SHWYFDVWGQGTLVT |
| 81. | YFDVWGQGTLVTVSS |

FIGURE 8

| SEQ ID. NO. | Sequence | n | % | SI | s.e.m. |
|---|---|---|---|---|---|
| 25 | QQKPGKAPKVLIY<u>FT</u> | 15 | 15.15 | 1.82 | 0.24 |
| 62 | NTYTGEPTYAADFKR | 16 | 16.16 | 2.16 | 0.35 |
| 74 | AEDTAVYYCAK<u>YPHY</u> | 9 | 9.09 | 1.45 | 0.18 |

FIGURE 9

| WT | position | Candidate deimmunizing substitutions |
|---|---|---|
| CDR-H2 | | |
| A | 61 | F, E, D |
| D | 62 | G, L, Q, T, K, R, E, H |
| K | 64 | S, V, Q |
| R | 65 | V, F, H, N, S, Q, K, I |
| CDR-H3 | | |
| Y | 98 | H |

FIGURE 10

| SEQ ID NO: | 28 | 31 | 97 | 99 | 100a | $k_{on}$ (1/Ms) | $k_{off}$ (1/s) | $K_D$ (M) | Δ $k_{on}$ | Δ $k_{off}$ | Δ $K_D$ |
|---|---|---|---|---|---|---|---|---|---|---|---|
| 82 |  | F | D | D | G | 2.08E+06 | 1.72E-04 | 8.27E-11 | 11.6 | 2.0 | 23.8 |
| 83 |  | F | P | D | G | 1.88E+06 | 1.94E-04 | 1.06E-10 | 10.4 | 1.8 | 18.6 |
| 84 |  | F | P | E |  | 1.60E+06 | 1.82E-04 | 1.28E-10 | 8.9 | 1.9 | 15.3 |
| 85 |  | F | E | E |  | 1.25E+06 | 1.75E-04 | 1.40E-10 | 6.9 | 2.0 | 14.1 |
| 86 |  | F | D | E |  | 1.33E+06 | 2.38E-04 | 1.79E-10 | 7.4 | 1.5 | 11.0 |
| 87 |  | F | E | D | G | 8.24E+05 | 1.60E-04 | 2.04E-10 | 4.6 | 2.2 | 9.6 |
| 88 |  | F |  | D | G | 9.68E+05 | 2.73E-04 | 2.82E-10 | 5.4 | 1.3 | 7.0 |
| 89 |  | F | P | D |  | 9.04E+05 | 2.49E-04 | 2.82E-10 | 5.0 | 1.4 | 7.0 |
| 90 |  | F | D |  | G | 6.45E+05 | 1.97E-04 | 3.11E-10 | 3.6 | 1.8 | 6.3 |
| 91 |  | F |  |  |  | 2.11E+05 | 1.21E-04 | 5.75E-10 | 1.2 | 2.9 | 3.4 |
| 92 |  |  | P |  |  | 3.67E+05 | 2.56E-04 | 7.08E-10 | 2.0 | 1.4 | 2.8 |
| 93 |  |  | E |  |  | 2.92E+05 | 2.25E-04 | 7.61E-10 | 1.6 | 1.6 | 2.6 |
| 94 |  | F |  |  | G | 2.58E+05 | 2.20E-04 | 8.57E-10 | 1.4 | 1.6 | 2.3 |
| 95 |  |  | D |  |  | 2.62E+05 | 3.96E-04 | 1.54E-09 | 1.5 | 0.9 | 1.3 |
| 96 |  | F | P |  | G | 2.25E+05 | 3.79E-04 | 1.75E-09 | 1.3 | 0.9 | 1.1 |
| WT | T | N | H | Y | S | 1.80E+05 | 3.52E-04 | 1.97E-09 | 1.0 | 1.0 | 1.0 |

FIGURE 11

| WT | Position | Increased affinity heavy chain substitutions |
|---|---|---|
| | | CDR-H1 |
| T | 28 | P |
| N | 31 | F, G, M |
| | | CDR-H3 |
| H | 97 | A, D, E, P, Q, S, T |
| Y | 99 | D, E |
| S | 100a | D, E, G, V |

FIGURE 12

| WT | Position | Increased affinity heavy chain substitutions |
|---|---|---|
| | | CDR-H1 |
| T | 30 | W, R, Q |
| | | CDR-H2 |
| Y | 53 | F |
| T | 58 | F |
| A | 61 | G, K, R, H, Y |
| K | 64 | G, E |
| R | 65 | L, T, A, E, D |
| | | CDR-H3 |
| Y | 98 | F |
| Y | 100e | F |

FIGURE 13

| WT | Position | Neutral heavy chain substitutions |
|---|---|---|
| | | CDR-H1 |
| T | 30 | I, M, V |
| N | 31 | Y, S, A, Q |
| | | CDR-H2 |
| A | 61 | F, E, D |
| D | 62 | G, L, Q, T, K, R, E, H |
| K | 64 | S, V, Q |
| R | 65 | V, F, H, N, S, Q, K, I |
| | | CDR-H3 |
| Y | 98 | H |

FIGURE 14

| WT | Position | Neutral light chain substitutions |
|---|---|---|
| | | CDR-L1 |
| S | 24 | R, W, G |
| S | 26 | V |
| S | 30 | G |
| N | 31 | L, S |
| | | CDR-L2 |
| L | 54 | M |
| H | 55 | R |
| S | 56 | G, R |
| | | CDR-L3 |
| T | 93 | D, E, S |

| V# | CDR-H1 | | | | | | | | | | CDR-H2 | | | | | | | | | | | | | | | | CDR-H3 | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|
| | G | Y | T | F | T | N | Y | G | M | W | I | N | T | Y | T | G | E | P | T | Y | A | A | D | F | K | R | Y | P | H | Y | Y | G | S | G | S | H | W | Y | F | D | V |
| 29 | | | | | | | | | | | | | | | | | | | | | | | | | | | | | | | | | | | | | | | | | L |
| 30 | | | | | | | | | | | | | | | | | | | | | | | | | | | | | | | | | | | | | | | | | |
| 31 | | | | | | | | | | | | | | | | | | | | | | | | | | | | | | | | | | | | Q | | | | | |
| 32 | | | | | | | | | | | | | | | | | | | | | | | | | | | | | | | | | R | | | | | | | | |
| 33 | | | | | | | | | | | | | | | | | | | | | | | | | | | D | | | | | | G | | C | | | | | | |
| 34 | | | | | | | | | | | | | | | | | | | | | | | | | | | | | | | | | T | | T | | | | | | |
| 35 | | | | | | | | | | | | | | | | | | | | | | | | | | | | | | | | | A | | Y | | | | | | |
| 36 | | | | | | | | | | | | | | | | | | | | | | | | | | | R | | | | | | A | | Y | | | | | | |
| 37 | | | | | | | | | | | | | | | | | | | | | | | | | | | | | | | YS | GER | ES | | | | | | | | |
| 38 | | | | | | | | | | | | | | | | | | | | | | | | | | | | | | | YA | REG | G | | | | | | | | |
| 39 | | | | | | | | | | | | | | | | | | | | | | | | | | | | | | | YS | VEG | G | | | | | | | | |
| 40 | | | | | | | | | | | | | | | | | | | | | | | | | | | | | | | | G | G | | | | | | | | |
| 41 | | | | | | | | | | | | | | | | | | | | | | | | | | | | | | | YH | QSE | GR | | | | | | | | |
| 42 | | | | | | | | | | | | | | | | | | | | | | | | | | | | | | | | TRG | GS | | | | | | | | |
| 43 | | | | | | | | | | | | | | | | | | | | | | | | | | | | | | | | LTD | HK | | | | | | | | |
| 44 | | | | | | | | | | | | | | | | | | | | | | | | | | | | | | | YR | GDR | K | | | | | | | | |
| 45 | | | | | | | | | | | | | | | | | | | | | | | | | | | | | | | YF | KQR | K | | | | | | | | |
| 46 | | | | | | | | | | | | | | | | | | | | | | | | | | | | | | | | SDE | KK | | | | | | | | |
| 47 | | | | | | | | | | | | | | | | | | | | | | | | | | | | | | | YL | KDG | KK | | | | | | | | |
| 48 | | | | | | | | | | | | | | | | | | | | | | | | | | | | | | | | KED | KK | | | | | | | | |
| 49 | | | | | | | | | | | | | | | | | | | | | | | | | | | | | | | | LRD | KK | | | | | | | | |
| 50 | | | | | | | | | | | | | | | | | | | | | | | | | | | | | | | | LSD | KK | | | | | | | | |

FIGURE 16B

| V# | CDR-H1 | | | | | | | | | | CDR-H2 | | | | | | | | | | CDR-H3 | | | | | | | | | | |
|---|---|---|---|---|---|---|---|---|---|---|---|---|---|---|---|---|---|---|---|---|---|---|---|---|---|---|---|---|---|---|---|
| | G | Y | T | F | T | N | Y | G | M | W | I | N | T | Y | T | G | E | P | T | Y | A | A | D | F | K | R | Y | P | H | Y | Y | G | S | H | W | Y | F | D | V |
| 51 | | | | | | | | | | | | | | | | | | | | | | | | | | | | | | | | RRD | KK | | | | | |
| 52 | | | | | | | | | | | | | | | | | | | | | | | | | | | | | | | | SHQ | KR | | | | | |
| 53 | | | | | | | | | | | | | | | | | | | | | | | | | | | | | | | YTY | D | KS | | | | | |
| 54 | | | | | | | | | | | | | | | | | | | | | | | | | | | | | | | YR | GQR | KS | | | | | |
| 55 | | | | | | | | | | | | | | | | | | | | | | | | | | | | | | | YF | KER | KS | | | | | |
| 56 | | | | | | | | | | | | | | | | | | | | | | | | | | | | | | | | QDF | KS | | | | | |
| 57 | | | | | | | | | | | | | | | | | | | | | | | | | | | | | | | YE | RDG | KS | | | | | |
| 58 | | | | | | | | | | | | | | | | | | | | | | | | | | | | | | | | RNE | KS | | | | | |
| 59 | | | | | | | | | | | | | | | | | | | | | | | | | | | | | | | YQ | RNG | KS | | | | | |
| 60 | | | | | | | | | | | | | | | | | | | | | | | | | | | | | | | | RTE | KS | | | | | |
| 61 | | | | | | | | | | | | | | | | | | | | | | | | | | | | | | | | VND | KT | | | | | |
| 62 | | | | | | | | | | | | | | | | | | | | | | | | | | | | | | | YL | KDG | MS | | | | | |
| 63 | | | | | | | | | | | | | | | | | | | | | | | | | | | | | | | | N | | | | | | |
| 64 | | | | | | | | | | | | | | | | | | | | | | | | | | | | | | | | PG | PRG | | | | | |
| 65 | | | | | | | | | | | | | | | | | | | | | | | | | | | | | | | YQ | NEG | PS | | | | | |
| 66 | | | | | | | | | | | | | | | | | | | | | | | | | | | | | Y | | | | R | | | | | |
| 67 | | | | | | | | | | | | | | | | | | | | | | | | | | | | | | | | | R | | | | | |
| 68 | | | | | | | | | | | | | | | | | | | | | | | | | | | | | | | | RDE | RE | | | | | |
| 69 | | | | | | | | | | | | | | | | | | | | | | | | | | | | | | | | SHE | RK | | | | | |
| 70 | | | | | | | | | | | | | | | | | | | | | | | | | | | | | | | | LKD | RK | | | | | |

FIGURE 16C

| V# | CDR-H1 | | | | | | | CDR-H2 | | | | | | | | | | | CDR-H3 | | | | | | | | | | | |
|---|---|---|---|---|---|---|---|---|---|---|---|---|---|---|---|---|---|---|---|---|---|---|---|---|---|---|---|---|---|---|
| | G | Y | T | F | T | N | Y | G | M | W | I | N | T | Y | T | G | E | P | T | Y | A | A | D | F | K | R | Y | P | H | Y |
| 71 | | | | | | | | | | | | | | | | | | | | | | | | | | | | | | |
| 72 | | | | | | | | | | | | | | | | | | | | | | | | | | | | | | |

| V# | CDR-H3 (cont.) | | | | | | | |
|---|---|---|---|---|---|---|---|---|
| | Y | G | S | S | H | W | Y | F | D | V |
| 71 | | LNE | RK | | | | | | | |
| 72 | | SNE | RK | | | | | | | |
| 73 | | VNE | RK | | | | | | | |
| 74 | | VTD | RK | | | | | | | |
| 75 | | GNH | RS | | | | | | | |
| 76 | YL | KDG | RS | | | | | | | |
| 77 | YL | KDR | RS | | | | | | | |
| 78 | | GFD | RS | | | | | | | |
| 79 | | RDS | RS | | | | | | | |
| 80 | YE | RDG | RS | | | | | | | |
| 81 | YL | RDG | RS | | | | | | | |
| 82 | | RNE | RS | | | | | | | |
| 83 | | SHE | RV | | | | | | | |
| 84 | YQ | KQ | SKS | | | | | | | |
| 85 | Y | | T | | | | | | | |
| 86 | | | T | | | | | | | |
| 87 | XV | VEE | TE | | | | | | | |
| 88 | | GE | TS | | | | | | | |
| 89 | X | | X | | | | | | | |
| 90 | YL | ADR | | | | | | | | |
| 91 | XV | GEQ | | | | | | | | |
| 92 | XV | GET | | | | | | | | |
| 93 | YL | KDK | | | | | | | | |

| V# | CDR-H1 | | | | | | | | | CDR-H2 | | | | | | | | | | | | | | | | | CDR-H3 | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|
| | G | Y | T | F | T | N | Y | G | M | W | I | N | T | Y | T | G | E | P | T | Y | A | A | D | F | K | R | Y | P | H | Y | Y | G | S | S | H | W | F | D | V |
| 94 | | | | | | | | | | | | | | | | | | | | | | | | | | | | | | | | | | | | | | | |
| 95 | | | | | | | | | | | | | | | | | | | | | | | | | | | | | | YL | | KDR | | | | | | | |
| 96 | | | | | | | | | | | | | | | | | | | | | | | | | | | | | | YA | | KSP | | | | | | | |
| 97 | | | | | | | | | | | | | | | | | | | | | | | | | | | | | | | | LG | | | | | | | |
| 98 | | | | | | | | | | | | | | | | | | | | | | | | | | | | | | YK | | NDK | | | | | | | |
| 99 | | | | | | | | | | | | | | | | | | | | | | | | | | | | | | YL | | NDK | | | | | | | |
| 100 | | | | | | | | | | | | | | | | | | | | | | | | | | | | | | YV | | NER | | | | | | | |
| 101 | | | | | | | | | | | | | | | | | | | | | | | | | | | | | | YA | | RDR | | | | | | | |
| 102 | | | | | | | | | | | | | | | | | | | | | | | | | | | | | | Y* | | RDR | | | | | | | |
| 103 | | | | | | | | | | | | | | | | | | | | | | | | | | | | P | Y | | N | | | | | | | | |
| 104 | | | | | | | | | | | | | | | | | | | | | | | | | | | | | Y | | | | | | | | | | |
| 105 | | | | | | | | | | | | | | | | | | | | | | | | | | | | | Y | | | | | | | | | | |
| 106 | | | | | | | | | | | | | | | | | | | | | | | | | | | | | | | | | | | | | | | |
| 107 | | | | | | | | | | | | | | | | | | | | | | | | | | | T | | | | | | | | | | | | |
| 108 | | | | | | | | | | | | | | | | | | | | | | | | | | | | | Y | | | | | R | | | | | |
| 109 | | D | | | | | | | | | | | | | | | | | | | | | | | | | | | Y | | | | | R | | | | | |
| 110 | | | | | | | | | | | | | | | | | | | | | | | | | | | | | Y | | | | | R | | | | | |
| 111 | | D | | | | | | | | | | | | | | | | | | | | | | | | | | | | | | | | RK | | | | | |
| 112 | | | | | | | | | | | | | | | | | | | | | | | | | | | | | Y | | VNE | | T | | | | | |
| 113 | | | | | | | | | | | | | | | | | | | | | | | | | | | | | Y | | VNE | | T | | | | | |

FIGURE 16F

| V# | \|CDR-H1\| G | Y | T | F | T | N | Y | G | M | \|CDR-H2\| W | I | N | T | Y | T | G | E | P | T | Y | A | A | D | F | K | R | \|CDR-H3\| Y | P | H | Y | Y | G | S | S | H | W | Y | F | D | V |
|---|---|---|---|---|---|---|---|---|---|---|---|---|---|---|---|---|---|---|---|---|---|---|---|---|---|---|---|---|---|---|---|---|---|---|---|---|---|---|---|
| 114 | | | | | | | | | | | | | | | | | | | | | | | | | | | | | Y | | | | | | | | | | |
| 115 | | | | | | | | | | | | | | | | | | | | | | | | | | | | | | | | | | | | | | | |
| 116 | | | | | | H | | | | | | | | | | | | | | | | | | | | | | | | | | | | | | | | | |
| 117 | | | | | | | | | I | | | | | | | | | | | | | | | | | | | | | | | | | | | | | | |
| 118 | | | | | D | | | | | | | | | | | | | | | | | | DK | | | DR | | | | | | | | | | | | | |
| 119 | A | | | | | | | | | | | | | | | | | | | | | | | | | | | | | | | | | | | | | | |
| 120 | | | | | | | | | | | | | | | | | | | | | | | | | | | | | | | | | | | | | | | |
| 121 | | | | F | | S | | A | MS | | | | | | | | | | | | | | | | | | | | | | | | | | | | | | |
| 122 | | | | | | | | | L | | | | | | | | | | | | | | | | | | | | | | | | | | | | | | |
| 123 | | | | | | | | | | V | | S | G | D | G | S | T | Y | Y | | D | S | | V | | G | | | | | | | | | | | | | |
| 124 | | | | | | | | | L | | | | | | | | | | | | | | | | | | | | | | | | | | | | | | |
| 125 | | | | | | | | | L | | | | | | | | | | | | | | | | | | | | | | | | | | | | | | |
| 126 | | | | | | | | | L | | | | | | | | | | | | | | | | | | | | | | | | | | | | | | |
| 127 | | | | | | | | | L | | | | | | | | | | | | | | | | | | | Y | R | | | | Q | S | A | | | | |
| 128 | | | | | | | | | L | | | | | | | | | | | | | | | | | | | Y | R | | | | Q | K | G | A | A | A | A |
| 129 | | | | | | | | | L | | | | | | | | | | | | | | | | | | | Y | R | | | | D | R | G | A | A | A | Y |
| 130 | | | | | | | | | L | | | | | | | | | | | | | | | | | | | Y | R | | | | D | A | | A | A | A | A |
| 131 | | | | | | | | | L | | | | | | | | | | | | | | | | | | | Y | R | | | | N | A | | | | | |
| 132 | | | | | | | | | L | | | | | | | | | | | | | | | | | | | Y | | | | | A | | | | | | |
| 133 | | | | | | | | | L | | | | | | | | | | | | | | | | | | | Y | | | | | A | | | | | | |
| 134 | | | | | | | | | L | | | | | | | | | | | | | | | | | | | Y | R | | | | E | | | | | | |

FIGURE 16G

| V# | \multicolumn{10}{c}{CDR-H1} | \multicolumn{17}{c}{CDR-H2} | \multicolumn{13}{c}{CDR-H3} |
|---|---|---|---|---|---|---|---|---|---|---|---|---|---|---|---|---|---|---|---|---|---|---|---|---|---|---|---|---|---|---|---|---|---|---|---|---|---|---|---|---|
| | G | Y | T | F | T | N | Y | G | M | W | W | I | N | T | Y | T | G | E | P | T | Y | A | A | D | F | K | R | Y | P | H | Y | Y | G | S | H | W | Y | F | D | V |
| 135 | | | | | | | | | | | | | | | | | | | | | | | | | | | | | Y | | | R | K | G | | | | | | |
| 136 | | | | | | | | | | | | | | | | | | | | | | | | | | | | | Y | | | R | S | G | | | | | | |
| 137 | | | | | | | | | | | | | | | | | | | | | | | | | | | | | Y | | | K | A | K | | | | | | |
| 138 | | | | | | | | | | | | | | | | | | | | | | | | | | | | | Y | | | I | N | K | | | | | | |
| 139 | | | | | | | | | | | | | | | | | | | | | | | | | | | | | Y | | | I | N | K | | | | | | |
| 140 | | | | | | | | | | | | | | | | | | | | | | | | | | | | | Y | | | R | D | N | | | | | | |
| 141 | | | | | | | | | | | | | | | | | | | | | | | | | | | | | Y | | | R | Q | N | | | | | | |
| 142 | | | | | | | | | | | | | | | | | | | | | | | | | | | | | Y | | | R | N | Q | | | | | | |
| 143 | | | | | | | | | | | | | | | | | | | | | | | | | | | | | Y | | | I | E | R | | | | | | |
| 144 | | | | | | | | | | | | | | | | | | | | | | | | | | | | | Y | | | T | N | R | | | | | | |
| 145 | | | | | | | | | | | | | | | | | | | | | | | | | | | | | Y | | | T | T | T | | | | | | |
| 146 | | | | | | | | | | | | | | | | | | | | | | | | | | | | | Y | | | T | T | T | | | | | | |
| 147 | | | | | | | | | | | | | | | | | | | | | | | | | | | | | Y | | | K | N | T | | | | | | |
| 148 | | | | | | | | | | | | | | | | | | | | | | | | | | | | | Y | | | R | N | R | | | | | | |
| 149 | | | | | | | | | | | | | | | | | | | | | | | | | | | | | Y | | | T | N | T | | | | | | |
| 150 | | | | | | | | | | | | | | | | | | | | | | | | | | | | | Y | | | R | T | T | | | | | | |
| 151 | | | Q | | | H | | | | | | | | | W | | | | | | | | | | | | | Y | | | | | | | | | | | |
| 152 | | | Q | | | H | | | | | | | | | | | | | | | | | | | | | | Y | | | W | | H | | | | | | |
| 153 | | | | | | | | | | | | | | | | | | | | | | | | | | | | Y | | | | A | H | | | | | | | |
| 154 | | | | | | | | | | | | | | | | | | | | | | | | | | | | Y | | | | | T | | | | | | | |
| 155 | | | | | | | | | | | | | | | | | | | | | | | | | | | | Y | | | | | T | | | | | | | |
| 156 | | | | | | | | | | | | | | | | | | | | | | | | | | | | Y | | | | | T | | | | | | | |
| 157 | | | | | | | | | | | | | | | | | | | | | | | | | | | | Y | | | K | E | T | | | | | | |

| V# | CDR-H1 | | | | | | | | | | CDR-H2 | | | | | | | | | | | | | | | | CDR-H3 | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|
| | G | Y | T | F | T | N | Y | G | M | W | W | I | N | T | Y | T | G | E | P | T | Y | A | D | F | K | R | Y | P | H | Y | Y | G | S | S | H | W | Y | F | D | V |
| 158 | | | | | | | | | | | | | | | | | | | | | | | | | | | | Y | Y | | R | N | | | | | | | | |
| 159 | | | | | | | | | | | | | | | | | | | | | | | | | | | | Y | Y | | R | Q | | | | | | | | |
| 160 | | | | | | | | | | | | | | | | | | | | | | | | | | | | | Y | | A | | | | | | | | | |
| 161 | | | | | | | | | | | | | | | | | | | | | | | | | | | | | Y | | E | | | | | | | | | |
| 162 | | | | | | | | | | | | | | | | | | | | | | | | | | | | | Y | | T | | | | | | | | | |
| 163 | | | | | | | | | | | | | | | | | | | | | | | | | | | | | A | | | | | | | | | | | |
| 164 | | | | | | | | | | | | | | | | | | | | | | | | | | | | | Y | A | | | | | | | | | | |
| 165 | | | | | | | | | | | | | | | | | | | | | | | | | | | A | A | | | | | | | | | | | | |
| 166 | | | | | | | | | | | | | | | | | | | | | A | | | | | | | | | | | | | | | | | | | |
| 167 | | | | | | | | | | | | | | | | | | | | | | | | | | A | | | | | | | | | | | | | | |
| 168 | | | | | | | | | | | | | | | | | | | | | | | | | A | | | | | | | | | | | | | | | |
| 169 | | | | | | | | | | | | | | | | | | | | | | | A | | | | | | | | | | | | | | | | | |
| 170 | | | | | | | | | | | | | | | | | | | | | | A | | | | | | | | | | | | | | | | | | |
| 171 | | | | | | | | | | | | | | | | | | | | | A | | | | | | | | | | | | | | | | | | | |
| 172 | | | | | | | | | | | | | | | | | | | | A | | | | | | | | | | | | | | | | | | | | |
| 173 | | | | | | | | | | | | | | | | | | | | A | | | | | | | | | | | | | | | | | | | | |
| 174 | | | | | | | | | | | | | | | | | | | A | | | | | | | | | | | | | | | | | | | | | |
| 175 | | | | | | | | | | | | | | | | | | | Q | | | | | | | | | | | | | | | | | | | | | |
| 176 | | | | | | | | | | | | | | | | | | | T | | | | | | | | | | | | | | | | | | | | | |
| 177 | | | | | | | | | | | | | | | | Y | W | | | | | | | | | | | | | | | | | | | | | | | |
| 178 | | | | | | | | | | | | | | | | Y | W | | | | | | | | | | | | | | | | | | | | | | | |
| 179 | | | | | | | | | | | | | | | | | | A | | | | | | | | | | | | | | | | | | | | | | |
| 180 | | | | | | | | | | | | | | | | | A | | | | | | | | | | | | | | | | | | | | | | | |
| 181 | | | | | | | | | | | | | | | | Y | W | D | | | | | | | | | | | | | | | | | | | | | | |

| V# | CDR-L1 | | | | | | | | | | | CDR-L2 | | | | | | | CDR-L3 | | | | | | | | |
|---|---|---|---|---|---|---|---|---|---|---|---|---|---|---|---|---|---|---|---|---|---|---|---|---|---|---|---|
| | S | A | S | Q | D | I | S | N | Y | L | N | F | T | S | S | L | H | S | Q | Q | Y | S | T | V | P | W | T |
| 206 | | | | | | | | | | | | | | | | | | | | | | | | | | | F |
| 207 | | | | | | | | | | | | | | | | | | | | | | NS | | | | | |
| 208 | | | | | | | | | | | | | | | | | | | | | | YS | | | | | |
| 209 | | | | | | | | | | | | | | | | | | | | | SY | | | | | | |
| 210 | | | | | | | | | | | | | | | | | | | | | | | A | | | | |
| 211 | | | | | | | | | | | | | | | | | | | | | | | N | | | | |
| 212 | | | | | | | | | | | | | | | | | | | | | | | S | | | | |
| 213 | A | | | | | | | | | | | | | | | | | | | | | | | | | | |
| 214 | | A | | | | | | | | | | | | | | | | | | | | | | | | | |
| 215 | | | A | | | | | | | | | | | | | | | | | | | | | | | | |
| 216 | | | | A | | | | | | | | | | | | | | | | | | | | | | | |
| 217 | | | | | A | | | | | | | | | | | | | | | | | | | | | | |
| 218 | | | | | | A | | | | | | | | | | | | | | | | | | | | | |
| 219 | | | | | | | A | | | | | | | | | | | | | | | | | | | | |
| 220 | | | | | | | | A | | | | | | | | | | | | | | | | | | | |
| 221 | | | | | | | | | A | | | | | | | | | | | | | | | | | | |
| 222 | | | | | | | | | | A | | | | | | | | | | | | | | | | | |
| 223 | | | | | | | | | | | A | | | | | | | | | | | | | | | | |
| 224 | | | | | | | | | | | | A | | | | | | | | | | | | | | | |
| 225 | | | | | | | | | | | | | A | | | | | | | | | | | | | | |
| 226 | | | | | | | | | | | | | | A | | | | | | | | | | | | | |
| 227 | | | | | | | | | | | | | | | A | | | | | | | | | | | | |
| 228 | | | | | | | | | | | | | | | | A | | | | | | | | | | | |
| 229 | | | | | | | | | | | | | | | | | A | | | | | | | | | | |
| 230 | | | | | | | | | | | | | | | | | | A | | | | | | | | | |
| 231 | | | | | | | | | | | | | | | | | | | A | | | | | | | | |
| 232 | | | | | | | | | | | | | | | | | | | | A | | | | | | | |
| 233 | | | | | | | | | | | | | | | | | | | | | A | | | | | | |
| 234 | | | | | | | | | | | | | | | | | | | | | | A | | | | | |
| 235 | | | | | | | | | | | | | | | | | | | | | | | A | | | | |
| 236 | | | | | | | | | | | | | | | | | | | | | | | | A | | | |
| 237 | | | | | | | | | | | | | | | | | | | | | | | | | A | | |
| 238 | | | | | | | | | | | | | | | | | | | | | | | | | | A | |
| 239 | | | | | | | | | | | | | | | | | | | | | | | | | | | A |
| 240 | R | | | N | E | Q | L | | | | | | | | | | | | | | | | | | | | |
| 241 | R | | | N | E | Q | | | | | | | | | | | | | | | | | | | | | |
| 242 | R | | | | | | S | | | | | A | A | A | | | E | | | | | N | S | L | | | |

FIGURE 17

| SEQ ID NO: | N | T | Y | T | G | E | P | T | Y | A | A | D | F | K | R | # responders* | % responders | Average SI |
|---|---|---|---|---|---|---|---|---|---|---|---|---|---|---|---|---|---|---|
| 62 | | | | | | | | | | | | | | | | 5 | 5.38 | 1.67 |
| 97 | | F | | | | | | | | | | | | | | 9 | 9.68 | 1.59 |
| 98 | | | | | | | | | | | F | | | | | 6 | 6.45 | 1.51 |
| 99 | | | | | | | | | | | E | | | | | 5 | 5.38 | 1.82 |
| 100 | | | | | | | | | | | D | | | | | 7 | 7.53 | 1.39 |
| 101 | | | | | | | | | | | | G | | | | 6 | 6.45 | 1.45 |
| 102 | | | | | | | | | | | | L | | | | 8 | 8.60 | 1.44 |
| 103 | | | | | | | | | | | | Q | | | | 10 | 10.75 | 1.46 |
| 104 | | | | | | | | | | | | T | | | | 4 | 4.30 | 1.40 |
| 105 | | | | | | | | | | | | K | | | | 5 | 5.38 | 1.50 |
| 106 | | | | | | | | | | | | R | | | | 4 | 4.30 | 1.32 |
| 107 | | | | | | | | | | | | E | | | | 5 | 5.38 | 1.32 |
| 108 | | | | | | | | | | | | H | | | | 4 | 4.30 | 1.21 |
| 109 | | | | | | | | | | | | | S | | | 2 | 2.15 | 1.22 |
| 110 | | | | | | | | | | | | | V | | | 4 | 4.30 | 1.19 |
| 111 | | | | | | | | | | | | | Q | | | 2 | 2.15 | 1.13 |
| 112 | | | | | | | | | | | | | | V | | 10 | 10.75 | 1.59 |
| 113 | | | | | | | | | | | | | | F | | 13 | 13.98 | 1.82 |
| 114 | | | | | | | | | | | | | | H | | 9 | 9.68 | 1.55 |
| 115 | | | | | | | | | | | | | | N | | 7 | 7.53 | 1.41 |
| 116 | | | | | | | | | | | | | | S | | 4 | 4.30 | 1.24 |
| 117 | | | | | | | | | | | | | | Q | | 7 | 7.53 | 1.33 |
| 118 | | | | | | | | | | | | | | K | | 4 | 4.30 | 1.27 |
| 119 | | | | | | | | | | | | | | | I | 9 | 9.68 | 2.06 |

| SEQ ID NO: | N | T | Y | T | G | E | P | T | Y | A | A | D | F | K | R | # responders* | % responders | Average SI |
|---|---|---|---|---|---|---|---|---|---|---|---|---|---|---|---|---|---|---|
| 120 | | | F | | | | | | | | | F | | | | 7 | 7.53 | 1.68 |
| 121 | | | F | | | | | | | | | E | | | | 8 | 8.60 | 1.51 |
| 122 | | | F | | | | | | | | | D | | | | 4 | 4.30 | 1.34 |
| 123 | | | F | | | | | | | | G | | | | | 3 | 3.23 | 1.19 |
| 124 | | | F | | | | | | | | L | | | | | 6 | 6.45 | 1.29 |
| 125 | | | F | | | | | | | | Q | | | | | 6 | 6.45 | 1.34 |
| 126 | | | F | | | | | | | | T | | | | | 6 | 6.45 | 1.34 |
| 127 | | | F | | | | | | | | K | | | | | 9 | 9.68 | 1.48 |
| 128 | | | F | | | | | | | | R | | | | | 8 | 8.60 | 1.67 |
| 129 | | | F | | | | | | | | E | | | | | 10 | 10.75 | 1.61 |
| 130 | | | F | | | | | | | | H | | | | | 8 | 8.60 | 1.64 |
| 131 | | | F | | | | | | | | | | | S | | 4 | 4.30 | 1.21 |
| 132 | | | F | | | | | | | | | | | V | | 3 | 3.23 | 1.12 |
| 133 | | | F | | | | | | | | | | | Q | | 2 | 2.15 | 1.15 |
| 134 | | | F | | | | | | | | | | | | V | 6 | 6.45 | 1.41 |
| 135 | | | F | | | | | | | | | | | | F | 12 | 12.90 | 1.65 |
| 136 | | | F | | | | | | | | | | | | H | 11 | 11.83 | 1.70 |
| 137 | | | F | | | | | | | | | | | | N | 9 | 9.68 | 1.80 |
| 138 | | | F | | | | | | | | | | | | S | 11 | 11.83 | 1.80 |
| 139 | | | F | | | | | | | | | | | | Q | 7 | 7.53 | 1.34 |
| 140 | | | F | | | | | | | | | | | | K | 4 | 4.30 | 1.17 |
| 141 | | | F | | | | | | | | | | | | I | 5 | 5.38 | 1.36 |
| 62 | | | | | | | | | | | | | | | | 6 | 6.45 | 1.33 |
| | * n= 93 | | | | | | | | | | | | | | | | | |

FIGURE 18 (continued)

| SEQ ID NO: | A | E | D | T | A | V | Y | Y | C | A | K | Y | P | H | Y | # responders* | % responders | Average SI |
|---|---|---|---|---|---|---|---|---|---|---|---|---|---|---|---|---|---|---|
| 74 | | | | | | | | | | | | | | | | 7 | 7.53 | 1.45 |
| 142 | | | | | | | | | | | | | | D | | 11 | 11.83 | 1.62 |
| 143 | | | | | | | | | | | | | | E | | 6 | 6.45 | 1.43 |
| 144 | | | | | | | | | | | | | | P | | 10 | 10.75 | 1.97 |
| 145 | | | | | | | | | | | | | | | F | 4 | 4.30 | 1.26 |
| 146 | | | | | | | | | | | | | | D | F | 5 | 5.38 | 1.22 |
| 147 | | | | | | | | | | | | | | E | F | 1 | 1.08 | 1.09 |
| 148 | | | | | | | | | | | | | | P | F | 5 | 5.38 | 1.22 |
| 74 | | | | | | | | | | | | | | | | 6 | 6.45 | 1.34 |
| | * n= 93 | | | | | | | | | | | | | | | | | |

FIGURE 19

| SEQ ID NO: | Q | Q | K | P | G | K | A | P | K | V | L | I | Y | F | T | # responders* | % responders | Average SI |
|---|---|---|---|---|---|---|---|---|---|---|---|---|---|---|---|---|---|---|
| 25 | | | | | | | | | | | | | | | | 24 | 25.81 | 3.69 |
| 149 | | | | | | | | | | | L | | | | | 18 | 19.35 | 2.05 |
| 150 | | | | | | | | | | | | | | D | | 6 | 6.45 | 1.42 |
| 151 | | | | | | | | | | | | | | S | | 6 | 6.45 | 1.43 |
| 152 | | | | | | | | | | | | | | G | | 2 | 2.15 | 1.27 |
| 153 | | | | | | | | | | | | | | A | | 2 | 2.15 | 1.17 |
| 154 | | | | | | | | | | | | | | | A | 2 | 2.15 | 1.16 |
| 155 | | | | | | | | | | | | | | D | A | 7 | 7.53 | 1.87 |
| 156 | | | | | | | | | | | | | | S | A | 8 | 8.60 | 2.34 |
| 157 | | | | | | | | | | | | | | G | A | 8 | 8.60 | 1.63 |
| 158 | | | | | | | | | | | | | | A | A | 11 | 11.83 | 1.77 |
| 159 | | | | | | | | | | | L | | | D | | 12 | 12.90 | 1.49 |
| 160 | | | | | | | | | | | L | | | S | | 3 | 3.23 | 1.25 |
| 161 | | | | | | | | | | | L | | | G | | 4 | 4.30 | 1.27 |
| 162 | | | | | | | | | | | L | | | A | | 5 | 5.38 | 1.28 |
| 163 | | | | | | | | | | | L | | | | A | 23 | 24.73 | 2.49 |
| 164 | | | | | | | | | | | L | | | D | A | 9 | 9.68 | 2.23 |
| 165 | | | | | | | | | | | L | | | S | A | 10 | 10.75 | 1.39 |
| 166 | | | | | | | | | | | L | | | G | A | 6 | 6.45 | 1.52 |
| 167 | | | | | | | | | | | L | | | A | A | 5 | 5.38 | 1.27 |
| 25 | | | | | | | | | | | | | | | | 14 | 15.05 | 2.30 |
| *n= 93 | | | | | | | | | | | | | | | | | | |

FIGURE 20

| SEQ ID NO: | | | | |
|---|---|---|---|---|
| VH | CDR2 16%/2.16 SI | # Responders* | % | SI |
| 62 | NTYTGEPTYAADFKR | 5 | 5.38 | 1.67 |
| 109 | NTYTGEPTYAADFSR | 2 | 2.15 | 1.22 |
| 111 | NTYTGEPTYAADFQR | 2 | 2.15 | 1.13 |
| 133 | NTFTGEPTYAADFQR | 2 | 2.15 | 1.15 |
| 62 | NTYTGEPTYAADFKR | 6 | 6.45 | 1.33 |
| VH | CDR3 9%/1.45 SI | | | |
| 74 | AEDTAVYYCAKYPHY | 7 | 7.53 | 1.45 |
| 143 | AEDTAVYYCAKYPEF | 1 | 1.08 | 1.09 |
| 74 | AEDTAVYYCAKYPHY | 6 | 6.45 | 1.34 |
| VL | CDR2 15%/1.45 SI | | | |
| 25 | QQKPGKAPKVLIYFT | 24 | 25.81 | 3.69 |
| 154 | QQKPGKAPKVLIYFA | 2 | 2.15 | 1.16 |
| 25 | QQKPGKAPKVLIYFT | 14 | 15.05 | 2.30 |
| * n= 93 | | | | |

FIGURE 21

| Single Variable Region Mutants | MFI |
|---|---|
| WT | 194.78 |
| VH K64Q | 230.4 |
| VH K64S | 168.08 |
| VH Y53F.K64Q | 217.4 |
| VH H97E.Y98F | 310.32 |
| VL T51A | 295.93 |

FIGURE 22

| Combined Variable Region Mutants | $EC_{50}$ |
|---|---|
| WT | 152.4 |
| VH K64Q/VL T51A | 174.2 |
| VH K64S/VL T51A | 263.2 |
| VH Y53F.K64Q/VL T51A | 104 |
| VH H97E.Y98F/VL T51A | 26.22 |

FIGURE 23

|  | SEQ ID NOS | | |
|---|---|---|---|
| Variant No. | CDR-H1 | CDR-H2 | CDR-H3 |
| 1 | n/a | 4 | 237 |
| 2 | n/a | 190 | 238 |
| 3 | n/a | 191 | 238 |
| 4 | n/a | 192 | 238 |
| 5 | n/a | 193 | 238 |
| 6 | n/a | 194 | 238 |
| 7 | n/a | 195 | 238 |
| 8 | n/a | 196 | 238 |
| 9 | n/a | 197 | 238 |
| 10 | n/a | 198 | 238 |
| 11 | n/a | 199 | 238 |
| 12 | n/a | 4 | 238 |
| 13 | n/a | 4 | 239 |
| 14 | n/a | 4 | 240 |
| 15 | n/a | 4 | 241 |
| 16 | n/a | 200 | n/a |
| 17 | n/a | 201 | n/a |
| 18 | n/a | 202 | n/a |
| 19 | n/a | 203 | 5 |
| 20 | n/a | 204 | 5 |
| 21 | n/a | 205 | n/a |
| 22 | n/a | 206 | n/a |
| 23 | n/a | 207 | n/a |
| 24 | n/a | 208 | n/a |
| 25 | n/a | 209 | n/a |
| 26 | n/a | 210 | n/a |
| 27 | n/a | 211 | n/a |
| 28 | n/a | 212 | n/a |

FIGURE 24A

|             | SEQ ID NOS |        |        |
|-------------|------------|--------|--------|
| Variant No. | CDR-H1     | CDR-H2 | CDR-H3 |
| 29          | n/a        | n/a    | 242    |
| 30          | n/a        | n/a    | 243    |
| 31          | n/a        | n/a    | 244    |
| 32          | n/a        | n/a    | 245    |
| 33          | n/a        | n/a    | 246    |
| 34          | n/a        | n/a    | 247    |
| 35          | n/a        | n/a    | 248    |
| 36          | n/a        | n/a    | 249    |
| 37          | n/a        | n/a    | 250    |
| 38          | n/a        | n/a    | 251    |
| 39          | n/a        | n/a    | 252    |
| 40          | n/a        | n/a    | 253    |
| 41          | n/a        | n/a    | 254    |
| 42          | n/a        | n/a    | 255    |
| 43          | n/a        | n/a    | 256    |
| 44          | n/a        | n/a    | 257    |
| 45          | n/a        | n/a    | 258    |
| 46          | n/a        | n/a    | 259    |
| 47          | n/a        | n/a    | 260    |
| 48          | n/a        | n/a    | 261    |
| 49          | n/a        | n/a    | 262    |
| 50          | n/a        | n/a    | 263    |

FIGURE 24B

| Variant No. | SEQ ID NOS | | |
|---|---|---|---|
| | CDR-H1 | CDR-H2 | CDR-H3 |
| 51 | n/a | n/a | 264 |
| 52 | n/a | n/a | 265 |
| 53 | n/a | n/a | 266 |
| 54 | n/a | n/a | 267 |
| 55 | n/a | n/a | 268 |
| 56 | n/a | n/a | 269 |
| 57 | n/a | n/a | 270 |
| 58 | n/a | n/a | 271 |
| 59 | n/a | n/a | 272 |
| 60 | n/a | n/a | 273 |
| 61 | n/a | n/a | 274 |
| 62 | n/a | n/a | 275 |
| 63 | n/a | n/a | 276 |
| 64 | n/a | n/a | 277 |
| 65 | n/a | n/a | 278 |
| 66 | n/a | n/a | 279 |
| 67 | n/a | n/a | 280 |
| 68 | n/a | n/a | 281 |
| 69 | n/a | n/a | 282 |
| 70 | n/a | n/a | 283 |

FIGURE 24C

|             | SEQ ID NOS |        |        |
| ----------- | ---------- | ------ | ------ |
| Variant No. | CDR-H1     | CDR-H2 | CDR-H3 |
| 71          | n/a        | n/a    | 284    |
| 72          | n/a        | n/a    | 285    |
| 73          | n/a        | n/a    | 286    |
| 74          | n/a        | n/a    | 287    |
| 75          | n/a        | n/a    | 288    |
| 76          | n/a        | n/a    | 289    |
| 77          | n/a        | n/a    | 290    |
| 78          | n/a        | n/a    | 291    |
| 79          | n/a        | n/a    | 292    |
| 80          | n/a        | n/a    | 293    |
| 81          | n/a        | n/a    | 294    |
| 82          | n/a        | n/a    | 295    |
| 83          | n/a        | n/a    | 296    |
| 84          | n/a        | n/a    | 297    |
| 85          | n/a        | n/a    | 298    |
| 86          | n/a        | n/a    | 299    |
| 87          | n/a        | n/a    | 300    |
| 88          | n/a        | n/a    | 301    |
| 89          | n/a        | n/a    | 302    |
| 90          | n/a        | n/a    | 303    |
| 91          | n/a        | n/a    | 304    |
| 92          | n/a        | n/a    | 305    |
| 93          | n/a        | n/a    | 306    |

FIGURE 24D

| Variant No. | SEQ ID NOS | | |
|---|---|---|---|
| | CDR-H1 | CDR-H2 | CDR-H3 |
| 94 | n/a | n/a | 307 |
| 95 | n/a | n/a | 308 |
| 96 | n/a | n/a | 309 |
| 97 | n/a | n/a | 310 |
| 98 | n/a | n/a | 311 |
| 99 | n/a | n/a | 312 |
| 100 | n/a | n/a | 313 |
| 101 | n/a | n/a | 314 |
| 102 | n/a | n/a | 315 |
| 103 | n/a | n/a | 316 |
| 104 | n/a | n/a | 317 |
| 105 | n/a | n/a | 318 |
| 106 | n/a | n/a | 319 |
| 107 | n/a | n/a | 320 |
| 108 | 411 | 4 | 321 |
| 109 | 168 | 4 | 322 |
| 110 | 411 | 4 | 323 |
| 111 | 168 | 4 | 324 |
| 112 | 169 | 4 | 325 |
| 113 | 411 | 4 | 326 |

FIGURE 24E

|  | SEQ ID NOS | | |
|---|---|---|---|
| Variant No. | CDR-H1 | CDR-H2 | CDR-H3 |
| 114 | 411 | 4 | 321 |
| 115 | 170 | 213 | n/a |
| 116 | 169 | 4 | 5 |
| 117 | 168 | 4 | n/a |
| 118 | 169 | n/a | n/a |
| 119 | 171 | 4 | 5 |
| 120 | 411 | 4 | 327 |
| 121 | 172 | 214 | 328 |
| 122 | 411 | 4 | 329 |
| 123 | 411 | 4 | 330 |
| 124 | 411 | 4 | 331 |
| 125 | 411 | 4 | 332 |
| 126 | 411 | 4 | 333 |
| 127 | 411 | 4 | 334 |
| 128 | 169 | 4 | 335 |
| 129 | 169 | 4 | 336 |
| 130 | 169 | 4 | 337 |
| 131 | 169 | 4 | 338 |
| 132 | 169 | 4 | 339 |
| 133 | 411 | 4 | 340 |
| 134 | 169 | 4 | 341 |

FIGURE 24F

| Variant No. | SEQ ID NOS | | |
|---|---|---|---|
| | CDR-H1 | CDR-H2 | CDR-H3 |
| 135 | 169 | 4 | 342 |
| 136 | 169 | 4 | 343 |
| 137 | 169 | 4 | 344 |
| 138 | 169 | 4 | 345 |
| 139 | 169 | 4 | 346 |
| 140 | 169 | 4 | 347 |
| 141 | 169 | 4 | 348 |
| 142 | 169 | 4 | 349 |
| 143 | 169 | 4 | 350 |
| 144 | 169 | 4 | 351 |
| 145 | 169 | 4 | 352 |
| 146 | 169 | 4 | 353 |
| 147 | 169 | 4 | 354 |
| 148 | 169 | 4 | 355 |
| 149 | 169 | 4 | 356 |
| 150 | 169 | 4 | 357 |
| 151 | 169 | 4 | 358 |
| 152 | 173 | 215 | 359 |
| 153 | 173 | 4 | 359 |
| 154 | 169 | 4 | 359 |
| 155 | 169 | 4 | 241 |
| 156 | 411 | 4 | 360 |
| 157 | 169 | 4 | 361 |

FIGURE 24G

| Variant No. | SEQ ID NOS | | |
|---|---|---|---|
| | CDR-H1 | CDR-H2 | CDR-H3 |
| 158 | 169 | 4 | 362 |
| 159 | 169 | 4 | 363 |
| 160 | 411 | 4 | 364 |
| 161 | 169 | 4 | 365 |
| 162 | 169 | 4 | 366 |
| 163 | 411 | 4 | 367 |
| 164 | 411 | 4 | 368 |
| 165 | 169 | 4 | 369 |
| 166 | 411 | 4 | 370 |
| 167 | 411 | 4 | 371 |
| 168 | 411 | 216 | 5 |
| 169 | 411 | 217 | 5 |
| 170 | 411 | 218 | 5 |
| 171 | 411 | 219 | 5 |
| 172 | 411 | 220 | 5 |
| 173 | 411 | 221 | 5 |
| 174 | 411 | 222 | 5 |
| 175 | 411 | 223 | 5 |
| 176 | 411 | 224 | 5 |
| 177 | 169 | 225 | 5 |
| 178 | 169 | 226 | 5 |
| 179 | 411 | 227 | 5 |
| 180 | 411 | 228 | 5 |
| 181 | 169 | 229 | 5 |

FIGURE 24H

|  | SEQ ID NOS | | |
| --- | --- | --- | --- |
| Variant No. | CDR-H1 | CDR-H2 | CDR-H3 |
| 182 | 411 | 230 | 5 |
| 183 | 169 | 231 | 5 |
| 184 | 411 | 232 | 5 |
| 185 | 411 | 233 | 5 |
| 186 | 411 | 234 | 5 |
| 187 | 411 | 235 | 5 |
| 188 | 174 | 4 | 5 |
| 189 | 175 | 4 | 5 |
| 190 | 176 | 4 | 5 |
| 191 | 177 | 4 | 5 |
| 192 | 178 | 4 | 5 |
| 193 | 173 | 4 | 5 |
| 194 | 179 | 4 | 5 |
| 195 | 180 | 4 | 5 |
| 196 | 181 | 4 | 5 |
| 197 | 182 | 4 | 5 |
| 198 | 183 | 4 | 5 |
| 199 | 184 | 4 | 5 |
| 200 | 185 | 4 | 5 |
| 201 | 186 | 4 | 5 |
| 202 | 187 | 4 | 5 |
| 203 | 188 | 4 | 5 |
| 204 | 189 | 4 | 5 |
| 205 | 411 | 236 | 5 |

FIGURE 24I

|         | SEQ ID NOS |         |         |
|---------|------------|---------|---------|
| Variant # | CDR-L1   | CDR-L2  | CDR-L3  |
| 206     | 6          | 7       | 394     |
| 207     | n/a        | n/a     | 395     |
| 208     | n/a        | n/a     | 396     |
| 209     | n/a        | n/a     | 397     |
| 210     | n/a        | n/a     | 398     |
| 211     | n/a        | n/a     | 399     |
| 212     | n/a        | n/a     | 400     |
| 213     | 372        | 7       | 8       |
| 214     | 373        | 7       | 8       |
| 215     | 374        | 7       | 8       |
| 216     | 375        | 7       | 8       |
| 217     | 376        | 7       | 8       |
| 218     | 377        | 7       | 8       |
| 219     | 378        | 7       | 8       |
| 220     | 379        | 7       | 8       |
| 221     | 380        | 7       | 8       |
| 222     | 381        | 7       | 8       |
| 223     | 382        | 7       | 8       |
| 224     | 6          | 386     | 8       |
| 225     | 6          | 387     | 8       |
| 226     | 6          | 388     | 8       |
| 227     | 6          | 389     | 8       |
| 228     | 6          | 390     | 8       |
| 229     | 6          | 391     | 8       |
| 230     | 6          | 392     | 8       |
| 231     | 6          | 7       | 401     |
| 232     | 6          | 7       | 402     |
| 233     | 6          | 7       | 403     |
| 234     | 6          | 7       | 404     |
| 235     | 6          | 7       | 405     |
| 236     | 6          | 7       | 406     |
| 237     | 6          | 7       | 407     |
| 238     | 6          | 7       | 408     |
| 239     | 6          | 7       | 409     |
| 240     | 383        | 7       | 8       |
| 241     | 384        | 7       | 8       |
| 242     | 385        | 393     | 410     |

FIGURE 24J

```
                              SEQUENCE LISTING

<160> NUMBER OF SEQ ID NOS: 412

<210> SEQ ID NO 1
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 2
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg
            100                 105

<210> SEQ ID NO 3
```

-continued

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Tyr Thr Phe Thr Asn Tyr Gly Met Asn
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Trp Ile Asn Thr Tyr Thr Gly Glu Pro Thr Tyr Ala Ala Asp Phe Lys
1               5                   10                  15

Arg

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Pro His Tyr Tyr Gly Ser Ser His Trp Tyr Phe Asp Val
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Ala Ser Gln Asp Ile Ser Asn Tyr Leu Asn
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Phe Thr Ser Ser Leu His Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 8

Gln Gln Tyr Ser Thr Val Pro Trp Thr
1               5

<210> SEQ ID NO 9
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Leu
225                 230

<210> SEQ ID NO 10
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile

```
                35                  40                  45
Tyr Phe Thr Ser Ser Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Tyr Asp Phe Thr His Tyr Gly Met Asn
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Pro Tyr Tyr Tyr Gly Thr Ser His Trp Tyr Phe Asp Val
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Ile Gln Met Thr Gln Ser Pro Ser Ser Leu Ser Ala Ser Val
1               5                   10                  15

<210> SEQ ID NO 14
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Thr Gln Ser Pro Ser Ser Leu Ser Ala Ser Val Gly Asp Arg
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Pro Ser Ser Leu Ser Ala Ser Val Gly Asp Arg Val Thr Ile
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Leu Ser Ala Ser Val Gly Asp Arg Val Thr Ile Thr Cys Ser
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Ser Val Gly Asp Arg Val Thr Ile Thr Cys Ser Ala Ser Gln
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Asp Arg Val Thr Ile Thr Cys Ser Ala Ser Gln Asp Ile Ser
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19
```

```
Val Thr Ile Thr Cys Ser Ala Ser Gln Asp Ile Ser Asn Tyr Leu
1               5                   10                  15
```

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Thr Cys Ser Ala Ser Gln Asp Ile Ser Asn Tyr Leu Asn Trp Tyr
1               5                   10                  15
```

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Ala Ser Gln Asp Ile Ser Asn Tyr Leu Asn Trp Tyr Gln Gln Lys
1               5                   10                  15
```

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Asp Ile Ser Asn Tyr Leu Asn Trp Tyr Gln Gln Lys Pro Gly Lys
1               5                   10                  15
```

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

```
Asn Tyr Leu Asn Trp Tyr Gln Gln Lys Pro Gly Lys Ala Pro Lys
1               5                   10                  15
```

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Asn Trp Tyr Gln Gln Lys Pro Gly Lys Ala Pro Lys Val Leu Ile
1               5                   10                  15
```

<210> SEQ ID NO 25
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 25

Gln Gln Lys Pro Gly Lys Ala Pro Lys Val Leu Ile Tyr Phe Thr
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Pro Gly Lys Ala Pro Lys Val Leu Ile Tyr Phe Thr Ser Ser Leu
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Pro Lys Val Leu Ile Tyr Phe Thr Ser Ser Leu His Ser Gly
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Val Leu Ile Tyr Phe Thr Ser Ser Leu His Ser Gly Val Pro Ser
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Phe Thr Ser Ser Leu His Ser Gly Val Pro Ser Arg Phe Ser
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Ser Leu His Ser Gly Val Pro Ser Arg Phe Ser Gly Ser Gly
1               5                   10                  15
```

```
<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

His Ser Gly Val Pro Ser Arg Phe Ser Gly Ser Gly Ser Gly Thr
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Val Pro Ser Arg Phe Ser Gly Ser Gly Ser Gly Thr Asp Phe Thr
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Phe Ser Gly Ser Gly Ser Gly Thr Asp Phe Thr Leu Thr Ile
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Ser Gly Ser Gly Thr Asp Phe Thr Leu Thr Ile Ser Ser Leu
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Gly Thr Asp Phe Thr Leu Thr Ile Ser Ser Leu Gln Pro Glu
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36
```

Asp Phe Thr Leu Thr Ile Ser Ser Leu Gln Pro Glu Asp Phe Ala
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Thr Ile Ser Ser Leu Gln Pro Glu Asp Phe Ala Thr Tyr Tyr
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Ser Leu Gln Pro Glu Asp Phe Ala Thr Tyr Tyr Cys Gln Gln
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Pro Glu Asp Phe Ala Thr Tyr Tyr Cys Gln Gln Tyr Ser Thr
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Phe Ala Thr Tyr Tyr Cys Gln Gln Tyr Ser Thr Val Pro Trp
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Thr Tyr Tyr Cys Gln Gln Tyr Ser Thr Val Pro Trp Thr Phe Gly
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Cys Gln Gln Tyr Ser Thr Val Pro Trp Thr Phe Gly Gln Gly Thr
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Tyr Ser Thr Val Pro Trp Thr Phe Gly Gln Gly Thr Lys Val Glu
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Val Pro Trp Thr Phe Gly Gln Gly Thr Lys Val Glu Ile Lys Arg
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Glu Val Gln Leu Val Glu Ser Gly Gly Gly Leu Val Gln Pro Gly
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Val Glu Ser Gly Gly Gly Leu Val Gln Pro Gly Gly Ser Leu
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Gly Gly Gly Leu Val Gln Pro Gly Gly Ser Leu Arg Leu Ser
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Leu Val Gln Pro Gly Gly Ser Leu Arg Leu Ser Cys Ala Ala
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Pro Gly Gly Ser Leu Arg Leu Ser Cys Ala Ala Ser Gly Tyr
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Ser Leu Arg Leu Ser Cys Ala Ala Ser Gly Tyr Thr Phe Thr
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Leu Ser Cys Ala Ala Ser Gly Tyr Thr Phe Thr Asn Tyr Gly
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Cys Ala Ala Ser Gly Tyr Thr Phe Thr Asn Tyr Gly Met Asn Trp
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 53

Ser Gly Tyr Thr Phe Thr Asn Tyr Gly Met Asn Trp Val Arg Gln
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Thr Phe Thr Asn Tyr Gly Met Asn Trp Val Arg Gln Ala Pro Gly
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asn Tyr Gly Met Asn Trp Val Arg Gln Ala Pro Gly Lys Gly Leu
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Met Asn Trp Val Arg Gln Ala Pro Gly Lys Gly Leu Glu Trp Val
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Val Arg Gln Ala Pro Gly Lys Gly Leu Glu Trp Val Gly Trp Ile
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Pro Gly Lys Gly Leu Glu Trp Val Gly Trp Ile Asn Thr Tyr
1               5                   10                  15

<210> SEQ ID NO 59
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 59

Lys Gly Leu Glu Trp Val Gly Trp Ile Asn Thr Tyr Thr Gly Glu
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Trp Val Gly Trp Ile Asn Thr Tyr Thr Gly Glu Pro Thr Tyr
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Trp Ile Asn Thr Tyr Thr Gly Glu Pro Thr Tyr Ala Ala Asp
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asn Thr Tyr Thr Gly Glu Pro Thr Tyr Ala Ala Asp Phe Lys Arg
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Thr Gly Glu Pro Thr Tyr Ala Ala Asp Phe Lys Arg Arg Phe Thr
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Pro Thr Tyr Ala Ala Asp Phe Lys Arg Arg Phe Thr Phe Ser Leu
1               5                   10                  15
```

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Ala Asp Phe Lys Arg Arg Phe Thr Phe Ser Leu Asp Thr Ser
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Phe Lys Arg Arg Phe Thr Phe Ser Leu Asp Thr Ser Lys Ser Thr
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Phe Thr Phe Ser Leu Asp Thr Ser Lys Ser Thr Ala Tyr Leu
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Phe Ser Leu Asp Thr Ser Lys Ser Thr Ala Tyr Leu Gln Met Asn
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Thr Ser Lys Ser Thr Ala Tyr Leu Gln Met Asn Ser Leu Arg
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Ser Thr Ala Tyr Leu Gln Met Asn Ser Leu Arg Ala Glu Asp
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ala Tyr Leu Gln Met Asn Ser Leu Arg Ala Glu Asp Thr Ala Val
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Met Asn Ser Leu Arg Ala Glu Asp Thr Ala Val Tyr Tyr Cys
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Leu Arg Ala Glu Asp Thr Ala Val Tyr Tyr Cys Ala Lys Tyr
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Glu Asp Thr Ala Val Tyr Tyr Cys Ala Lys Tyr Pro His Tyr
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Thr Ala Val Tyr Tyr Cys Ala Lys Tyr Pro His Tyr Tyr Gly Ser
1               5                   10                  15

<210> SEQ ID NO 76
<211> LENGTH: 15

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Tyr Tyr Cys Ala Lys Tyr Pro His Tyr Tyr Gly Ser Ser His Trp
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Lys Tyr Pro His Tyr Tyr Gly Ser Ser His Trp Tyr Phe Asp
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Pro His Tyr Tyr Gly Ser Ser His Trp Tyr Phe Asp Val Trp Gly
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Tyr Gly Ser Ser His Trp Tyr Phe Asp Val Trp Gly Gln Gly Thr
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser His Trp Tyr Phe Asp Val Trp Gly Gln Gly Thr Leu Val Thr
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Tyr Phe Asp Val Trp Gly Gln Gly Thr Leu Val Thr Val Ser Ser
```

<210> SEQ ID NO 82
<211> LENGTH: 123
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Phe Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Asp Tyr Asp Gly Gly Ser His Trp Tyr Phe Asp Val
            100                 105                 110

Trp Gly Gln Gly Thr Leu Val Thr Val Ser Ser
        115                 120

<210> SEQ ID NO 83
<211> LENGTH: 123
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Phe Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Pro Tyr Asp Gly Gly Ser His Trp Tyr Phe Asp Val
            100                 105                 110

Trp Gly Gln Gly Thr Leu Val Thr Val Ser Ser
        115                 120

<210> SEQ ID NO 84
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Phe Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Pro Tyr Glu Gly Ser Ser His Trp Tyr Phe Asp Val
            100                 105                 110

Trp Gly Gln Gly Thr Leu Val Thr Val Ser Ser
        115                 120

<210> SEQ ID NO 85
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Phe Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Glu Tyr Glu Gly Ser Ser His Trp Tyr Phe Asp Val
            100                 105                 110

Trp Gly Gln Gly Thr Leu Val Thr Val Ser Ser
        115                 120

<210> SEQ ID NO 86
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Phe Tyr
            20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Asp Tyr Glu Gly Ser Ser His Trp Tyr Phe Asp Val
            100                 105                 110

Trp Gly Gln Gly Thr Leu Val Thr Val Ser Ser
            115                 120

<210> SEQ ID NO 87
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Phe Tyr
            20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Glu Tyr Asp Gly Gly Ser His Trp Tyr Phe Asp Val
            100                 105                 110

Trp Gly Gln Gly Thr Leu Val Thr Val Ser Ser
            115                 120

<210> SEQ ID NO 88
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Phe Tyr
            20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
65                  70                  75                  80

-continued

Leu Gln Met Asn Ser Leu Arg Ala Glu Asp Thr Ala Val Tyr Tyr Cys
                85                  90                  95

Ala Lys Tyr Pro His Tyr Asp Gly Gly Ser His Trp Tyr Phe Asp Val
            100                 105                 110

Trp Gly Gln Gly Thr Leu Val Thr Val Ser Ser
        115                 120

<210> SEQ ID NO 89
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Phe Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Pro Tyr Asp Gly Ser Ser His Trp Tyr Phe Asp Val
            100                 105                 110

Trp Gly Gln Gly Thr Leu Val Thr Val Ser Ser
        115                 120

<210> SEQ ID NO 90
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Phe Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Asp Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 91
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Phe Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 92
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Pro Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 93
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Glu Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 94
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Phe Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser His Trp Tyr Phe Asp Val
            100                 105                 110

Trp Gly Gln Gly Thr Leu Val Thr Val Ser Ser
        115                 120

<210> SEQ ID NO 95
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30
```

```
Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro Asp Tyr Tyr Gly Ser Ser His Trp Tyr Phe Asp Val
                100                 105                 110

Trp Gly Gln Gly Thr Leu Val Thr Val Ser Ser
            115                 120
```

<210> SEQ ID NO 96
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Thr Phe Tyr
             20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro Pro Tyr Tyr Gly Ser His Trp Tyr Phe Asp Val
                100                 105                 110

Trp Gly Gln Gly Thr Leu Val Thr Val Ser Ser
            115                 120
```

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

```
Asn Thr Phe Thr Gly Glu Pro Thr Tyr Ala Ala Asp Phe Lys Arg
 1               5                  10                  15
```

<210> SEQ ID NO 98
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

```
Asn Thr Tyr Thr Gly Glu Pro Thr Tyr Ala Phe Asp Phe Lys Arg
```

```
<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asn Thr Tyr Thr Gly Glu Pro Thr Tyr Ala Glu Asp Phe Lys Arg
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Asn Thr Tyr Thr Gly Glu Pro Thr Tyr Ala Asp Asp Phe Lys Arg
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Asn Thr Tyr Thr Gly Glu Pro Thr Tyr Ala Ala Gly Phe Lys Arg
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Asn Thr Tyr Thr Gly Glu Pro Thr Tyr Ala Ala Leu Phe Lys Arg
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Asn Thr Tyr Thr Gly Glu Pro Thr Tyr Ala Ala Gln Phe Lys Arg
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 104

Asn Thr Tyr Thr Gly Glu Pro Thr Tyr Ala Ala Thr Phe Lys Arg
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Asn Thr Tyr Thr Gly Glu Pro Thr Tyr Ala Ala Lys Phe Lys Arg
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asn Thr Tyr Thr Gly Glu Pro Thr Tyr Ala Ala Arg Phe Lys Arg
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Asn Thr Tyr Thr Gly Glu Pro Thr Tyr Ala Ala Glu Phe Lys Arg
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asn Thr Tyr Thr Gly Glu Pro Thr Tyr Ala Ala His Phe Lys Arg
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Asn Thr Tyr Thr Gly Glu Pro Thr Tyr Ala Ala Asp Phe Ser Arg
1               5                   10                  15

<210> SEQ ID NO 110

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Asn Thr Tyr Thr Gly Glu Pro Thr Tyr Ala Ala Asp Phe Val Arg
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Asn Thr Tyr Thr Gly Glu Pro Thr Tyr Ala Ala Asp Phe Gln Arg
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Asn Thr Tyr Thr Gly Glu Pro Thr Tyr Ala Ala Asp Phe Lys Val
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Asn Thr Tyr Thr Gly Glu Pro Thr Tyr Ala Ala Asp Phe Lys Phe
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asn Thr Tyr Thr Gly Glu Pro Thr Tyr Ala Ala Asp Phe Lys His
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115
```

Asn Thr Tyr Thr Gly Glu Pro Thr Tyr Ala Ala Asp Phe Lys Asn
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Asn Thr Tyr Thr Gly Glu Pro Thr Tyr Ala Ala Asp Phe Lys Ser
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asn Thr Tyr Thr Gly Glu Pro Thr Tyr Ala Ala Asp Phe Lys Gln
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Asn Thr Tyr Thr Gly Glu Pro Thr Tyr Ala Ala Asp Phe Lys Lys
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Asn Thr Tyr Thr Gly Glu Pro Thr Tyr Ala Ala Asp Phe Lys Ile
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Asn Thr Phe Thr Gly Glu Pro Thr Tyr Ala Phe Asp Phe Lys Arg
1               5                   10                  15

<210> SEQ ID NO 121
<211> LENGTH: 15
<212> TYPE: PRT
<213> ORGANISM: Artificial Sequence
<220> FEATURE:

<223> OTHER INFORMATION: Description of Artificial Sequence: Synthetic
     peptide

<400> SEQUENCE: 121

Asn Thr Phe Thr Gly Glu Pro Thr Tyr Ala Glu Asp Phe Lys Arg
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 122

Asn Thr Phe Thr Gly Glu Pro Thr Tyr Ala Asp Asp Phe Lys Arg
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 123

Asn Thr Phe Thr Gly Glu Pro Thr Tyr Ala Ala Gly Phe Lys Arg
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 124

Asn Thr Phe Thr Gly Glu Pro Thr Tyr Ala Ala Leu Phe Lys Arg
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 125

Asn Thr Phe Thr Gly Glu Pro Thr Tyr Ala Ala Gln Phe Lys Arg
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 126

Asn Thr Phe Thr Gly Glu Pro Thr Tyr Ala Ala Thr Phe Lys Arg
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Asn Thr Phe Thr Gly Glu Pro Thr Tyr Ala Ala Lys Phe Lys Arg
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Asn Thr Phe Thr Gly Glu Pro Thr Tyr Ala Ala Arg Phe Lys Arg
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Asn Thr Phe Thr Gly Glu Pro Thr Tyr Ala Ala Glu Phe Lys Arg
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Asn Thr Phe Thr Gly Glu Pro Thr Tyr Ala Ala His Phe Lys Arg
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Asn Thr Phe Thr Gly Glu Pro Thr Tyr Ala Ala Asp Phe Ser Arg
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

```
Asn Thr Phe Thr Gly Glu Pro Thr Tyr Ala Ala Asp Phe Val Arg
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Asn Thr Phe Thr Gly Glu Pro Thr Tyr Ala Ala Asp Phe Gln Arg
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Asn Thr Phe Thr Gly Glu Pro Thr Tyr Ala Ala Asp Phe Lys Val
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asn Thr Phe Thr Gly Glu Pro Thr Tyr Ala Ala Asp Phe Lys Phe
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Asn Thr Phe Thr Gly Glu Pro Thr Tyr Ala Ala Asp Phe Lys His
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Asn Thr Phe Thr Gly Glu Pro Thr Tyr Ala Ala Asp Phe Lys Asn
1               5                   10                  15

<210> SEQ ID NO 138
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 138

Asn Thr Phe Thr Gly Glu Pro Thr Tyr Ala Ala Asp Phe Lys Ser
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asn Thr Phe Thr Gly Glu Pro Thr Tyr Ala Ala Asp Phe Lys Gln
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Asn Thr Phe Thr Gly Glu Pro Thr Tyr Ala Ala Asp Phe Lys Lys
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Asn Thr Phe Thr Gly Glu Pro Thr Tyr Ala Ala Asp Phe Lys Ile
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ala Glu Asp Thr Ala Val Tyr Tyr Cys Ala Lys Tyr Pro Asp Tyr
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ala Glu Asp Thr Ala Val Tyr Tyr Cys Ala Lys Tyr Pro Glu Tyr
1               5                   10                  15
```

<210> SEQ ID NO 144
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ala Glu Asp Thr Ala Val Tyr Tyr Cys Ala Lys Tyr Pro Pro Tyr
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ala Glu Asp Thr Ala Val Tyr Tyr Cys Ala Lys Tyr Pro His Phe
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ala Glu Asp Thr Ala Val Tyr Tyr Cys Ala Lys Tyr Pro Asp Phe
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ala Glu Asp Thr Ala Val Tyr Tyr Cys Ala Lys Tyr Pro Glu Phe
1               5                   10                  15

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ala Glu Asp Thr Ala Val Tyr Tyr Cys Ala Lys Tyr Pro Pro Phe
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 149

Gln Gln Lys Pro Gly Lys Ala Pro Lys Leu Leu Ile Tyr Phe Thr
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gln Gln Lys Pro Gly Lys Ala Pro Lys Val Leu Ile Tyr Asp Thr
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gln Gln Lys Pro Gly Lys Ala Pro Lys Val Leu Ile Tyr Ser Thr
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gln Gln Lys Pro Gly Lys Ala Pro Lys Val Leu Ile Tyr Gly Thr
1               5                   10                  15

<210> SEQ ID NO 153
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gln Gln Lys Pro Gly Lys Ala Pro Lys Val Leu Ile Tyr Ala Thr
1               5                   10                  15

<210> SEQ ID NO 154
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gln Gln Lys Pro Gly Lys Ala Pro Lys Val Leu Ile Tyr Phe Ala
1               5                   10                  15

<210> SEQ ID NO 155
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 155

Gln Gln Lys Pro Gly Lys Ala Pro Lys Val Leu Ile Tyr Asp Ala
1               5                   10                  15

<210> SEQ ID NO 156
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gln Gln Lys Pro Gly Lys Ala Pro Lys Val Leu Ile Tyr Ser Ala
1               5                   10                  15

<210> SEQ ID NO 157
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gln Gln Lys Pro Gly Lys Ala Pro Lys Val Leu Ile Tyr Gly Ala
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gln Gln Lys Pro Gly Lys Ala Pro Lys Val Leu Ile Tyr Ala Ala
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gln Gln Lys Pro Gly Lys Ala Pro Lys Leu Leu Ile Tyr Asp Thr
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gln Gln Lys Pro Gly Lys Ala Pro Lys Leu Leu Ile Tyr Ser Thr
1               5                   10                  15
```

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gln Gln Lys Pro Gly Lys Ala Pro Lys Leu Leu Ile Tyr Gly Thr
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gln Gln Lys Pro Gly Lys Ala Pro Lys Leu Leu Ile Tyr Ala Thr
1               5                   10                  15

<210> SEQ ID NO 163
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gln Gln Lys Pro Gly Lys Ala Pro Lys Leu Leu Ile Tyr Phe Ala
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gln Gln Lys Pro Gly Lys Ala Pro Lys Leu Leu Ile Tyr Asp Ala
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gln Gln Lys Pro Gly Lys Ala Pro Lys Leu Leu Ile Tyr Ser Ala
1               5                   10                  15

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gln Gln Lys Pro Gly Lys Ala Pro Lys Leu Leu Ile Tyr Gly Ala
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Gln Gln Lys Pro Gly Lys Ala Pro Lys Leu Leu Ile Tyr Ala Ala
1               5                   10                  15

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Gly Tyr Asp Phe Thr Asn Tyr Gly Met
1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gly Tyr Thr Phe Thr Asn Tyr Gly Ile
1               5

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Tyr Thr Phe Thr His Tyr Gly Met
1               5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ala Tyr Thr Phe Thr Asn Tyr Gly Met
1               5

<210> SEQ ID NO 172
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Phe Thr Phe Ser Ser Tyr Ala Met Ser
1               5                   10

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gly Tyr Asp Phe Thr His Tyr Gly Ile
1               5

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Tyr Thr Phe Thr Asn Tyr Gly Ala
1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gly Tyr Asp Phe Gly His Tyr Gly Ile
1               5

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Tyr Glu Phe Gln His Tyr Gly Ile
1               5

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Tyr Asp Phe Ser His Tyr Gly Ile
```

```
1               5

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Tyr Glu Phe Ser His Tyr Gly Ile
1               5

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gly Tyr Glu Phe Thr His Tyr Gly Ile
1               5

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gly Tyr Thr Phe Thr His Tyr Gly Ile
1               5

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gly Tyr Asp Phe Thr Asn Tyr Gly Ile
1               5

<210> SEQ ID NO 182
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Tyr Thr Phe Thr Asn Tyr Gly Met Ala
1               5                   10

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                          peptide

<400> SEQUENCE: 183

Gly Tyr Thr Phe Thr Asn Tyr Ala Met
1               5

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gly Tyr Thr Phe Thr Ala Tyr Gly Met
1               5

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Tyr Thr Phe Ala Asn Tyr Gly Met
1               5

<210> SEQ ID NO 186
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Gly Tyr Thr Ala Thr Asn Tyr Gly Met
1               5

<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Gly Tyr Ala Phe Thr Asn Tyr Gly Met
1               5

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gly Ala Thr Phe Thr Asn Tyr Gly Met
1               5

<210> SEQ ID NO 189
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gly Tyr Thr Phe Thr Asn Ala Gly Met
1               5

<210> SEQ ID NO 190
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Trp Ile Asn Thr Tyr Thr Gly Glu Pro Thr Tyr Ala Asp Glu Phe Thr
1               5                   10                  15
Arg

<210> SEQ ID NO 191
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Trp Ile Asn Thr Tyr Thr Gly Glu Pro Thr Tyr Val Asp Glu Phe Lys
1               5                   10                  15
Arg

<210> SEQ ID NO 192
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Trp Ile Asn Thr Tyr Thr Gly Glu Pro Thr Tyr Ala Glu Glu Phe Lys
1               5                   10                  15
Arg

<210> SEQ ID NO 193
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Trp Ile Asn Thr Tyr Thr Gly Glu Pro Thr Tyr Ala Pro Glu Phe Lys
1               5                   10                  15
Arg

<210> SEQ ID NO 194
<211> LENGTH: 17
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Trp Ile Asn Thr Tyr Thr Gly Glu Pro Thr Tyr Ala Gln Glu Phe Lys
1               5                   10                  15

Arg

<210> SEQ ID NO 195
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Trp Ile Asn Thr Tyr Thr Gly Glu Thr Thr Tyr Ala His Asp Phe Lys
1               5                   10                  15

Arg

<210> SEQ ID NO 196
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Trp Ile Asn Thr Tyr Asn Gly Glu Thr Thr Tyr Ala Pro Asp Phe Lys
1               5                   10                  15

Arg

<210> SEQ ID NO 197
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Trp Ile Asn Thr Tyr Asn Gly Glu Pro Thr Tyr Ala Pro Asp Phe Lys
1               5                   10                  15

Arg

<210> SEQ ID NO 198
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Trp Ile Asn Thr Tyr Thr Gly Glu Ser Thr Tyr Ala Gln Asp Phe Lys
1               5                   10                  15

Arg

<210> SEQ ID NO 199

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Trp Ile Asn Thr Tyr Thr Asn Asn Pro Thr Tyr Ala Gln Asp Phe Lys
1               5                   10                  15

Arg

<210> SEQ ID NO 200
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Trp Ile Asn Thr Tyr Thr Gly Glu Pro Thr Tyr Ala Asp Asp Phe Lys
1               5                   10                  15

Glu

<210> SEQ ID NO 201
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Trp Ile Asn Thr Tyr Thr Gly Glu Pro Thr Tyr Ala Glu Glu Phe Thr
1               5                   10                  15

Arg

<210> SEQ ID NO 202
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Trp Ile Asn Thr Tyr Thr Gly Glu Pro Thr Tyr Ala His Glu Phe Thr
1               5                   10                  15

Arg

<210> SEQ ID NO 203
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Trp Ile Asn Thr Tyr Thr Gly Glu Pro Thr Tyr Ala Pro Asp Phe Thr
1               5                   10                  15

Arg
```

```
<210> SEQ ID NO 204
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Trp Ile Asn Thr Tyr Thr Gly Glu Pro Thr Tyr Ala His Glu Phe Lys
1               5                   10                  15

Arg

<210> SEQ ID NO 205
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Trp Ile Asn Thr Tyr Thr Gly Glu Pro Thr Tyr Ala Pro Glu Phe Lys
1               5                   10                  15

Arg

<210> SEQ ID NO 206
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Trp Ile Asn Thr Tyr Thr Gly Glu Pro Thr Tyr Ala Gln Glu Phe Lys
1               5                   10                  15

Arg

<210> SEQ ID NO 207
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Trp Ile Asn Thr Tyr Thr Gly Glu Thr Thr Tyr Ala His Asp Phe Lys
1               5                   10                  15

Arg

<210> SEQ ID NO 208
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Trp Ile Asn Thr Tyr Asn Gly Glu Pro Thr Tyr Ala Pro Asp Phe Lys
1               5                   10                  15

Arg
```

<210> SEQ ID NO 209
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Trp Ile Asn Thr Tyr Thr Gly Glu Pro Thr Tyr Ala Pro Asp Phe Lys
1               5                   10                  15

Arg

<210> SEQ ID NO 210
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Trp Ile Asn Thr Tyr Thr Gly Glu Ser Thr Tyr Ala Gln Asp Phe Lys
1               5                   10                  15

Arg

<210> SEQ ID NO 211
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Trp Ile Asn Thr Asn Asn Gly Glu Pro Thr Tyr Ala Ala Asp Phe Lys
1               5                   10                  15

Arg

<210> SEQ ID NO 212
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 212

Trp Ile Asn Thr Xaa Thr Gly Glu Pro Thr Tyr Ala Ala Asp Phe Lys
1               5                   10                  15

Arg

<210> SEQ ID NO 213
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

```
Trp Ile Asn Thr Tyr Thr Gly Glu Pro Thr Tyr Ala Ala Asp Lys Phe
1               5                   10                  15

Lys Asp Arg

<210> SEQ ID NO 214
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Val Ile Ser Gly Asp Gly Gly Ser Thr Tyr Tyr Ala Asp Ser Val Lys
1               5                   10                  15

Gly

<210> SEQ ID NO 215
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Trp Ile Asn Thr Trp Thr Gly Glu Pro Thr Tyr Ala Ala Asp Phe Lys
1               5                   10                  15

Arg

<210> SEQ ID NO 216
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Trp Ile Asn Thr Tyr Thr Gly Glu Pro Thr Tyr Ala Ala Asp Phe Lys
1               5                   10                  15

Ala

<210> SEQ ID NO 217
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Trp Ile Asn Thr Tyr Thr Gly Glu Pro Thr Tyr Ala Ala Asp Phe Ala
1               5                   10                  15

Arg

<210> SEQ ID NO 218
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218
```

Trp Ile Asn Thr Tyr Thr Gly Glu Pro Thr Tyr Ala Ala Asp Ala Lys
1               5                   10                  15

Arg

<210> SEQ ID NO 219
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Trp Ile Asn Thr Tyr Thr Gly Glu Pro Thr Tyr Ala Ala Ala Phe Lys
1               5                   10                  15

Arg

<210> SEQ ID NO 220
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Trp Ile Asn Thr Tyr Thr Gly Glu Pro Thr Tyr Ala Ala Asp Phe Lys
1               5                   10                  15

Arg

<210> SEQ ID NO 221
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Trp Ile Asn Thr Tyr Thr Gly Glu Pro Thr Tyr Ala Ala Asp Phe Lys
1               5                   10                  15

Arg

<210> SEQ ID NO 222
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Trp Ile Asn Thr Tyr Thr Gly Glu Pro Ala Tyr Ala Ala Asp Phe Lys
1               5                   10                  15

Arg

<210> SEQ ID NO 223
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 223

Trp Ile Asn Thr Tyr Thr Gly Glu Ala Thr Tyr Ala Ala Asp Phe Lys
1               5                   10                  15

Arg

<210> SEQ ID NO 224
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Trp Ile Asn Thr Tyr Thr Gly Ala Pro Thr Tyr Ala Ala Asp Phe Lys
1               5                   10                  15

Arg

<210> SEQ ID NO 225
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Trp Ile Asn Thr Trp Thr Gly Gln Pro Thr Tyr Ala Ala Asp Phe Lys
1               5                   10                  15

Arg

<210> SEQ ID NO 226
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Trp Ile Asn Thr Trp Thr Gly Thr Pro Thr Tyr Ala Ala Asp Phe Lys
1               5                   10                  15

Arg

<210> SEQ ID NO 227
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Trp Ile Asn Thr Tyr Thr Ala Glu Pro Thr Tyr Ala Ala Asp Phe Lys
1               5                   10                  15

Arg

<210> SEQ ID NO 228
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Trp Ile Asn Thr Tyr Ala Gly Glu Pro Thr Tyr Ala Ala Asp Phe Lys
1               5                   10                  15
Arg

<210> SEQ ID NO 229
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Trp Ile Asn Thr Trp Asp Gly Glu Pro Thr Tyr Ala Ala Asp Phe Lys
1               5                   10                  15
Arg

<210> SEQ ID NO 230
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Trp Ile Asn Thr Ala Thr Gly Glu Pro Thr Tyr Ala Ala Asp Phe Lys
1               5                   10                  15
Arg

<210> SEQ ID NO 231
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Trp Ile Asn Thr Trp Thr Gly Glu Pro Thr Tyr Ala Ala Asp Phe Lys
1               5                   10                  15
Arg

<210> SEQ ID NO 232
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Trp Ile Asn Ala Tyr Thr Gly Glu Pro Thr Tyr Ala Ala Asp Phe Lys
1               5                   10                  15
Arg

<210> SEQ ID NO 233
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 233

Trp Ile Ala Thr Tyr Thr Gly Glu Pro Thr Tyr Ala Ala Asp Phe Lys
1               5                   10                  15
Arg

<210> SEQ ID NO 234
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Trp Ala Asn Thr Tyr Thr Gly Glu Pro Thr Tyr Ala Ala Asp Phe Lys
1               5                   10                  15
Arg

<210> SEQ ID NO 235
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ala Ile Asn Thr Tyr Thr Gly Glu Pro Thr Tyr Ala Ala Asp Phe Lys
1               5                   10                  15
Arg

<210> SEQ ID NO 236
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Trp Ile Asn Thr Tyr Thr Gly Glu Pro Thr Ala Ala Ala Asp Phe Lys
1               5                   10                  15
Arg

<210> SEQ ID NO 237
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Tyr Pro Lys Tyr Tyr Gly Lys Ser His Trp Tyr Phe Asp Val
1               5                   10

<210> SEQ ID NO 238
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Tyr Pro Tyr Tyr Tyr Gly Arg Ser His Trp Tyr Phe Asp Val
1               5                   10

<210> SEQ ID NO 239
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Tyr Pro His Tyr Tyr Val Asn Glu Arg Lys Ser His Trp Tyr Phe Asp
1               5                   10                  15

Val

<210> SEQ ID NO 240
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Tyr Pro Tyr Tyr Tyr Gly Thr Ser His Trp Tyr Phe Asp Val
1               5                   10

<210> SEQ ID NO 241
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Tyr Pro His Tyr Tyr Gly Thr Ser His Trp Tyr Phe Asp Val
1               5                   10

<210> SEQ ID NO 242
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Tyr Pro His Tyr Tyr Gly Ser Ser His Trp Tyr Phe Asp Leu
1               5                   10

<210> SEQ ID NO 243
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Tyr Pro His Tyr Tyr Gly Arg Ser Gln Trp Tyr Phe Asp Val
1               5                   10

```
<210> SEQ ID NO 244
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Tyr Pro His Tyr Tyr Gly Gly Cys His Trp Tyr Phe Asp Val
1               5                   10

<210> SEQ ID NO 245
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Tyr Pro His Tyr Tyr Gly Thr Thr His Trp Tyr Phe Asp Val
1               5                   10

<210> SEQ ID NO 246
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Asp Pro His Tyr Tyr Gly Ser Tyr His Trp Tyr Phe Asp Val
1               5                   10

<210> SEQ ID NO 247
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Tyr Pro His Tyr Tyr Gly Ser Tyr His Trp Tyr Phe Asp Val
1               5                   10

<210> SEQ ID NO 248
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Arg Pro His Tyr Tyr Gly Ala Ser His Trp Tyr Phe Asp Val
1               5                   10

<210> SEQ ID NO 249
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249
```

```
Tyr Pro His Tyr Tyr Gly Ala Ser His Trp Tyr Phe Asp Val
1               5                   10
```

<210> SEQ ID NO 250
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

```
Tyr Pro His Tyr Tyr Ser Gly Glu Arg Glu Ser Ser His Trp Tyr Phe
1               5                   10                  15

Asp Val
```

<210> SEQ ID NO 251
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

```
Tyr Pro His Tyr Tyr Ala Arg Glu Gly Gly Ser His Trp Tyr Phe Asp
1               5                   10                  15

Val
```

<210> SEQ ID NO 252
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

```
Tyr Pro His Tyr Tyr Ser Val Glu Gly Gly Ser His Trp Tyr Phe Asp
1               5                   10                  15

Val
```

<210> SEQ ID NO 253
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

```
Tyr Pro His Tyr Tyr Gly Gly Ser His Trp Tyr Phe Asp Val
1               5                   10
```

<210> SEQ ID NO 254
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

```
Tyr Pro His Tyr Tyr Gln Ser Glu Gly Arg Ser His Trp Tyr Phe Asp
1               5                   10                  15
```

Val

<210> SEQ ID NO 255
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Tyr Pro His Tyr Tyr His Thr Arg Gly Gly Ser Ser His Trp Tyr Phe
1               5                   10                  15

Asp Val

<210> SEQ ID NO 256
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Tyr Pro His Tyr Tyr Leu Thr Asp His Lys Ser His Trp Tyr Phe Asp
1               5                   10                  15

Val

<210> SEQ ID NO 257
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Tyr Pro His Tyr Tyr Arg Gly Asp Arg Lys Ser His Trp Tyr Phe Asp
1               5                   10                  15

Val

<210> SEQ ID NO 258
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Tyr Pro His Tyr Tyr Glu Lys Gln Arg Lys Ser His Trp Tyr Phe Asp
1               5                   10                  15

Val

<210> SEQ ID NO 259
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Tyr Pro His Tyr Tyr Ser Asp Glu Lys Lys Ser His Trp Tyr Phe Asp

```
1               5                   10                  15
```
Val

<210> SEQ ID NO 260
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

```
Tyr Pro His Tyr Tyr Leu Lys Asp Gly Lys Lys Ser His Trp Tyr Phe
1               5                   10                  15
```
Asp Val

<210> SEQ ID NO 261
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

```
Tyr Pro His Tyr Tyr Lys Glu Asp Lys Lys Ser His Trp Tyr Phe Asp
1               5                   10                  15
```
Val

<210> SEQ ID NO 262
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

```
Tyr Pro His Tyr Tyr Leu Arg Asp Lys Lys Ser His Trp Tyr Phe Asp
1               5                   10                  15
```
Val

<210> SEQ ID NO 263
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

```
Tyr Pro His Tyr Tyr Leu Ser Asp Lys Lys Ser His Trp Tyr Phe Asp
1               5                   10                  15
```
Val

<210> SEQ ID NO 264
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

```
Tyr Pro His Tyr Tyr Arg Arg Asp Lys Lys Ser His Trp Tyr Phe Asp
1               5                   10                  15
Val

<210> SEQ ID NO 265
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Tyr Pro His Tyr Tyr Ser His Gln Lys Arg Ser His Trp Tyr Phe Asp
1               5                   10                  15
Val

<210> SEQ ID NO 266
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Tyr Pro His Tyr Tyr Thr Tyr Asp Lys Ser Ser His Trp Tyr Phe Asp
1               5                   10                  15
Val

<210> SEQ ID NO 267
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Tyr Pro His Tyr Tyr Arg Gly Gln Arg Lys Ser Ser His Trp Tyr Phe
1               5                   10                  15
Asp Val

<210> SEQ ID NO 268
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Tyr Pro His Tyr Tyr Glu Lys Glu Arg Lys Ser Ser His Trp Tyr Phe
1               5                   10                  15
Asp Val

<210> SEQ ID NO 269
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269
```

Tyr Pro His Tyr Tyr Gln Asp Glu Lys Ser Ser His Trp Tyr Phe Asp
1               5                   10                  15

Val

<210> SEQ ID NO 270
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Tyr Pro His Tyr Tyr Glu Arg Asp Gly Lys Ser Ser His Trp Tyr Phe
1               5                   10                  15

Asp Val

<210> SEQ ID NO 271
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Tyr Pro His Tyr Tyr Arg Asn Glu Lys Ser Ser His Trp Tyr Phe Asp
1               5                   10                  15

Val

<210> SEQ ID NO 272
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Tyr Pro His Tyr Tyr Gln Arg Asn Gly Lys Ser Ser His Trp Tyr Phe
1               5                   10                  15

Asp Val

<210> SEQ ID NO 273
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Tyr Pro His Tyr Tyr Arg Thr Glu Lys Ser Ser His Trp Tyr Phe Asp
1               5                   10                  15

Val

<210> SEQ ID NO 274
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Tyr Pro His Tyr Val Asn Asp Lys Thr Ser His Trp Tyr Phe Asp
1               5                   10                  15

Val

<210> SEQ ID NO 275
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Tyr Pro His Tyr Tyr Leu Lys Asp Gly Met Ser Ser His Trp Tyr Phe
1               5                   10                  15

Asp Val

<210> SEQ ID NO 276
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Tyr Pro His Tyr Tyr Gly Asn Ser His Trp Tyr Phe Asp Val
1               5                   10

<210> SEQ ID NO 277
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Tyr Pro His Tyr Tyr Pro Ser Pro Arg Gly Ser His Trp Tyr Phe Asp
1               5                   10                  15

Val

<210> SEQ ID NO 278
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Tyr Pro His Tyr Tyr Gln Asn Glu Gly Pro Ser Ser His Trp Tyr Phe
1               5                   10                  15

Asp Val

<210> SEQ ID NO 279
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

```
Tyr Pro Tyr Tyr Tyr Gly Arg Ser His Trp Tyr Phe Asp Val
1               5                   10

<210> SEQ ID NO 280
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Tyr Pro His Tyr Tyr Gly Arg Ser His Trp Tyr Phe Asp Val
1               5                   10

<210> SEQ ID NO 281
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Tyr Pro His Tyr Tyr Arg Asp Glu Arg Glu Ser His Trp Tyr Phe Asp
1               5                   10                  15

Val

<210> SEQ ID NO 282
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Tyr Pro His Tyr Tyr Ser His Glu Arg Lys Ser His Trp Tyr Phe Asp
1               5                   10                  15

Val

<210> SEQ ID NO 283
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Tyr Pro His Tyr Tyr Leu Lys Asp Arg Lys Ser His Trp Tyr Phe Asp
1               5                   10                  15

Val

<210> SEQ ID NO 284
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Tyr Pro His Tyr Tyr Leu Asn Glu Arg Lys Ser His Trp Tyr Phe Asp
1               5                   10                  15
```

Val

<210> SEQ ID NO 285
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Tyr Pro His Tyr Tyr Ser Asn Glu Arg Lys Ser His Trp Tyr Phe Asp
1               5                   10                  15

Val

<210> SEQ ID NO 286
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Tyr Pro His Tyr Tyr Val Asn Glu Arg Lys Ser His Trp Tyr Phe Asp
1               5                   10                  15

Val

<210> SEQ ID NO 287
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Tyr Pro His Tyr Tyr Val Thr Asp Arg Lys Ser His Trp Tyr Phe Asp
1               5                   10                  15

Val

<210> SEQ ID NO 288
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Tyr Pro His Tyr Tyr Gly Asn His Arg Ser Ser His Trp Tyr Phe Asp
1               5                   10                  15

Val

<210> SEQ ID NO 289
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Tyr Pro His Tyr Tyr Leu Lys Asp Gly Arg Ser Ser His Trp Tyr Phe

-continued

```
1               5                   10                  15

Asp Val

<210> SEQ ID NO 290
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Tyr Pro His Tyr Tyr Leu Lys Asp Arg Arg Ser Ser His Trp Tyr Phe
1               5                   10                  15

Asp Val

<210> SEQ ID NO 291
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Tyr Pro His Tyr Tyr Gln Arg Asp Arg Ser Ser His Trp Tyr Phe Asp
1               5                   10                  15

Val

<210> SEQ ID NO 292
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Tyr Pro His Tyr Tyr Arg Asp Glu Arg Ser Ser His Trp Tyr Phe Asp
1               5                   10                  15

Val

<210> SEQ ID NO 293
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Tyr Pro His Tyr Tyr Glu Arg Asp Gly Arg Ser Ser His Trp Tyr Phe
1               5                   10                  15

Asp Val

<210> SEQ ID NO 294
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294
```

```
Tyr Pro His Tyr Tyr Leu Arg Asp Gly Arg Ser Ser His Trp Tyr Phe
1               5                   10                  15

Asp Val

<210> SEQ ID NO 295
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Tyr Pro His Tyr Tyr Arg Asn Glu Arg Ser Ser His Trp Tyr Phe Asp
1               5                   10                  15

Val

<210> SEQ ID NO 296
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Tyr Pro His Tyr Tyr Ser His Glu Arg Val Ser His Trp Tyr Phe Asp
1               5                   10                  15

Val

<210> SEQ ID NO 297
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Tyr Pro His Tyr Tyr Gln Lys Gln Ser Lys Ser Ser His Trp Tyr Phe
1               5                   10                  15

Asp Val

<210> SEQ ID NO 298
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Tyr Pro Tyr Tyr Tyr Gly Thr Ser His Trp Tyr Phe Asp Val
1               5                   10

<210> SEQ ID NO 299
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Tyr Pro His Tyr Tyr Gly Thr Ser His Trp Tyr Phe Asp Val
```

<210> SEQ ID NO 300
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Tyr Pro His Tyr Tyr Val Glu Glu Thr Glu Ser His Trp Tyr Phe Asp
1               5                   10                  15
Val

<210> SEQ ID NO 301
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Tyr Pro His Tyr Tyr Val Gly Glu Thr Ser Ser His Trp Tyr Phe Asp
1               5                   10                  15
Val

<210> SEQ ID NO 302
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 302

Tyr Pro Xaa Tyr Tyr Gly Xaa Ser His Trp Tyr Phe Asp Val
1               5                   10

<210> SEQ ID NO 303
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Tyr Pro His Tyr Tyr Leu Ala Asp Arg Ser Ser His Trp Tyr Phe Asp
1               5                   10                  15
Val

<210> SEQ ID NO 304
<211> LENGTH: 17
<212> TYPE: PRT
<213> ORGANISM: Artificial Sequence
<220> FEATURE:
<223> OTHER INFORMATION: Description of Artificial Sequence: Synthetic

```
                         peptide

<400> SEQUENCE: 304

Tyr Pro His Tyr Tyr Val Gly Glu Gln Ser Ser His Trp Tyr Phe Asp
1               5                   10                  15

Val

<210> SEQ ID NO 305
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Tyr Pro His Tyr Tyr Val Gly Glu Thr Ser Ser His Trp Tyr Phe Asp
1               5                   10                  15

Val

<210> SEQ ID NO 306
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Tyr Pro His Tyr Tyr Leu Lys Asp Lys Ser Ser His Trp Tyr Phe Asp
1               5                   10                  15

Val

<210> SEQ ID NO 307
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Tyr Pro His Tyr Tyr Leu Lys Asp Arg Ser Ser His Trp Tyr Phe Asp
1               5                   10                  15

Val

<210> SEQ ID NO 308
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Tyr Pro His Tyr Tyr Ala Lys Glu Arg Ser Ser His Trp Tyr Phe Asp
1               5                   10                  15

Val

<210> SEQ ID NO 309
<211> LENGTH: 15
<212> TYPE: PRT
<213> ORGANISM: Artificial Sequence
<220> FEATURE:
```

<223> OTHER INFORMATION: Description of Artificial Sequence: Synthetic
peptide

<400> SEQUENCE: 309

Tyr Pro His Tyr Tyr Leu Gly Ser Ser His Trp Tyr Phe Asp Val
1               5                   10                  15

<210> SEQ ID NO 310
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 310

Tyr Pro His Tyr Tyr Lys Asn Asp Lys Ser Ser His Trp Tyr Phe Asp
1               5                   10                  15
Val

<210> SEQ ID NO 311
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 311

Tyr Pro His Tyr Tyr Leu Asn Asp Lys Ser Ser His Trp Tyr Phe Asp
1               5                   10                  15
Val

<210> SEQ ID NO 312
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 312

Tyr Pro His Tyr Tyr Val Asn Glu Arg Ser Ser His Trp Tyr Phe Asp
1               5                   10                  15
Val

<210> SEQ ID NO 313
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 313

Tyr Pro His Tyr Tyr Ala Arg Asp Arg Ser Ser His Trp Tyr Phe Asp
1               5                   10                  15
Val

<210> SEQ ID NO 314
<211> LENGTH: 17
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 314

Tyr Pro His Tyr Tyr Arg Asp Arg Ser Ser His Trp Tyr Phe Asp
1               5                   10                  15
Val

<210> SEQ ID NO 315
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Tyr Pro Tyr Tyr Asn Gly Ser Ser His Trp Tyr Phe Asp Val
1               5                   10

<210> SEQ ID NO 316
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Pro Pro Tyr Tyr Tyr Gly Ser Ser His Trp Tyr Phe Asp Val
1               5                   10

<210> SEQ ID NO 317
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Tyr Pro Tyr Tyr Tyr Gly Ser Ser His Trp Tyr Phe Asp Val
1               5                   10

<210> SEQ ID NO 318
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Tyr His Tyr Tyr Gly Ser Ser His Trp Tyr Phe Asp Val
1               5                   10

<210> SEQ ID NO 319
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Tyr Tyr His Tyr Tyr Gly Ser Ser His Trp Tyr Phe Asp Val
1               5                   10

<210> SEQ ID NO 320
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Thr Pro His Tyr Tyr Gly Ser Ser His Trp Tyr Phe Asp Val
1               5                   10

<210> SEQ ID NO 321
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Tyr Pro Tyr Tyr Tyr Gly Ser Ser His Trp Tyr Phe Asp Val
1               5                   10

<210> SEQ ID NO 322
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Tyr Pro His Tyr Tyr Gly Arg Ser His Trp Tyr Phe Asp Val
1               5                   10

<210> SEQ ID NO 323
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Tyr Pro His Tyr Tyr Gly Arg Ser His Trp Tyr Phe Asp Val
1               5                   10

<210> SEQ ID NO 324
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Tyr Pro His Tyr Tyr Val Asn Glu Arg Lys Ser His Trp Tyr Phe Asp
1               5                   10                  15

Val

<210> SEQ ID NO 325
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 325

Tyr Pro Tyr Tyr Tyr Gly Thr Ser His Trp Tyr Phe Asp Val
1               5                   10

<210> SEQ ID NO 326
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Tyr Pro Tyr Tyr Tyr Gly Thr Ser His Trp Tyr Phe Asp Val
1               5                   10

<210> SEQ ID NO 327
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Tyr Pro His Tyr Tyr Gly Ser Ser His Trp Tyr Phe Asp Ala
1               5                   10

<210> SEQ ID NO 328
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Tyr Pro His Tyr Tyr Gly Ser Ser His Trp Tyr Phe Asp Tyr
1               5                   10

<210> SEQ ID NO 329
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Tyr Pro His Tyr Tyr Gly Ser Ser His Trp Tyr Phe Ala Val
1               5                   10

<210> SEQ ID NO 330
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Tyr Pro His Tyr Tyr Gly Ser Ser His Trp Tyr Ala Asp Val
1               5                   10

<210> SEQ ID NO 331

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Tyr Pro His Tyr Tyr Gly Ser Ser His Trp Ala Phe Asp Val
1               5                   10

<210> SEQ ID NO 332
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Tyr Pro His Tyr Tyr Gly Ser Ser His Ala Tyr Phe Asp Val
1               5                   10

<210> SEQ ID NO 333
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Tyr Pro His Tyr Tyr Gly Ser Ser Ala Trp Tyr Phe Asp Val
1               5                   10

<210> SEQ ID NO 334
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Tyr Pro His Tyr Tyr Gly Ser Ala His Trp Tyr Phe Asp Val
1               5                   10

<210> SEQ ID NO 335
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Tyr Pro Tyr Tyr Arg Gln Lys Gly His Trp Tyr Phe Asp Val
1               5                   10

<210> SEQ ID NO 336
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336
```

Tyr Pro Tyr Tyr Arg Gln Arg Gly His Trp Tyr Phe Asp Val
1               5                   10

<210> SEQ ID NO 337
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Tyr Pro Tyr Tyr Arg Asp Ala Ser His Trp Tyr Phe Asp Val
1               5                   10

<210> SEQ ID NO 338
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Tyr Pro Tyr Tyr Arg Asn Ala Ser His Trp Tyr Phe Asp Val
1               5                   10

<210> SEQ ID NO 339
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Tyr Pro Tyr Tyr Tyr Gly Ala Ser His Trp Tyr Phe Asp Val
1               5                   10

<210> SEQ ID NO 340
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Tyr Pro His Tyr Tyr Gly Ala Ser His Trp Tyr Phe Asp Val
1               5                   10

<210> SEQ ID NO 341
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Tyr Pro Tyr Tyr Arg Gly Glu Ser His Trp Tyr Phe Asp Val
1               5                   10

<210> SEQ ID NO 342
<211> LENGTH: 14
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 342

Tyr Pro Tyr Tyr Arg Lys Gly Ser His Trp Tyr Phe Asp Val
1               5                   10

<210> SEQ ID NO 343
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Tyr Pro Tyr Tyr Arg Ser Gly Ser His Trp Tyr Phe Asp Val
1               5                   10

<210> SEQ ID NO 344
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Tyr Pro Tyr Tyr Lys Gly Gly Ser His Trp Tyr Phe Asp Val
1               5                   10

<210> SEQ ID NO 345
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Tyr Pro Tyr Tyr Ile Ala Lys Ser His Trp Tyr Phe Asp Val
1               5                   10

<210> SEQ ID NO 346
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Tyr Pro Tyr Tyr Ile Asn Lys Ser His Trp Tyr Phe Asp Val
1               5                   10

<210> SEQ ID NO 347
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Tyr Pro Tyr Tyr Arg Asp Asn Ser His Trp Tyr Phe Asp Val
1               5                   10
```

```
<210> SEQ ID NO 348
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Tyr Pro Tyr Tyr Arg Gln Asn Ser His Trp Tyr Phe Asp Val
1               5                   10

<210> SEQ ID NO 349
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Tyr Pro Tyr Tyr Tyr Asn Gln Ser His Trp Tyr Phe Asp Val
1               5                   10

<210> SEQ ID NO 350
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Tyr Pro Tyr Tyr Ile Glu Arg Ser His Trp Tyr Phe Asp Val
1               5                   10

<210> SEQ ID NO 351
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Tyr Pro Tyr Tyr Thr Asn Arg Ser His Trp Tyr Phe Asp Val
1               5                   10

<210> SEQ ID NO 352
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Tyr Pro Tyr Tyr Thr Thr Arg Ser His Trp Tyr Phe Asp Val
1               5                   10

<210> SEQ ID NO 353
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353
```

Tyr Pro Tyr Tyr Thr Gly Arg Ser His Trp Tyr Phe Asp Val
1               5                   10

<210> SEQ ID NO 354
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Tyr Pro Tyr Tyr Lys Asn Thr Ser His Trp Tyr Phe Asp Val
1               5                   10

<210> SEQ ID NO 355
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Tyr Pro Tyr Tyr Arg Asn Thr Ser His Trp Tyr Phe Asp Val
1               5                   10

<210> SEQ ID NO 356
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Tyr Pro Tyr Tyr Thr Asn Thr Ser His Trp Tyr Phe Asp Val
1               5                   10

<210> SEQ ID NO 357
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Tyr Pro Tyr Tyr Arg Gly Thr Ser His Trp Tyr Phe Asp Val
1               5                   10

<210> SEQ ID NO 358
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Tyr Pro Tyr Tyr Trp Gly Thr Ser His Trp Tyr Phe Asp Val
1               5                   10

<210> SEQ ID NO 359
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 359

Tyr Pro Tyr Tyr Tyr Gly Thr Ser His Trp Tyr Phe Asp Val
1               5                   10

<210> SEQ ID NO 360
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Tyr Pro His Tyr Tyr Ala Ser Ser His Trp Tyr Phe Asp Val
1               5                   10

<210> SEQ ID NO 361
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Tyr Pro Tyr Tyr Lys Glu Ser Ser His Trp Tyr Phe Asp Val
1               5                   10

<210> SEQ ID NO 362
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Tyr Pro Tyr Tyr Arg Asn Ser Ser His Trp Tyr Phe Asp Val
1               5                   10

<210> SEQ ID NO 363
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Tyr Pro Tyr Tyr Arg Gln Ser Ser His Trp Tyr Phe Asp Val
1               5                   10

<210> SEQ ID NO 364
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Tyr Pro His Tyr Ala Gly Ser Ser His Trp Tyr Phe Asp Val
1               5                   10
```

<210> SEQ ID NO 365
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Tyr Pro Tyr Tyr Glu Gly Ser Ser His Trp Tyr Phe Asp Val
1               5                   10

<210> SEQ ID NO 366
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Tyr Pro Tyr Tyr Thr Gly Ser Ser His Trp Tyr Phe Asp Val
1               5                   10

<210> SEQ ID NO 367
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Tyr Pro His Ala Tyr Gly Ser Ser His Trp Tyr Phe Asp Val
1               5                   10

<210> SEQ ID NO 368
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Tyr Pro Ala Tyr Tyr Gly Ser Ser His Trp Tyr Phe Asp Val
1               5                   10

<210> SEQ ID NO 369
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Tyr Pro Tyr Tyr Tyr Gly Ser Ser His Trp Tyr Phe Asp Val
1               5                   10

<210> SEQ ID NO 370
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 370

Ala Ala His Tyr Tyr Gly Ser Ser His Trp Tyr Phe Asp Val
1               5                   10

<210> SEQ ID NO 371
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Ala Pro His Tyr Tyr Gly Ser Ser His Trp Tyr Phe Asp Val
1               5                   10

<210> SEQ ID NO 372
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Ala Ala Ser Gln Asp Ile Ser Asn Tyr Leu Asn
1               5                   10

<210> SEQ ID NO 373
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Ser Ala Ser Gln Asp Ile Ser Asn Tyr Leu Asn
1               5                   10

<210> SEQ ID NO 374
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Ser Ala Ala Gln Asp Ile Ser Asn Tyr Leu Asn
1               5                   10

<210> SEQ ID NO 375
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Ser Ala Ser Ala Asp Ile Ser Asn Tyr Leu Asn
1               5                   10

<210> SEQ ID NO 376
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 376

Ser Ala Ser Gln Ala Ile Ser Asn Tyr Leu Asn
1               5                   10

<210> SEQ ID NO 377
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Ser Ala Ser Gln Asp Ala Ser Asn Tyr Leu Asn
1               5                   10

<210> SEQ ID NO 378
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Ser Ala Ser Gln Asp Ile Ala Asn Tyr Leu Asn
1               5                   10

<210> SEQ ID NO 379
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Ser Ala Ser Gln Asp Ile Ser Ala Tyr Leu Asn
1               5                   10

<210> SEQ ID NO 380
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Ser Ala Ser Gln Asp Ile Ser Asn Ala Leu Asn
1               5                   10

<210> SEQ ID NO 381
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Ser Ala Ser Gln Asp Ile Ser Asn Tyr Ala Asn
1               5                   10
```

```
<210> SEQ ID NO 382
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Ser Ala Ser Gln Asp Ile Ser Asn Tyr Leu Ala
1               5                   10

<210> SEQ ID NO 383
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Arg Ala Asn Glu Gln Leu Ser Asn Tyr Leu Asn
1               5                   10

<210> SEQ ID NO 384
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Arg Ala Asn Glu Gln Ile Ser Asn Tyr Leu Asn
1               5                   10

<210> SEQ ID NO 385
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Arg Ala Ser Gln Ser Ile Ser Asn Tyr Leu Ala
1               5                   10

<210> SEQ ID NO 386
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Ala Thr Ser Ser Leu His Ser
1               5

<210> SEQ ID NO 387
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 387

Phe Ala Ser Ser Leu His Ser
1               5

<210> SEQ ID NO 388
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Phe Thr Ala Ser Leu His Ser
1               5

<210> SEQ ID NO 389
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Phe Thr Ser Ala Leu His Ser
1               5

<210> SEQ ID NO 390
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Phe Thr Ser Ser Ala His Ser
1               5

<210> SEQ ID NO 391
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Phe Thr Ser Ser Leu Ala Ser
1               5

<210> SEQ ID NO 392
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Phe Thr Ser Ser Leu His Ala
1               5

<210> SEQ ID NO 393
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Ala Ala Ser Ser Leu Glu Ser
1               5

<210> SEQ ID NO 394
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Gln Gln Tyr Ser Thr Val Phe Trp Thr
1               5

<210> SEQ ID NO 395
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Gln Gln Tyr Asn Ser Thr Pro Trp Thr
1               5

<210> SEQ ID NO 396
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Gln Gln Tyr Tyr Ser Thr Pro Trp Thr
1               5

<210> SEQ ID NO 397
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Gln Gln Ser Tyr Ser Thr Pro Trp Thr
1               5

<210> SEQ ID NO 398
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Gln Gln Tyr Ser Ala Val Pro Trp Thr
```

```
1               5

<210> SEQ ID NO 399
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Gln Gln Tyr Ser Asn Val Pro Trp Thr
1               5

<210> SEQ ID NO 400
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Gln Gln Tyr Ser Ser Val Pro Trp Thr
1               5

<210> SEQ ID NO 401
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Ala Gln Tyr Ser Thr Val Pro Trp Thr
1               5

<210> SEQ ID NO 402
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Gln Ala Tyr Ser Thr Val Pro Trp Thr
1               5

<210> SEQ ID NO 403
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Gln Gln Ala Ser Thr Val Pro Trp Thr
1               5

<210> SEQ ID NO 404
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                          peptide

<400> SEQUENCE: 404

Gln Gln Tyr Ala Thr Val Pro Trp Thr
1               5

<210> SEQ ID NO 405
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Gln Gln Tyr Ser Ala Val Pro Trp Thr
1               5

<210> SEQ ID NO 406
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Gln Gln Tyr Ser Thr Ala Pro Trp Thr
1               5

<210> SEQ ID NO 407
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Gln Gln Tyr Ser Thr Val Ala Trp Thr
1               5

<210> SEQ ID NO 408
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Gln Gln Tyr Ser Thr Val Pro Ala Thr
1               5

<210> SEQ ID NO 409
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Gln Gln Tyr Ser Thr Val Pro Trp Ala
1               5

<210> SEQ ID NO 410
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Gln Gln Tyr Asn Ser Leu Pro Trp Thr
1               5

<210> SEQ ID NO 411
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Gly Tyr Thr Phe Thr Asn Tyr Gly Met
1               5

<210> SEQ ID NO 412
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Gly Gly Gly Gly Ser Gly Gly Gly Gly Ser Gly Gly Gly Gly Ser
1               5                   10                  15
```

ANTI-VEGF ANTIBODIES AND THEIR USES

1. CROSS-REFERENCE TO RELATED APPLICATIONS AND SEQUENCE LISTING

This application claims the benefit under 35 U.S.C. §119 (e) of U.S. provisional application No. 61/218,005, filed Jun. 17, 2009, the contents of which are incorporated herein by reference in their entireties.

The instant application contains a Sequence Listing which has been submitted via EFS-Web and is hereby incorporated by reference in its entirety. Said ASCII copy, created on Jun. 15, 2010, is named 381493US.txt and is 132,486 bytes in size.

2. FIELD OF THE INVENTION

The present invention relates to anti-VEGF antibodies, pharmaceutical compositions comprising anti-VEGF antibodies, and therapeutic uses of such antibodies.

3. BACKGROUND

Angiogenesis has emerged as attractive therapeutic target due to its implication in a variety of pathological conditions, including tumor growth, proliferative retinopathies, age-related macular degeneration, rheumatoid arthritis (RA), and psoriasis (Folkman et al., 1992, J. Biol. Chem. 267:10931-10934). The first indication of specific molecular angiogenic factors was based on the observation of the strong neovascular response induced by transplanted tumors. It is now known that angiogenesis is essential for the growth of most primary tumors and their subsequent metastasis. Numerous molecules have since been associated with the positive regulation of angiogenesis, including transforming growth factor (TGF)-α, TGF-β, hepatocyte growth factor (HGF), tumor necrosis factor-α, angiogenin, interleukin (IL)-8, and vascular endothelial growth factor (VEGF, also referred to as VEGFA or vascular permeability factor (VPF)) (Ferrara et al., 2003, Nature Medicine 9:669-676).

The VEGF proteins are important signaling proteins involved in both normal embryonic vasculogenesis (the de novo formation of the embryonic circulatory system) and abnormal angiogenesis (the growth of blood vessels from pre-existing vasculature) (Ferrara et al., 1996, Nature 380: 439-442; Dvorak et al., 1995, Am. J. Pathol. 146:1029-1039). VEGF is associated with solid tumors and hematologic malignancies, interocular neovascular syndromes, inflammation and brain edema, and pathology of the female reproductive tract (Ferrara et al., 2003, Nature Medicine 9:669-676). VEGF mRNA is over-expressed in many human tumors, including those of the lung, breast, gastrointestinal tract, kidney, pancreas, and ovary (Berkman et al., 1993, J. Clin. Invest. 91:153-159). Increases in VEGF in the aqueous and vitreous humor of the eyes have been associated with various retinopathies (Aiello et al., 1994, N. Engl. J. Med. 331:1480-1487). Age-related macular degeneration (AMD), a major cause of vision loss in the elderly is due to neovascularization and vascular leakage. The localization of VEGF in the choroidal neovascular membranes in patients affected by AMD has been shown (Lopez et al., 1996, Invest. Ophtalmo. Vis. Sci. 37:855-868).

The VEGF gene family includes the prototypical member VEGFA, as well as VEGFB, VEGFC, VEGFD, and placental growth factor (PLGF). The human VEGFA gene is organized as eight exons separated by seven introns. At least six different isoforms of VEGF exist, $VEGF_{121}$, $VEGF_{145}$, $VEGF_{162}$, $VEGF_{165}$, $VEGF_{165b}$, $VEGF_{183}$, $VEGF_{189}$, and $VEGF_{206}$; where the subscripts refer to the number of amino acids remaining after signal cleavage. Native VEGF is a 45 kDa homodimeric heparin-binding glycoprotein (Ferrara et al., 2003, Nature Medicine 9:669-676). VEGF (specifically VEGFA) binds to two related receptor tyrosine kinases, VEGFR-1 (also referred to as Flt-1) and VEGFR-2 (also referred to as Flk-1 or kinase domain region (KDR) or CD309). Each receptor has seven extracellular and one transmembrane region. VEGF also binds to the neuropilins NRP1 (also referred to as vascular endothelial cell growth factor 165 receptor (VEGF165R) or CD304) and NRP2 also referred to as vascular endothelial cell growth factor 165 receptor 2 (VEGF165R2)).

Given its central role in regulating angiogenesis, VEGF provides an attractive target for therapeutic intervention. Indeed, a variety of therapeutic strategies aimed at blocking VEGF or its receptor signaling system are currently being developed for the treatment of neoplastic diseases. The anti-VEGF antibody bevacizumab, also referred to as rhuMAb VEGF or Avastin®, is a recombinant humanized anti-VEGF monoclonal antibody created and marketed by Genentech (Presta et al., 1997, Cancer Res. 57:4593-4599). In order to construct bevacizumab the complementarity-determining regions (CDRs) of the murine anti-VEGF monoclonal antibody A.4.6.1 were grafted onto human frameworks and an IgG constant region. Additional mutations outside the CDRs were then introduced into the molecule to improve binding, affording an antibody in which ~93% of the amino acid sequence is derived from human $IgG_1$ and ~7% of the sequence is derived from the murine antibody A.4.6.1. Bevacizumab has a molecular mass of about 149,000 Daltons and is glycosylated.

Ranibizumab is an affinity matured Fab fragment derived from bevacizumab. Ranibizumab has a higher affinity for VEGF and also is smaller in size, allowing it to better penetrate the retina, and thus treat the ocular neovascularization associated with AMD (Lien and Lowman, In: Chemajovsky, 2008, Therapeutic Antibodies. Handbook of Experimental Pharmacology 181, Springer-Verlag, Berlin Heidelberg 131-150). Ranibizumab was developed and is marketed by Genentech under the trade name Lucentis®.

Treatment of cancer patients with a regimen that includes Avastin® can result in side effects including hypertension, proteinuria, thromboembolic events, bleeding and cardiac toxicity (Blowers & Hall, 2009, Br. J. Nurs. 18(6):351-6, 358). Also, despite being a humanized antibody, bevacizumab can elicit an immune response when administered to humans. Such an immune response may result in an immune complex-mediated clearance of the antibodies or fragments from the circulation, and make repeated administration unsuitable for therapy, thereby reducing the therapeutic benefit to the patient and limiting the re-administration of the antibody.

Accordingly, there is a need to provide improved anti-VEGF antibodies or fragments that overcome one or more of these problems, for example, by generating variants with higher affinity than bevacizumab that can be administered at reduced dosages, or variants with reduced immunogenicity and other side-effects as compared to bevacizumab.

Citation or identification of any reference in Section 3 or in any other section of this application shall not be construed as an admission that such reference is available as prior art to the present disclosure.

4. SUMMARY

The present disclosure relates to variants of the anti-VEGF antibody bevacizumab with reduced immunogenicity and/or improved affinity towards VEGF as compared to bevacizumab or ranibizumab. Bevacizumab has three heavy chain CDRs, referred to herein (in amino- to carboxy-terminal order) as CDR-H1, CDR-H2, and CDR-H3, and three light chain CDRs, referred to herein (in amino- to carboxy-terminal order) as CDR-L1, CDR-L2, and CDR-L3. The sequences of the bevacizumab CDRs are shown in FIGS. 1A and 1B, and their numbering is set forth in FIG. 5 (for heavy chain CDRs) and FIG. 6 (for light chain CDRs). A related antibody, ranibizumab, was generated by affinity maturation of bevacizumab. Ranibizumab has identical CDR-L1, CDR-L2, CDR-L3 and CDR-H2 sequences to bevacizumab, but varies in its CDR-H1 and CDR-H3 sequences from those of bevacizumab. The heavy and light chain sequences of ranibizumab are shown in FIG. 1C, and the CDRs are set forth in FIG. 1D.

The antibodies of the disclosure generally have at least one amino acid substitution in at least one heavy chain CDR as compared to bevacizumab and ranibizumab.

In certain aspects, the anti-VEGF antibodies include at least one substitution as compared to bevacizumab or ranibizumab selected from N31F in CDR-H1; K64S in CDR-H2; K64Q in CDR-H2; Y53F in CDR-H2; H97E in CDR-H3; H97D in CDR-H3; H97P in CDR-H3; Y98F in CDR-H3; Y99E in CDR-H3; Y99D in CDR-H3; S100aG in CDR-H3, and T51A in CDR-L2. In other aspects, the anti-VEGF antibodies include at least one substitution selected from FIGS. 12 and 13. Additional mutations that can be incorporated into the improved affinity variant antibodies can be candidate deimmunizing substitutions, such as those described in FIG. 10, as well as other mutations, e.g., substitutions, that do not destroy the ability of the antibodies to bind to VEGF, including but not limited to the mutations described in FIGS. 14 and 15, or known mutations, such as the mutations described in FIGS. 16A-16I and 17. Yet further mutations that can be incorporated include but are not limited to the mutations described in FIGS. 18-20.

In specific embodiments, the anti-VEGF antibodies of the disclosure include a combination of substitutions selected from FIG. 11, and optionally one or more additional mutations, e.g., candidate deimmunizing substitutions, such as those described in FIG. 10, as well as other mutations, e.g., substitutions, that do not destroy the ability of the antibodies to bind to VEGF, including but not limited to the mutations described in FIGS. 14 and 15, or known mutations, such as the mutations described in FIGS. 16A-16I and 17. Yet further mutations that can be incorporated into the anti-VEGF antibodies of the disclosure include but are not limited to the mutations described in FIGS. 18-20.

In other embodiments, the anti-VEGF antibodies of the disclosure include one or more of the following CDR substitutions: K64S (CDR-H2), K64Q (CDR-H2), Y53F and K64Q (CDR-H2), H97E and Y98F (CDR-H3), or T51A (CDR-L2). The anti-VEGF antibodies can also optionally include one or more additional mutations or combinations of mutations selected from one or more of FIGS. 10, 11, 12, 13, 14, 15, 16A to 16I, or 17-20.

Further CDR substitutions can include N31F (CDR-H1), H97E (CDR-H3), H97D (CDR-H3), H97P (CDR-H3), Y99E (CDR-H3), Y99D (CDR-H3), S100aG (CDR-H3) wherein position 3 in CDR-H3 optionally is not tyrosine, T28P, N31F, N31G and N31M (CDR-H1), H97A, H97Q, H97S, H97T, S100aD, S100aE, and S100Av (CDR-H3), T30W, T30R or T30Q (CDR-H1), Y53F, T58F, A61G, A61K, A61R, A61H, A61Y, K64G, K64E, R65L, R65T, R65A, R65E, and R65D (CDR-H2), and Y98F and Y100eF (CDR-H3). The CDRs optionally contain one or more additional mutations or combinations of mutations selected from one or more of FIGS. 10, 11, 12, 13, 14, 15, 16A to 16I, and 17.

Yet further substitutions can include heavy chain CDR substitutions including a combination of substitutions selected from: (a) N31F in CDR-H1, H97D in CDR-H3, Y99D in CDR-H3, and S100aG in CDR-H3; (b) N31F in CDR-H1, H97P in CDR-H3, Y99D in CDR-H3, and S100aG in CDR-H3; (c) N31F in CDR-H1, H97P in CDR-H3, and Y99E in CDR-H3; (d) N31F in CDR-H1, H97E in CDR-H3, and Y99E in CDR-H3; (e) N31F in CDR-H1, H97D in CDR-H3, and Y99E in CDR-H3; (f) N31F in CDR-H1, H97E in CDR-H3, Y99D in CDR-H3, and S100aG in CDR-H3; (g) N31F in CDR-H1, Y99D in CDR-H3, and S100aG in CDR-H3; (h) N31F in CDR-H1, H97P in CDR-H3, and Y99D in CDR-H3; (i) N31F in CDR-H1, H97D in CDR-H3, and S100aG in CDR-H3; (j) N31F in CDR-H1 and S100aG in CDR-H3; or (k) N31F in CDR-H1, H97P in CDR-H3, and S100aG in CDR-H3. Further optional substitutions can include one or more additional mutations or combinations of mutations selected from one or more of FIGS. 11, 12, 13, 14, 15, 16A to 16I, and 17.

Still further heavy chain substitutions can include at least one substitution selected from A61F in CDR-H2, A61E in CDR-H2, A61D in CDR-H2, D62L in CDR-H2, D62G in CDR-H2, D62Q in CDR-H2, D62T in CDR-H2, D62K in CDR-H2, D62R in CDR-H2, D62E in CDR-H2, D62H in CDR-H2, K64S in CDR-H2, K64V in CDR-H2, K64Q in CDR-H2, R65V in CDR-H2, R65F in CDR-H2, R65H in CDR-H2, R65N in CDR-H2, R65S in CDR-H2, R65Q in CDR-H2, R65K in CDR-H2, R65I in CDR-H2, and Y98H in CDR-H3. Optionally, one or more additional mutations or combinations of mutations can be included as selected from one or more of FIGS. 11, 12, 13, 14, 15, 16A to 16I, and 17.

In certain aspects, the antibodies of the disclosure have VH and VL sequences having at least 80% sequence identity (and in certain embodiments, at least 85%, at least 90%, at least 95%, at least 98%, or at least 99% sequence identity) to the VH and VL sequences of bevacizumab or ranibizumab, and include at least one amino acid substitution in at least one CDR as compared to bevacizumab or ranibizumab. In other aspects, the antibodies of the disclosure have VH and VL sequences having at least 80% sequence identity (and in certain embodiments, at least 85%, at least 90%, at least 95%, at least 98%, or at least 99% sequence identity) to the VH and VL sequences of bevacizumab or ranibizumab, and include at least one amino acid substitution in at least one framework region as compared to bevacizumab or ranibizumab. In specific embodiments, the percentage sequence identity for the heavy chain and the light chain compared to the VH and VL sequences of bevacizumab or ranibizumab is independently selected from at least 80%, at least 85%, at least 90%, at least 95% sequence identity, or at least 99% sequence identity. In certain aspects, the antibodies of the disclosure have VH and/or VL sequences having at least 95%, at least 98% or at least 99% sequence identity to the VH and/or VL sequences of bevacizumab or ranibizumab.

In certain aspects, the antibodies of the disclosure have up to 17 amino acid substitutions in their CDRs as compared to bevacizumab or ranibizumab. Variant antibodies with 17 amino acid substitutions that maintain their target binding capability have been generated by Bostrom et al., 2009, Science 323:1610-14.

In specific embodiments, an anti-VEGF antibody of the disclosure has, independently:

up to one, up to two, up to three, up to four, up to five, up to six, up to seven, up to eight, up to nine or up to ten CDR-H1 substitutions as compared to the corresponding CDR of bevacizumab or of ranibizumab;

up to one, up to two, up to three, up to four, up to five, up to six, up to seven, up to eight, up to nine, up to ten, up to eleven, up to twelve, up to thirteen, up to fourteen, up to fifteen, up to sixteen or up to seventeen CDR-H2 substitutions as compared to the corresponding CDR of bevacizumab or of ranibizumab;

up to one, up to two, up to three, up to four, up to five, up to six, up to seven, up to eight, up to nine, up to ten, up to eleven, up to twelve, up to thirteen or up to fourteen CDR-H3 substitutions as compared to the corresponding CDR of bevacizumab or of ranibizumab;

up to one, up to two, up to three, up to four, up to five, up to six, up to seven, up to eight, up to nine, up to ten or up to eleven CDR-L1 substitutions as compared to the corresponding CDR of bevacizumab or of ranibizumab;

up to one, up to two, up to three, up to four, up to five, up to six or up to seven CDR-L2 substitutions as compared to the corresponding CDR of bevacizumab or of ranibizumab; and up to one, up to two, up to three, up to four, up to five, up to six, up to seven, up to eight or up to nine CDR-L3 substitutions as compared to the corresponding CDR of bevacizumab or of ranibizumab.

The present disclosure further provides pharmaceutical compositions comprising modified anti-VEGF antibodies. In some aspects, the pharmaceutical compositions have increased affinity to VEGF and/or reduced immunogenicity as compared to bevacizumab or ranibizumab.

Nucleic acids comprising nucleotide sequences encoding the anti-VEGF antibodies of the disclosure are provided herein, as are vectors comprising the nucleic acids. Additionally, prokaryotic and eukaryotic host cells transformed with a vector comprising a nucleotide sequence encoding an anti-VEGF antibody are provided herein, as well as eukaryotic (such as mammalian) host cells engineered to express the nucleotide sequences. Methods of producing anti-VEGF antibodies by culturing host cells are also provided.

The anti-VEGF antibodies of the disclosure are useful in the treatment of cancers (e.g., colon carcinoma, rectal carcinoma, non-small cell lung cancer, and breast cancer), retinal diseases (e.g., age-related macular degeneration ("AMD")), and immune disorders (e.g., rheumatoid arthritis).

In certain aspects, the anti-VEGF antibodies of the disclosure can be used in reduced dosages as compared to bevacizumab or ranibizumab, e.g., at least 10%, at least 20%, at least 30%, at least 40%, at least 50%, at least 60%, at least 70%, at least 80% or at least 90% lower dosages.

It should be noted that the indefinite articles "a" and "an" and the definite article "the" are used in the present application, as is common in patent applications, to mean one or more unless the context clearly dictates otherwise. Further, the term "or" is used in the present application, as is common in patent applications, to mean the disjunctive "or" or the conjunctive "and."

All publications mentioned in this specification are herein incorporated by reference. Any discussion of documents, acts, materials, devices, articles or the like that has been included in this specification is solely for the purpose of providing a context for the present disclosure. It is not to be taken as an admission that any or all of these matters form part of the prior art base or were common general knowledge in the field relevant to the present disclosure as it existed anywhere before the priority date of this application.

The features and advantages of the disclosure will become further apparent from the following detailed description of embodiments thereof.

5. BRIEF DESCRIPTION OF THE TABLES AND FIGURES

FIGS. 1A-1D. FIG. 1A shows the amino acid sequences of the bevacizumab heavy and light chain variable regions, SEQ ID NO:1 and SEQ ID NO:2, respectively, with CDR regions in bold, underlined text. FIG. 1B shows the CDR sequences and corresponding sequence identifiers of bevacizumab. FIG. 1C shows the amino acid sequences of the ranibizumab heavy and light chains, SEQ ID NO:9 and SEQ ID NO:10, respectively, with CDR regions in bold, underlined text. FIG. 1D shows the CDR sequences and corresponding sequence identifiers of ranibizumab.

FIGS. 2A-2B show bevacizumab VL peptide responses. FIG. 2A shows percent of donor responses to each VL peptide with a stimulation index of 2.95 or greater. N=99 donors. FIG. 2B shows the average stimulation index for all 99 donors for each peptide plus or minus standard error.

FIGS. 3A-3B show bevacizumab VH peptide responses. FIG. 3A shows percent of donor responses to each VH peptide with a stimulation index of 2.95 or greater. N=99 donors. FIG. 3B shows the average stimulation index for all 99 donors for each peptide plus or minus standard error.

FIGS. 4A-4C show CD4+ T cell responses to mutant bevacizumab epitope peptides. Average responses to the unmodified parent epitope sequences are indicated with open marks. Large circles indicate selected changes referred to in FIG. 21. FIG. 4A is directed to VH CDR2 peptides; FIG. 4B is directed to VH CDR3 peptides; and FIG. 4C is directed to VL CDR2 peptides.

FIG. 5 shows the numbering of the amino acids in the heavy chain CDRs of bevacizumab. CDRs 1-3 are disclosed as SEQ ID NOS:3-5, respectively.

FIG. 6 shows the numbering of the amino acids in the light chain CDRs of bevacizumab. CDRs 1-3 are disclosed as SEQ ID NOS:6-8, respectively.

FIG. 7 shows bevacizumab VL peptides that were tested for immunogenicity.

FIG. 8 shows bevacizumab VH peptides that were tested for immunogenicity.

FIG. 9 shows identified CD4+ T cell epitope regions in bevacizumab. CDR regions are underlined.

FIG. 10 shows candidate mutations in CDR-H2 and CDR-H3 for lowering immunogenicity of bevacizumab. The numbering of the amino acids in FIG. 10 corresponds to Kabat numbering in the bevacizumab heavy chain.

Figures 2A, 2B:
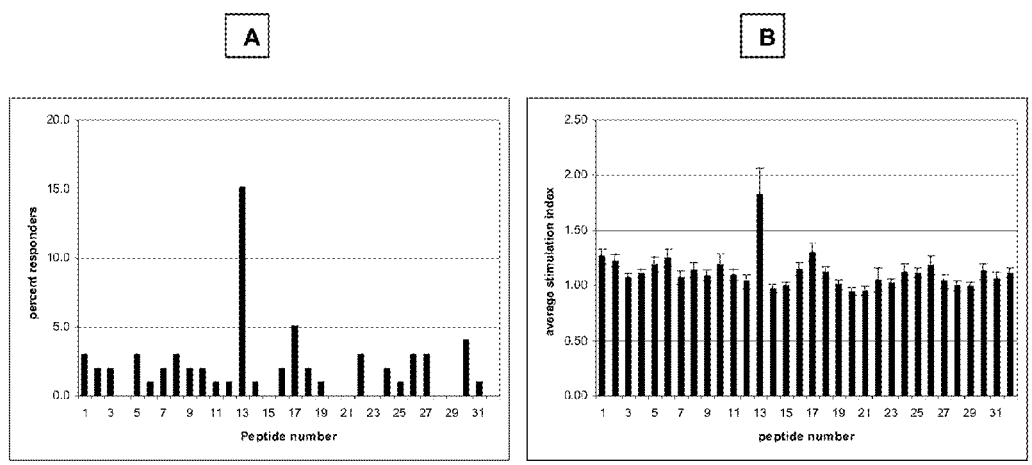

FIG. 11 shows heavy chain CDR amino acid substitutions in bevacizumab resulting improved $K_D$ as analyzed by surface plasmon resonace. $\Delta k_{on}$ refers to fold improvement in $k_{on}$ (mutant/WT). $\Delta k_{off}$ refers to fold improvement in $k_{off}$ (WT/mutant). $\Delta K_D$ refers to the improvement in the $K_D$ in the mutant relative to wild type. The numbering of the amino acids in FIG. 11 corresponds to Kabat numbering in the bevacizumab heavy chain.

FIG. 12 shows mutations in the bevacizumab heavy chain CDRs that preliminary binding studies indicate increase the affinity towards VEGF (data not shown). The numbering of the amino acids in FIG. 12 corresponds to Kabat numbering in the bevacizumab heavy chain.

FIG. 13 shows mutations in the bevacizumab heavy chain CDRs that preliminary studies indicate increase the affinity towards VEGF (data not shown). The numbering of the amino acids in FIG. 13 corresponds to Kabat numbering in the bevacizumab heavy chain.

FIG. 14 shows mutations in the bevacizumab heavy chain CDRs that do not impact binding and can be incorporated into the antibodies of the disclosure. The numbering of the amino acids in FIG. 14 corresponds to Kabat numbering in the bevacizumab heavy chain.

FIG. 15 shows mutations in the bevacizumab light chain CDRs that do not impact binding and can be incorporated into the antibodies of the disclosure. The numbering of the amino acids in FIG. 15 corresponds to Kabat numbering in the bevacizumab light chain.

Figure 16A:
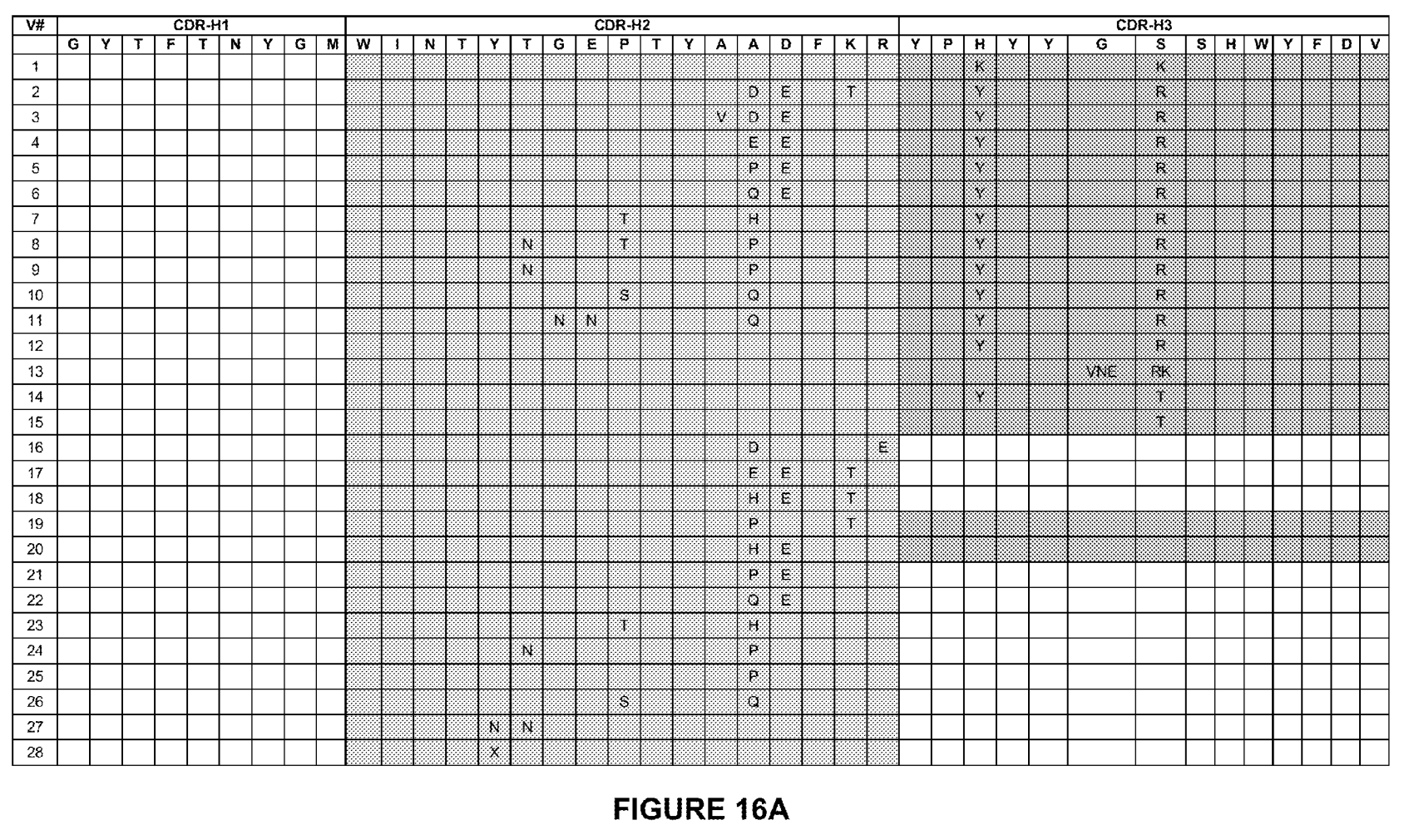
Figure 16I:
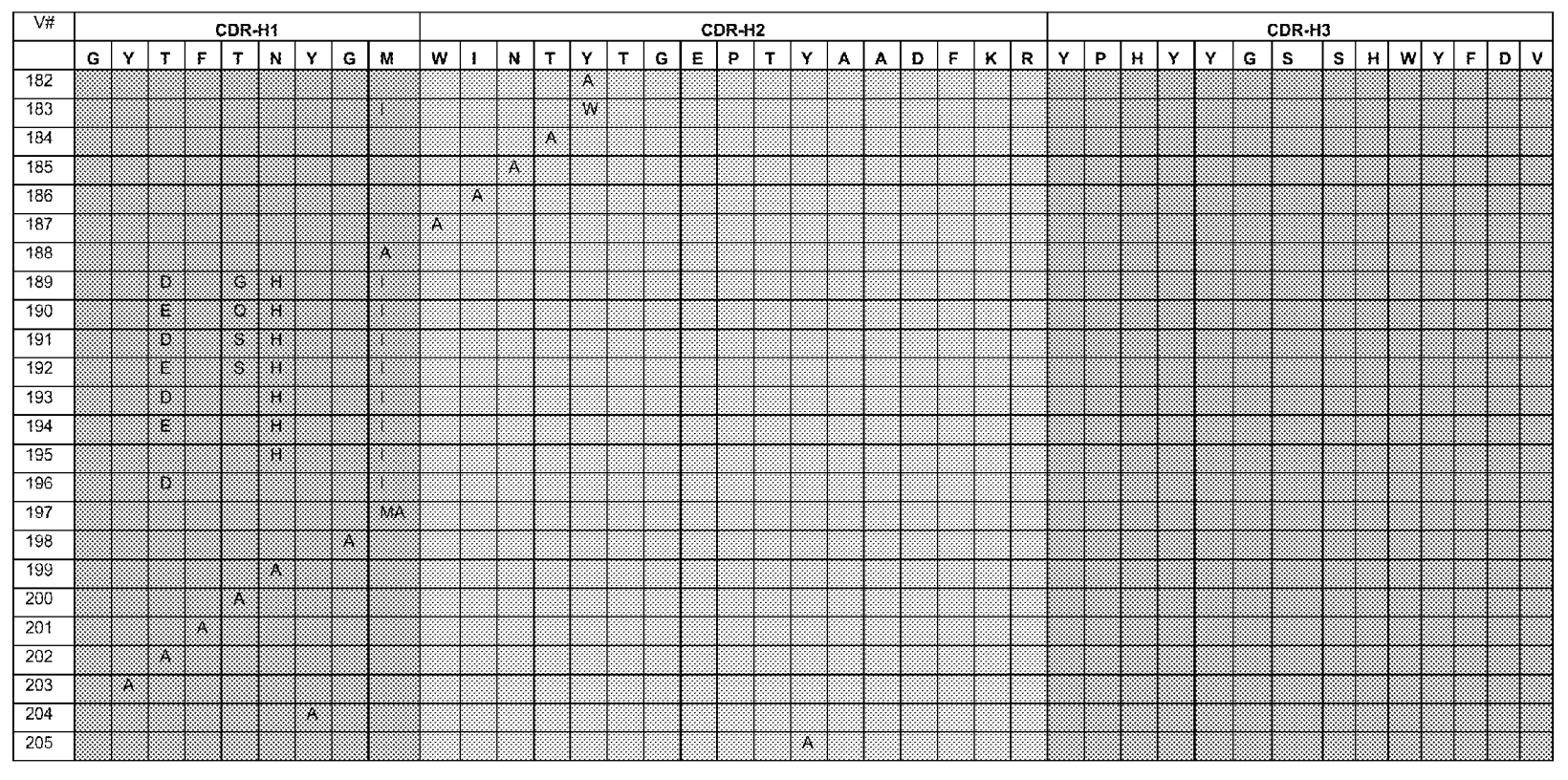

FIG. 16A-16I show known mutations in bevacizumab heavy chain CDRs that can be incorporated into the antibodies of the disclosure. Each row in FIGS. 16A-16I includes a distinct known variant. For each variant, the known CDR sequences are shaded. The sequence identifiers for each variant identified in FIGS. 16A-16I are set forth in FIGS. 24A-24I, respectively. The CDR-H1 is not shown. This partial sequence corresponds to SEQ ID NO:411. Although known mutations in CDR-H1 are shown in the context of this partial sequence, it is noted that the mutations exist in the context of the full length CDR.

FIG. 17 shows known mutations in bevacizumab light chain CDRs that can be incorporated into the antibodies of the disclosure. Each row in FIG. 17 includes a distinct known variant. For each variant, the known CDR sequences are shaded. The sequence identifiers for each variant identified in FIG. 17 is set forth in FIG. 24J.

FIG. 18 shows bevacizumab CDR2 VH peptides that were tested for immunogenicity, wherein residues unchanged from SEQ ID NO:62 are indicated by a blank box. CD4+ T cell assay results are also provided.

FIG. 19 shows bevacizumab CDR3 VH peptides that were tested for immunogenicity, wherein residues unchanged from SEQ ID NO:74 are indicated by a blank box. CD4+ T cell assay results are also provided.

FIG. 20 shows bevacizumab CDR2 VL peptides that were tested for immunogenicity, wherein residues unchanged from SEQ ID NO:25 are indicated by a blank box. CD4+ T cell assay results are also provided.

FIG. 21 shows selected epitope modifications for the three CD4+ T cell epitopes in bevacizumab.

FIG. 22 shows single variable region mutants and their associated mean fluorescence intensity (MFI) score.

FIG. 23 shows combined variable region mutants and their associated $EC_{50}$.

FIG. 24A-24J show the SEQ ID NOS, where known, corresponding to the CDRs of the bevacizumab variants listed in FIGS. 16A-16I and FIG. 17, respectively, N/A indicates an unknown CDR sequence.

6. DETAILED DESCRIPTION

6.1 Anti-VEGF Antibodies

The present disclosure provides anti-VEGF antibodies. Unless indicated otherwise, the term "antibody" (Ab) refers to an immunoglobulin molecule that specifically binds to, or is immunologically reactive with, a particular antigen, and includes polyclonal, monoclonal, genetically engineered and otherwise modified forms of antibodies, including but not limited to chimeric antibodies, humanized antibodies, heteroconjugate antibodies (e.g., bispecific antibodies, diabodies, triabodies, and tetrabodies), and antigen binding fragments of antibodies, including e.g., Fab', F(ab')$_2$, Fab, Fv, rIgG, and scFv fragments. Moreover, unless otherwise indicated, the term "monoclonal antibody" (mAb) is meant to include both intact molecules, as well as, antibody fragments (such as, for example, Fab and F(ab')$_2$ fragments) which are capable of specifically binding to a protein. Fab and F(ab')$_2$ fragments lack the Fc fragment of intact antibody, clear more rapidly from the circulation of the animal, and may have less non-specific tissue binding than an intact antibody (Wahl et al., 1983, J. Nucl. Med. 24:316).

The term "scFv" refers to a single chain Fv antibody in which the variable domains of the heavy chain and the light chain from a traditional antibody have been joined to form one chain.

References to "VH" refer to the variable region of an immunoglobulin heavy chain of an antibody, including the heavy chain of an Fv, scFv, or Fab. References to "VL" refer to the variable region of an immunoglobulin light chain, including the light chain of an Fv, scFv, dsFv or Fab. Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 Daltons, composed of two identical light (L) chains and two identical heavy (H) chains. Each heavy chain has at the amino terminus a variable domain (VH) followed by a number of constant domains. Each light chain has a variable domain at the amino terminus (VL) and a constant domain at the carboxy terminus.

The anti-VEGF antibodies of the disclosure bind to human VEGF and inhibit VEGF receptor activity in a cell.

The anti-VEGF antibodies of the disclosure contain complementarity determining regions (CDRs) that are related in sequence to the CDRs of the antibody bevacizumab (also known as Avastin®) and/or ranibizumab (also known as Lucentis®).

CDRs are also known as hypervariable regions both in the light chain and the heavy chain variable domains. The more highly conserved portions of variable domains are called the framework (FR). As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The disclosure provides antibodies comprising modifications in these hybrid hypervariable positions. The variable domains of native heavy and light chains each comprise four FR regions, largely by adopting a β-sheet configuration, connected by three CDRs, which form loops connecting, and in some cases forming part of, the β-sheet structure. The CDRs in each chain are held together in close proximity by the FR regions in the order FR1-CDR1-FR2-CDR2-FR3-CDR3-FR4 and, with the CDRs from the other chain, contribute to the formation of the target binding site of antibodies (see Kabat et al., Sequences of Proteins of Immunological Interest (National Institute of Health, Bethesda, Md. 1987). As used herein, numbering of immunoglobulin amino acid residues is done according to the immunoglobulin amino acid residue numbering system of Kabat et al., unless otherwise indicated.

The sequences of the heavy and light chain variable regions of bevacizumab are represented by SEQ ID NO:1 and SEQ ID NO:2, respectively. The sequences of the heavy and light chain variable regions are also depicted in FIG. 1A. The sequences of the CDRs of bevacizumab, and their corresponding identifiers, are presented in FIG. 1B. Any nucleotide sequences encoding SEQ ID NO:1 or SEQ ID NO:2 can be used in the compositions and methods of the present disclosure.

The sequences of the heavy and light chains of ranibizumab are represented by SEQ ID NO:9 and SEQ ID NO:10, respectively. The sequences of the heavy and light chains are also depicted in FIG. 1C. The sequences of the CDRs of ranibizumab, and their corresponding identifiers, are presented in FIG. 1D. Any nucleotide sequences encoding SEQ ID NO:9 or SEQ ID NO:10 can be used in the compositions and methods of the present disclosure.

The present disclosure further provides anti-VEGF antibody fragments comprising CDR sequences that are related to the CDR sequences of bevacizumab and ranibizumab. The term "antibody fragment" refers to a portion of a full-length antibody, generally the target binding or variable region. Examples of antibody fragments include Fab, Fab', F(ab')$_2$ and Fv fragments. An "Fv" fragment is the minimum antibody fragment which contains a complete target recognition and binding site. This region consists of a dimer of one heavy and one light chain variable domain in a tight, non-covalent association (VH-VL dimer). It is in this configuration that the three CDRs of each variable domain interact to define a target binding site on the surface of the VH-VL dimer. Often, the six CDRs confer target binding specificity to the antibody. However, in some instances even a single variable domain (or half of an Fv comprising only three CDRs specific for a target) can have the ability to recognize and bind target. "Single-chain Fv" or "scFv" antibody fragments comprise the VH and VL domains of an antibody in a single polypeptide chain. Generally, the Fv polypeptide further comprises a polypeptide linker between the VH and VL domain which enables the scFv to form the desired structure for target binding. "Single domain antibodies" are composed of a single VH or VL domains which exhibit sufficient affinity to the target. In a specific embodiment, the single domain antibody is a camelid antibody (see, e.g., Riechmann, 1999, Journal of Immunological Methods 231:25-38).

The Fab fragment contains the constant domain of the light chain and the first constant domain (CH$_1$) of the heavy chain. Fab' fragments differ from Fab fragments by the addition of a few residues at the carboxyl terminus of the heavy chain CH$_1$ domain including one or more cysteines from the antibody hinge region. F(ab') fragments are produced by cleavage of the disulfide bond at the hinge cysteines of the F(ab')$_2$ pepsin digestion product. Additional chemical couplings of antibody fragments are known to those of ordinary skill in the art.

In certain embodiments, the anti-VEGF antibodies of the disclosure are monoclonal antibodies. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies useful in connection with the present disclosure can be prepared using a wide variety of techniques known in the art including the use of hybridoma, recombinant, and phage display technologies, or a combination thereof. The anti-VEGF antibodies of the disclosure include chimeric, primatized, humanized, or human antibodies.

The anti-VEGF antibodies of the disclosure can be chimeric antibodies. The term "chimeric" antibody as used herein refers to an antibody having variable sequences derived from a non-human immunoglobulin, such as rat or mouse antibody, and human immunoglobulin constant regions, typically chosen from a human immunoglobulin template. Methods for producing chimeric antibodies are known in the art. See, e.g., Morrison, 1985, Science 229 (4719):1202-7; Oi et al., 1986, BioTechniques 4:214-221; Gillies et al., 1985, J. Immunol. Methods 125:191-202; U.S. Pat. Nos. 5,807,715; 4,816,567; and 4,816397, which are incorporated herein by reference in their entireties.

The anti-VEGF antibodies of the disclosure can be humanized. "Humanized" forms of non-human (e.g., murine) antibodies are chimeric immunoglobulins, immunoglobulin chains or fragments thereof (such as Fv, Fab, Fab', F(ab')$_2$ or other target-binding subdomains of antibodies) which contain minimal sequences derived from non-human immunoglobulin. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and 6,180,370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332, all of which are hereby incorporated by reference in their entireties.

The anti-VEGF antibodies of the disclosure can be human antibodies. Completely "human" anti-VEGF antibodies can be desirable for therapeutic treatment of human patients. As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins. Human antibodies can be made by a variety of methods known in the art including phage display methods using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety. Human antibodies can also be produced using transgenic mice which are incapable of expressing functional endogenous immunoglobulins, but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. In addition, companies such as Medarex (Princeton, N.J.), Astellas Pharma (Deerfield, Ill.), Amgen (Thousand Oaks, Calif.) and Regeneron (Tarrytown, N.Y.) can be engaged to provide human antibodies directed against a selected antigen using technology similar to that described above. Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., 1988, Biotechnology 12:899-903).

The anti-VEGF antibodies of the disclosure can be primatized. The term "primatized antibody" refers to an antibody comprising monkey variable regions and human constant regions. Methods for producing primatized antibodies are known in the art. See e.g., U.S. Pat. Nos. 5,658,570; 5,681,722; and 5,693,780, which are incorporated herein by reference in their entireties.

The anti-VEGF antibodies of the disclosure can be bispecific antibodies. Bispecific antibodies are monoclonal, often human or humanized, antibodies that have binding specificities for at least two different antigens. In the present disclosure, one of the binding specificities can be directed towards VEGF, the other can be for any other antigen, e.g., for a cell-surface protein, receptor, receptor subunit, tissue-specific antigen, virally derived protein, virally encoded envelope protein, bacterially derived protein, or bacterial surface protein, etc. In a specific embodiment, an antibody of the disclosure is a bispecific antibody with binding specificites for both VEGF and CD3.

The anti-VEGF antibodies of the disclosure include derivatized antibodies. For example, but not by way of limitation, derivatized antibodies are typically modified by glycosylation, acetylation, pegylation, phosphorylation, amidation, derivatization by known protecting/blocking groups, proteolytic cleavage, linkage to a cellular ligand or other protein (see Section 6.6 for a discussion of antibody conjugates), etc. Any of numerous chemical modifications can be carried out by known techniques, including, but not limited to, specific chemical cleavage, acetylation, formylation, metabolic synthesis of tunicamycin, etc. Additionally, the derivative can contain one or more non-natural amino acids, e.g., using ambrx technology (see, e.g., Wolfson, 2006, Chem. Biol. 13(10):1011-2).

In yet another embodiment of the disclosure, the anti-VEGF antibodies or fragments thereof can be antibodies or antibody fragments whose sequence has been modified to alter at least one constant region-mediated biological effector function relative to the corresponding wild type sequence.

For example, in some embodiments, an anti-VEGF antibody of the disclosure can be modified to reduce at least one constant region-mediated biological effector function relative to an unmodified antibody, e.g., reduced binding to the Fc receptor (FcγR). FcγR binding can be reduced by mutating the immunoglobulin constant region segment of the antibody at particular regions necessary for FcγR interactions (see e.g., Canfield and Morrison, 1991, J. Exp. Med. 173:1483-1491; and Lund et al., 1991, J. Immunol. 147:2657-2662). Reduction in FcγR binding ability of the antibody can also reduce other effector functions which rely on FcγR interactions, such as opsonization, phagocytosis and antigen-dependent cellular cytotoxicity ("ADCC").

In other embodiments, an anti-VEGF antibody of the disclosure can be modified to acquire or improve at least one constant region-mediated biological effector function relative to an unmodified antibody, e.g., to enhance FcγR interactions (see, e.g., US 2006/0134709). For example, an anti-VEGF antibody of the disclosure can have a constant region that binds FcγRIIA, FcγRIIB and/or FcγRIIIA with greater affinity than the corresponding wild type constant region.

Thus, antibodies of the disclosure can have alterations in biological activity that result in increased or decreased opsonization, phagocytosis, or ADCC. Such alterations are known in the art. For example, modifications in antibodies that reduce ADCC activity are described in U.S. Pat. No. 5,834,597. An exemplary ADCC lowering variant corresponds to "mutant 3" shown in FIG. 4 of U.S. Pat. No. 5,834,597, in which residue 236 is deleted and residues 234, 235 and 237 (using EU numbering) are substituted with alanines.

In some embodiments, the anti-VEGF antibodies of the disclosure have low levels of or lack fucose. Antibodies lacking fucose have been correlated with enhanced ADCC (activity, especially at low doses of antibody. See Shields et al., 2002, J. Biol. Chem. 277:26733-26740; Shinkawa et al., 2003, J. Biol. Chem. 278:3466-73. Methods of preparing fucose-less antibodies include growth in rat myeloma YB2/0 cells (ATCC CRL 1662). YB2/0 cells express low levels of FUT8 mRNA, which encodes α-1,6-fucosyltransferase, an enzyme necessary for fucosylation of polypeptides.

In yet another aspect, the anti-VEGF antibodies or fragments thereof can be antibodies or antibody fragments that have been modified to increase or reduce their binding affinities to the fetal Fc receptor, FcRn, for example by mutating the immunoglobulin constant region segment at particular regions involved in FcRn interactions (see, e.g., WO 2005/123780). In particular embodiments, an anti-VEGF antibody of the IgG class is mutated such that at least one of amino acid residues 250, 314, and 428 of the heavy chain constant region is substituted alone, or in any combinations thereof, such as at positions 250 and 428, or at positions 250 and 314, or at positions 314 and 428, or at positions 250, 314, and 428, with positions 250 and 428 a specific combination. For position 250, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. Specific combinations of suitable amino acid substitutions are identified in Table 1 of U.S. Pat. No. 7,217,797, which table is incorporated by reference herein in its entirety. Such mutations increase the antibody's binding to FcRn, which protects the antibody from degradation and increases its half-life.

In yet other aspects, an anti-VEGF antibody has one or more amino acids inserted into one or more of its hypervariable regions, for example as described in Jung and Pliickthun, 1997, Protein Engineering 10(9):959-966; Yazaki et al., 2004, Protein Eng Des. Sel. 17(5):481-9. Epub 2004 Aug. 17; and US 2007/0280931.

In various embodiments, the anti-VEGF antibodies or fragments thereof can be antibodies or antibody fragments that have been modified for increased expression in heterologous hosts. In certain embodiments, the anti-VEGF antibodies or fragments thereof can be antibodies or antibody fragments that have been modified for increased expression in and/or secretion from heterologous host cells. In some embodiments, the anti-VEGF antibodies or fragments thereof are modified for increased expression in bacteria, such as E. coli. In other embodiments, the anti-VEGF antibodies or fragments thereof are modified for increased expression in yeast (Kieke et al., 1999, Proc. Nat'l Acad. Sci. USA 96:5651-

5656). In still other embodiments, the anti-VEGF antibodies or fragments thereof are modified for increased expression in insect cells. In additional embodiments, the anti-VEGF antibodies or fragments thereof are modified for increased expression in mammalian cells, such as CHO cells.

In certain embodiments, the anti-VEGF antibodies or fragments thereof can be antibodies or antibody fragments that have been modified to increase stability of the antibodies during production. In some embodiments, the antibodies or fragments thereof can be modified to replace one or more amino acids such as asparagine or glutamine that are susceptible to nonenzymatic deamidation with amino acids that do not undergo deamidation (Huang et al., 2005, Anal. Chem. 77:1432-1439). In other embodiments, the antibodies or fragments thereof can be modified to replace one or more amino acids that is susceptible to oxidation, such as methionine, cysteine or tryptophan, with an amino acid that does not readily undergo oxidation. In still other embodiments, the antibodies or fragments thereof can be modified to replace one or more amino acids that is susceptible to cyclization, such as asparagine or glutamic acid, with an amino acid that does not readily undergo cyclization.

6.2 Nucleic Acids and Expression Systems

The present disclosure encompasses nucleic acid molecules and host cells encoding the anti-VEGF antibodies of the disclosure.

An anti-VEGF antibody of the disclosure can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N.Y., 1989), Current Protocols in Molecular Biology (Ausubel, F. M. et al., eds., Greene Publishing Associates, 1989) and in U.S. Pat. No. 4,816,397.

In one embodiment, the anti-VEGF antibodies are similar to bevacizumab or ranibizumab but for changes in one or more CDRs. In another embodiment, the anti-VEGF antibodies are similar to bevacizumab or ranibizumab but for changes in one or more framework regions. In yet another embodiment, the anti-VEGF antibodies are similar to bevacizumab or ranibizumab but for changes in one or more CDRs and in one or more framework regions. Such antibodies are referred to herein collectively as having "bevacizumab-related" or "ranibizumab-related" sequences and are sometimes referenced simply as anti-VEGF antibodies of the disclosure. To generate nucleic acids encoding anti-VEGF antibodies, DNA fragments encoding the light and heavy chain variable regions are first obtained. These DNAs can be obtained by amplification and modification of germline DNA or cDNA encoding light and heavy chain variable sequences, for example using the polymerase chain reaction (PCR). Germline DNA sequences for human heavy and light chain variable region genes are known in the art (see, e.g., the "VBASE" human germline sequence database; see also Kabat, E. A. et al., 1991, Sequences of Proteins of Immunological Interest, Fifth Edition, U.S. Department of Health and Human Services, NIH Publication No. 91-3242; Tomlinson et al., 1992, J. Mol. Biol. 22T:116-198; and Cox et al., 1994, Eur. J. Immunol. 24:827-836; the contents of each of which are incorporated herein by reference). A DNA fragment encoding the heavy or light chain variable region of bevacizumab or ranibizumab can be synthesized and used as a template for mutagenesis to generate a variant as described herein using routine mutagenesis techniques; alternatively, a DNA fragment encoding the variant can be directly synthesized.

Once DNA fragments encoding anti-VEGF VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions ($CH_1$, $CH_2$, $CH_3$ and, optionally, $CH_4$). The sequences of human heavy chain constant region genes are known in the art (see, e.g., Kabat, E. A. et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but in certain embodiments is an $IgG_1$ or $IgG_4$ constant region. For a Fab fragment heavy chain gene, the VH-encoding DNA can be operatively linked to another DNA molecule encoding only the heavy chain $CH_1$ constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see, e.g., Kabat, E. A. et al., 1991, Sequences of Proteins of Immunological Interest, Fifth Edition (U.S. Department of Health and Human Services, NIH Publication No. 91-3242)) and DNA fragments encompassing these regions can be obtained by standard PCR amplification. The light chain constant region can be a kappa or lambda constant region, but in certain embodiments is a kappa constant region. To create a scFv gene, the VH- and VL-encoding DNA fragments are operatively linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see, e.g., Bird et al., 1988, Science 242:423-426; Huston et al., 1988, Proc. Natl. Acad. Sci. USA 85:5879-5883; McCafferty et al., 1990, Nature 348:552-554).

To express the anti-VEGF antibodies of the disclosure, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the light or heavy chain sequences of the anti-VEGF antibodies of the disclosure, the expression vector can already carry antibody constant region sequences. For example, one approach to converting the anti-VEGF VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185 (Academic Press, San Diego, Calif., 1990). It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al., and U.S. Pat. No. 4,968,615 by Schaffner et al., In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, puromycin, blasticidin, hygromycin or methotrexate, on a host cell into which the vector has been introduced. Suitable selectable marker genes include the dihydrofolate reductase (DHFR) gene (for use in DHFR⁻ host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE-dextran transfection and the like.

It is possible to express the antibodies of the disclosure in either prokaryotic or eukaryotic host cells. In certain embodiments, expression of antibodies is performed in eukaryotic cells, e.g., mammalian host cells, for optimal secretion of a properly folded and immunologically active antibody. Exemplary mammalian host cells for expressing the recombinant antibodies of the disclosure include Chinese Hamster Ovary (CHO cells) (including DHFR⁻ CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601-621), NS0 myeloma cells, COS cells, 293 cells and SP2/0 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as Fab fragments or scFv molecules. It is understood that variations on the above procedure are within the scope of the present disclosure. For example, it can be desirable to transfect a host cell with DNA encoding either the light chain or the heavy chain (but not both) of an anti-VEGF antibody of this disclosure.

Recombinant DNA technology can also be used to remove some or all of the DNA encoding either or both of the light and heavy chains that is not necessary for binding to VEGF. The molecules expressed from such truncated DNA molecules are also encompassed by the antibodies of the disclosure.

In addition, bifunctional antibodies can be produced in which one heavy and one light chain are an antibody of the disclosure and the other heavy and light chain are specific for an antigen other than VEGF by crosslinking an antibody of the disclosure to a second antibody by standard chemical crosslinking methods. Bifunctional antibodies can also be made by expressing a nucleic acid engineered to encode a bifunctional antibody.

In certain embodiments, dual specific antibodies, i.e., antibodies that bind VEGF and an unrelated antigen using the same binding site, can be produced by mutating amino acid residues in the light chain and/or heavy chain CDRs. In various embodiments, dual specific antibodies that bind two antigens, such as HER2 and VEGF, can be produced by mutating amino acid residues in the periphery of the antigen binding site (Bostrom et al., 2009, Science 323:1610-1614). Dual functional antibodies can be made by expressing a nucleic acid engineered to encode a dual specific antibody.

For recombinant expression of an anti-VEGF antibody of the disclosure, the host cell can be co-transfected with two expression vectors of the disclosure, the first vector encoding a heavy chain derived polypeptide and the second vector encoding a light chain derived polypeptide. Typically, the two vectors each contain a separate selectable marker. Alternatively, a single vector can be used which encodes both heavy and light chain polypeptides.

Once a nucleic acid encoding one or more portions of an anti-VEGF antibody is generated, further alterations or mutations can be introduced into the coding sequence, for example to generate nucleic acids encoding antibodies with different CDR sequences, antibodies with reduced affinity to the Fc receptor, or antibodies of different subclasses.

The anti-VEGF antibodies of the disclosure can also be produced by chemical synthesis (e.g., by the methods described in Solid Phase Peptide Synthesis, $2^{nd}$ ed., 1984 The Pierce Chemical Co., Rockford, Ill.). Variant antibodies can also be generated using a cell-free platform (see, e.g., Chu et al., 2001, Biochemia No. 2 (Roche Molecular Biologicals)).

Once an anti-VEGF antibody of the disclosure has been produced by recombinant expression, it can be purified by any method known in the art for purification of an immunoglobulin molecule, for example, by chromatography (e.g., ion exchange, affinity, particularly by affinity for VEGF after Protein A or Protein G selection, and sizing column chromatography), centrifugation, differential solubility, or by any other standard technique for the purification of proteins. Further, the anti-VEGF antibodies of the present disclosure or fragments thereof can be fused to heterologous polypeptide sequences described herein or otherwise known in the art to facilitate purification.

Once isolated, an anti-VEGF antibody can, if desired, be further purified, e.g., by high performance liquid chromatography (See, e.g., Fisher, Laboratory Techniques In Biochemistry And Molecular Biology (Work and Burdon, eds., Elsevier, 1980), or by gel filtration chromatography on a Superdex™ 75 column (Pharmacia Biotech AB, Uppsala, Sweden).

6.3 Biological Activities of Anti-VEGF Antibodies

In certain embodiments, the anti-VEGF antibodies of the disclosure have certain biological activities, such as competing with bevacizumab or ranibizumab for binding to VEGF or neutralizing VEGF activity.

Accordingly, in certain embodiments, anti-VEGF antibodies of the disclosure compete with bevacizumab or ranibizumab for binding to VEGF. The ability to compete for binding to VEGF can be tested using a competition assay. In one example of a competition assay, VEGF is adhered onto a solid surface, e.g., a microwell plate, by contacting the plate with a solution of VEGF (e.g., at a concentration of 1 µg/mL in PBS over night at 4° C.). The plate is washed (e.g., 0.1% Tween 20 in PBS) and blocked (e.g., in Superblock, Thermo Scientific, Rockford, Ill.). A mixture of sub-saturating amount of biotinylated bevacizumab (80 ng/mL) or an equivalent amount of biotinylated ranibizumab and unlabeled bevacizumab (or ranibizumab as the case may be) (the "reference" antibody) or competing anti-VEGF antibody (the "test" antibody) antibody in serial dilution (e.g., at a concentration of 2.8 µg/mL, 8.3 µg/mL, or 25 µg/mL) in ELISA buffer (e.g., 1% BSA and 0.1% Tween 20 in PBS) is added to wells and plates are incubated for 1 hour with gentle shaking. The plate is washed, 1 µg/mL HRP-conjugated Streptavidin diluted in ELISA buffer is added to each well and the plates incubated for 1 hour. Plates are washed and bound antibodies were detected by addition of substrate (e.g., TMB, Biofx Laboratories Inc., Owings Mills, Md.). The reaction is terminated by addition of stop buffer (e.g., Bio FX Stop Reagents, Biofx Laboratories Inc., Owings Mills, Md.) and the absorbance is measured at 650 nm using microplate reader (e.g., VERSAmax, Molecular Devices, Sunnyvale, Calif.). Variations on this competition assay can also be used to test competition between an anti-VEGF antibody of the disclosure and bevacizumab or ranibizumab. For example, in certain aspects, the anti-VEGF antibody is used as a reference antibody and bevacizumab or ranibizumab is used as a test antibody. Additionally, instead of soluble VEGF, membrane-bound VEGF expressed on the surfaces of cell (for example mammalian cells) in culture can be used. Other formats for competition assays are known in the art and can be employed.

In various embodiments, an anti-VEGF antibody of the disclosure reduces the binding of labeled bevacizumab or ranibizumab by at least 30%, by at least 40%, by at least 50%, by at least 60%, by at least 70%, by at least 80%, by at least 90%, by at least 95%, by at least 99% or by a percentage ranging between any of the foregoing values (e.g., an anti-VEGF antibody of the disclosure reduces the binding of labeled bevacizumab or ranibizumab by 50% to 70%) when the anti-VEGF antibody is used at a concentration of 0.08 µg/mL, 0.4 µg/mL, 2 µg/mL, 10 µg/mL, 50 µg/mL, 100 µg/mL or at a concentration ranging between any of the foregoing values (e.g., at a concentration ranging from 2 µg/mL to 10 µg/mL).

In other embodiments, bevacizumab or ranibizumab reduces the binding of a labeled anti-VEGF antibody of the disclosure by at least 40%, by at least 50%, by at least 60%, by at least 70%, by at least 80%, by at least 90%, or by a percentage ranging between any of the foregoing values (e.g., bevacizumab or ranibizumab reduces the binding of a labeled an anti-VEGF antibody of the disclosure by 50% to 70%) when bevacizumab or ranibizumab is used at a concentration of 0.4 µg/mL, 2 µg/mL, 10 µg/mL, 50 µg/mL, 250 µg/mL or at a concentration ranging between any of the foregoing values (e.g., at a concentration ranging from 2 µg/mL to 10 µg/mL).

In other aspects, an anti-VEGF antibody of the disclosure inhibits (or neutralizes) VEGF activity in a range of in vitro assays, such as cell proliferation or cell migration. For example, in one embodiment, the VEGF activity assayed is induction of endothelial cell ("EC") proliferation (see, e.g., protocol of Qin et al., 2006, J. Biol. Chem. 281:32550-32558). In another embodiment, the VEGF activity assayed is induction of EC migration (see, e.g., the in vitro scratch assay protocol described of Liang et al., 2007, Nat. Protoc. 2:329-333). In a specific embodiment, an anti-VEGF antibody is tested for the ability to reverse proliferation and cell migration stimulated by VEGF and delocalization of tight junction proteins induced by $VEGF_{165}$ in immortalized bovine retinal endothelial cells (Deissler et al., 2008, British Journal of Opthalmology 92:839-843). In yet another embodiment, the neutralization of VEGF activity is assayed using a reporter assay (see, e.g., Yohno et al., 2003, Biological & Pharmaceutical Bulletin 26(4):417-20 and U.S. Pat. No. 6,787,323).

Other formats for VEGF neutralization assays are known in the art and can be employed.

In various embodiments, an anti-VEGF antibody of the disclosure neutralizes VEGF by at least 30%, by at least 40%, by at least 50%, by at least 60%, by at least 70%, by at least 80%, by at least 90%, or by a percentage ranging between any of the foregoing values (e.g., an anti-VEGF antibody of the disclosure neutralizes VEGF activity by 50% to 70%) when the anti-VEGF antibody is used at a concentration of 2 ng/mL, 5 ng/mL, 10 ng/mL, 20 ng/mL, 0.1 µg/mL, 0.2 µg/mL, 1 µg/mL, 2 µg/mL, 5 µg/mL, 10 µg/mL, 20 µg/mL, or at a concentration ranging between any of the foregoing values (e.g., at a concentration ranging from 1 µg/mL to 5 µg/mL).

In some embodiments, an anti-VEGF antibody of the disclosure is at least 0.7-fold as effective, 0.8-fold as effective, at least 0.9-fold as effective, at least 1-fold as effective, at least 1.1-fold as effective, at least 1.25-fold as effective, at least 1.5-fold as effective, at least 2-fold as effective, at least 5-fold as effective, at least 10-fold as effective, at least 20-fold as effective, at least 50-fold as effective, at least 100-fold as effective, at least 200-fold as effective, at least 500-fold as effective, at least 1000-fold as effective as bevacizumab or ranibizumab at neutralizing VEGF, or having an effectiveness at neutralizing VEGF relative to bevacizumab or ranibizumab ranging between any pair of the foregoing values (e.g., 0.9-fold to 5-fold as effective as bevacizumab or ranibizumab or 2-fold to 50-fold as effective as bevacizumab or ranibizumab in neutralizing VEGF).

6.4 Kinetic Properties of Anti-VEGF Antibodies

In certain embodiments, the anti-VEGF antibodies of the disclosure have a high binding affinity for VEGF. In specific embodiments, the anti-VEGF antibodies of the present disclosure have specific association rate constants ($k_{on}$ or $k_a$ values), dissociation rate constants ($k_{off}$ or $k_d$ values), affinity constants ($K_A$ values), dissociation constants ($K_D$ values) and/or $IC_{50}$ values. In various embodiments, binding constants for the interaction of the anti-VEGF antibodies with VEGF receptor can be determined using surface plasmon resonance, e.g., according to the method disclosed in Karlsson et al., 1991, J. Immunol. Methods 145:229-240. In certain aspects, such values are selected from the following embodiments.

In a specific embodiment, an anti-VEGF antibody of the disclosure binds to VEGF with a $k_{on}$ of at least $10^4$ $M^{-1}$ $s^{-1}$, at least $5\times10^4$ $M^{-1}$ $s^-$, at least $10^5$ $M^{-1}$ $s^{-1}$, at least $5\times10^5$ $M^{-1}$ $s^{-1}$, at least $10^6$ $M^{-1}$ $s^{-1}$, at least $5\times10^6$ $M^{-1}$ $s^{-1}$, at least $10^7$ $M^{-1}$ $s^{-1}$, at least $5\times10^7$ $M^{-1}$ $s^{-1}$, at least $10^8$ $M^{-1}$ $s^{-1}$, at least $5\times10^8$ $M^{-1}$ $s^{-1}$, at least $10^9$ $M^{-1}$ $s^{-1}$ or with a $k_{on}$ of any range between any pair of the foregoing values (e.g., $5\times10^5$ to $5\times10^6$ $M^{-1}$ $s^{-1}$ or $10^7$ to $10^8$ $M^{-1}$ $s^{-1}$).

In another embodiment, an anti-VEGF antibody of the disclosure binds to VEGF with a $k_{off}$ rate of $10^{-3}$ $s^{-1}$ or less, $5\times10^{-4}$ $s^{-1}$ or less, $10^{-4}$ $s^{-1}$ or less, $5\times10^{-5}$ $s^{-1}$ or less, $10^{-5}$ $s^{-1}$ or less, $5\times10^{-6}$ $s^{-1}$ or less, $10^{-6}$ $s^{-1}$ or less, $5\times10^{-7}$ $s^{-1}$ or less, $10^{-7}$ $s^{-1}$ or less, $5\times10^{-8}$ $s^{-1}$ or less, $10^{-8}$ $s^{-1}$ or less, or with a $k_{off}$ rate of any range between any pair of the foregoing values (e.g., $5\times10^{-4}$ to $10^{-6}$ $s^{-1}$, or $10^{-3}$ to $5\times10^{-5}$ $s^{-1}$).

In another embodiment, an anti-VEGF antibody of the disclosure binds to VEGF with a $K_A$ ($k_{on}/k_{off}$) of at least at least $10^8$ $M^{-1}$, at least $5\times10^9$ $M^{-1}$, at least $10^{10}$ $M^{-1}$, at least $5\times10^{10}$ $M^-$, $10^{11}$ $M^{-1}$, at least $5\times10^{11}$ $M^{-1}$, at least $10^{12}$ $M^{-1}$, at least $5\times10^{12}$ $M^{-1}$, at least $10^{13}$ $M^{-1}$, at least $5\times10^{13}$ $M^{-1}$, at least $10^{14}$ $M^{-1}$, at least $5\times10^{14}$ $M^{-1}$, at least $10^{15}$ $M^{-1}$ or with a $K_A$ of any range between any pair of the foregoing values (e.g., from $5\times10^9$ $M^{-1}$ to $10^{11}$ $M^{-1}$, or from $10^{11}$ $M^{-1}$ to $5\times10^{14}$ $M^{-1}$).

In other embodiments, an anti-VEGF antibody of the disclosure binds to VEGF with a $K_D$ ($k_{off}/k_{on}$) of $10^{-8}$ M or less, $5\times10^{-9}$ M or less, $10^{-9}$ M or less, $5\times10^{-10}$ M or less, $10^{-10}$ M or less, $5\times10^{-11}$ M or less, $10^{-11}$ M or less, $5\times10^{-12}$ M or less, $10^{-12}$ M or less, $5\times10^{-13}$ M or less, $10^{-13}$ M or less, $5\times10^{-14}$ M or less, $10^{-14}$ M or less, $5\times10^{-15}$ M or less, $10^{-15}$ M or less, or with a $K_D$ of any range between any pair of the foregoing values (e.g., $5\times10^{-9}$ to $5\times10^{-12}$ M or from $5\times10^{-11\ M}$ to $5\times10^{-13}$ M).

In specific embodiments, the $K_D$ ($k_{off}/k_{on}$) value is determined by assays well known in the art or described herein, e.g., ELISA, isothermal titration calorimetry (ITC), fluorescent polarization assay or any other biosensors such as BIAcore.

In some embodiments, an anti-VEGF antibody of the disclosure binds to VEGF and inhibits the binding of VEGF to a VEGF receptor (Flt-1 or Flk-1) at an $IC_{50}$ value of less than $5\times10^7$ nM, less than $10^7$ nM, less than $5\times10^6$ nM, less than $10^6$ nM, less than $5\times10^5$ nM, less than $10^5$ nM, less than $5\times10^4$ nM, less than $10^4$ nM, less than $5\times10^3$ nM, less than $10^3$ nM, less than $5\times10^2$ nM, less than 100 nM, less than 90 nM, less than 80 nM, less than 70 nM, less than 65 nM, less than 60 nM, less than 50 nM, less than 40 nM, less than 30 nM, less than 25 nM, less than 20 nM, less than 15 nM, less than 12 nM, less than 10 nM, less than 5 nM, less than 1 nM, less than $5\times10^{-1}$ nM, less than $10^{-1}$ nM, less than $5\times10^{-2}$ nM, less than $10^{-2}$ nM, less than $5\times10^{-3}$ nM, less than $10^{-3}$ nM, less than $5\times10^{-4}$ nM, or less than $10^{-4}$ nM, or with an $IC_{50}$ of any range between any pair of the foregoing values (e.g., $5\times10^7$ to 50 nM, or 15 nM to $5\times10^{-3}$ nM). $IC_{50}$ can be measured according to methods well known in the art or described herein, e.g., ELISA.

In other embodiments, an anti-VEGF antibody of the disclosure binds to VEGF and neutralizes the activity VEGF in a bioassay (e.g., EC proliferation or migration) at an $IC_{50}$ value of less than $5\times10^7$ nM, less than $10^7$ nM, less than $5\times10^6$ nM, less than $10^6$ nM, less than $5\times10^5$ nM, less than $10^5$ nM, less than $5\times10^4$ nM, less than $10^4$ nM, less than $5\times10^3$ nM, less than $10^3$ nM, less than $5\times10^2$ nM, less than 100 nM, less than 90 nM, less than 80 nM, less than 70 nM, less than 65 nM, less than 60 nM, less than 50 nM, less than 40 nM, less than 30 nM, less than 25 nM, less than 20 nM, less than 15 nM, less than 12 nM, less than 10 nM, less than 5 nM, less than 1 nM, less than $5\times10^{-1}$ nM, less than $10^{-1}$ nM, less than $5\times10^{-2}$ nM, less than $10^{-2}$ nM, less than $5\times10^{-3}$ nM, less than $10^{-3}$ nM, less than $5\times10^{-4}$ nM, or less than $10^{-4}$ nM, or with an $IC_{50}$ of any range between any pair of the foregoing values (e.g., $5\times10^7$ to 50 nM, or 15 nM to $5\times10^{-3}$ nM). An exemplary neutralization assay that can be used to measure the $IC_{50}$ of an anti-VEGF antibody is described in Section 6.3 below.

In certain embodiments, an anti-VEGF antibody binds to VEGF and inhibits the binding of VEGF to Flt-1, Flk-1 or both, or inhibits VEGF activity in a VEGF neutralization assay, at an $IC_{50}$ value of between approximately 1 pm and approximately 1 μM. In specific embodiments, an anti-VEGF antibody binds to VEGF and inhibits the binding of VEGF to Flt-1, Flk-1 or both, or inhibits VEGF activity in a VEGF neutralization assay, at an $IC_{50}$ value of between 10 pM and 100 nM, between 100 pM and 10 nM, between 200 pM and 5 nM, between 300 pM and 4 nM, between 500 pM and 3 nM, between 750 pM and 2 nM, between 1 nM and 20 nM, between 500 pM and 40 nM, between 50 pM and 50 nM, between 250 pM and 100 nM, and between 100 nM and 1 μM, or with an $IC_{50}$ of any range between any pair of the foregoing values (e.g., 10 pM to 50 nM, or 750 pM to 2 nM).

In certain aspects of the foregoing embodiments, the $IC_{50}$ is measured in the presence of VEGF at a concentration of 0.001 μM, 0.005 μM, 0.01 μM, 0.05 μM, 0.1 μM, 0.5 μM, 1 μM, 10 μM, 20 μM, 30 μM, 40 μM, 50 μM, 60 μM, 70 μM, 80 μM, 90 μM, 100 μM, 200 μM, 300 μM, 400 μM, 500 μM, 600 μM, 700 μM, 800 μM, 900 μM, 1000 μM or at a concentration of any range between any pair of the foregoing values (e.g., 0.01 to 50 μM, or 10 μM to 100 μM).

In certain embodiments, the kinetic properties of an antibody of the disclosure are comparable to, or improved relative to, bevacizumab or of ranibizumab in a comparable assay. For example, in certain embodiments, an anti-VEGF antibody of the disclosure binds to VEGF with a $k_{on}$ rate ranging from approximately 0.5× to 1000× of the $k_{on}$ of bevacizumab or of ranibizumab, for example a $k_{on}$ of 0.5× of the $k_{on}$ of bevacizumab or of ranibizumab, a $k_{on}$ of 0.75× of the $k_{on}$ of bevacizumab or of ranibizumab, a $k_{on}$ of 0.9× of the $k_{on}$ of bevacizumab or of ranibizumab, a $k_{on}$ of 1× of the $k_{on}$ of bevacizumab or of ranibizumab, a $k_{on}$ of 1.1× of the $k_{on}$ of bevacizumab or of ranibizumab, a $k_{on}$ of 1.2× of the $k_{on}$ of bevacizumab or of ranibizumab, a $k_{on}$ of 1.3× of the $k_{on}$ of bevacizumab or of ranibizumab, a $k_{on}$ of 1.4× of the $k_{on}$ of bevacizumab or of ranibizumab, a $k_{on}$ of 1.5× of the $k_{on}$ of bevacizumab or of ranibizumab, a $k_{on}$ of 1.75× of the $k_{on}$ of bevacizumab or of ranibizumab, a $k_{on}$ of 2× of the $k_{on}$ of bevacizumab or of ranibizumab, a $k_{on}$ of 2.25× of the $k_{on}$ of bevacizumab or of ranibizumab, a $k_{on}$ of 2.5× of the $k_{on}$ of bevacizumab or of ranibizumab, a $k_{on}$ of 3× of the $k_{on}$ of bevacizumab or of ranibizumab, a $k_{on}$ of 4× of the $k_{on}$ of bevacizumab or of ranibizumab, a $k_{on}$ of 5× of the $k_{on}$ of bevacizumab or of ranibizumab, a $k_{on}$ of 7.5× of the $k_{on}$ of bevacizumab or of ranibizumab, a $k_{on}$ of 10× of the $k_{on}$ of bevacizumab or of ranibizumab, a $k_{on}$ of 15× of the $k_{on}$ of bevacizumab or of ranibizumab, a $k_{on}$ of 20× of the $k_{on}$ of bevacizumab or of ranibizumab, a $k_{on}$ of 50× of the $k_{on}$ of bevacizumab or of ranibizumab, a $k_{on}$ of 75× of the $k_{on}$ of bevacizumab or of ranibizumab, a $k_{on}$ of 100× of the $k_{on}$ of bevacizumab or of ranibizumab, a $k_{on}$ of 150× of the $k_{on}$ of bevacizumab or of ranibizumab, a $k_{on}$ of 200× of the $k_{on}$ of bevacizumab or of ranibizumab, a $k_{on}$ of 200× of the $k_{on}$ of bevacizumab or of ranibizumab or a $k_{on}$ ranging between any pair of the foregoing values, e.g., a $k_{on}$ of 2×-75× of the $k_{on}$ of bevacizumab or of ranibizumab, a $k_{on}$ of 5×-100× of the $k_{on}$ of bevacizumab or of ranibizumab, a $k_{on}$ of 0.5×-1000× of the $k_{on}$ of bevacizumab or of ranibizumab, a $k_{on}$ of 0.75×-200× of the $k_{on}$ of bevacizumab or of ranibizumab, etc.

In certain embodiments, an anti-VEGF antibody of the disclosure binds to VEGF with a $k_{off}$ rate ranging from 0.001× to 3× of the $k_{off}$ of bevacizumab or of ranibizumab, for example a $k_{off}$ of 0.002× of the $k_{off}$ of bevacizumab or of ranibizumab, a $k_{off}$ of 0.005× of the $k_{off}$ of bevacizumab or of ranibizumab, a $k_{off}$ of 0.0075× of the $k_{off}$ of bevacizumab or of ranibizumab, a $k_{off}$ of 0.01× of the $k_{off}$ of bevacizumab or of ranibizumab, a $k_{off}$ of 0.025× of the $k_{off}$ of bevacizumab or of ranibizumab, a $k_{off}$ of 0.05× of the $k_{off}$ of bevacizumab or of ranibizumab, a $k_{off}$ of 0.075× of the $k_{off}$ of bevacizumab or of ranibizumab, a $k_{off}$ of 0.1× of the $k_{off}$ of bevacizumab or of ranibizumab, a $k_{off}$ of 0.25× of the $k_{off}$ of bevacizumab or of ranibizumab, a $k_{off}$ of 0.5× of the $k_{off}$ of bevacizumab or of ranibizumab, a $k_{off}$ of 0.75× of the $k_{off}$ of bevacizumab or of ranibizumab, a $k_{off}$ of 0.9× of the $k_{off}$ of bevacizumab or of ranibizumab, a $k_{off}$ of 1× of the $k_{off}$ of bevacizumab or of ranibizumab, a $k_{off}$ of 1.1× of the $k_{off}$ of bevacizumab or of ranibizumab, a $k_{off}$ of 1.25× of the $k_{off}$ of bevacizumab or of ranibizumab, a $k_{off}$ of 1.5× of the $k_{off}$ of bevacizumab or of ranibizumab, a $k_{off}$ of 1.75× of the $k_{off}$ of bevacizumab or of ranibizumab, a $k_{off}$ of 4× of the $k_{off}$ of bevacizumab or of ranibizumab, a $k_{off}$ of 3× of the $k_{off}$ of bevacizumab or of ranibizumab, a $k_{off}$ of 2× of the $k_{off}$ of bevacizumab or of ranibizumab, a $k_{off}$ of 3× of the $k_{off}$ of bevacizumab or of ranibizumab, or a $k_{off}$ ranging between any pair of the foregoing values, e.g., a $k_{off}$ of 0.01× to 1.1× of the $k_{off}$ of bevacizumab or of ranibizumab, a $k_{off}$ of 0.05×-1.25× of the $k_{off}$ of bevacizumab or of ranibizumab, a $k_{off}$ of 0.1×-0.9× of the $k_{off}$ of bevacizumab or of ranibizumab, etc.

In other embodiments, an anti-VEGF antibody of the disclosure binds to VEGF with a $K_A$ ($k_{on}/k_{off}$) ranging from 0.25× to 1000× of the $K_A$ of bevacizumab or of ranibizumab, for example a $K_A$ of 0.5× of the $K_A$ of bevacizumab or of ranibizumab, a $K_A$ of 0.75× of the $K_A$ of bevacizumab or of ranibizumab, a $K_A$ of 1× of the $K_A$ of bevacizumab or of ranibizumab, a $K_A$ of 2× of the $K_A$ of bevacizumab or of ranibizumab, a $K_A$ of 4× of the $K_A$ of bevacizumab or of ranibizumab, a $K_A$ of 10× of the $K_A$ of bevacizumab or of ranibizumab, a $K_A$ of 15× of the $K_A$ of bevacizumab or of ranibizumab, a $K_A$ of 20× of the $K_A$ of bevacizumab or of ranibizumab, a $K_A$ of 30× of the $K_A$ of bevacizumab or of ranibizumab, a $K_A$ of 40× of the $K_A$ of bevacizumab or of ranibizumab, a $K_A$ of 50× of the $K_A$ of bevacizumab or of ranibizumab, a $K_A$ of 100× of the $K_A$ of bevacizumab or of ranibizumab, a $K_A$ of 250× of the $K_A$ of bevacizumab or of ranibizumab, a $K_A$ of 500× of the $K_A$ of bevacizumab or of ranibizumab, a $K_A$ of 750× of the $K_A$ of bevacizumab or of ranibizumab, a $K_A$ of 1000× of the $K_A$ of bevacizumab or of ranibizumab or a $K_A$ ranging between any pair of the foregoing values, e.g., a $K_A$ of 0.75×-10 5× of the $K_A$ of bevacizumab or of ranibizumab, a $K_A$ of 1×-100× of the $K_A$ of bevacizumab or of ranibizumab, a $K_A$ of 10×-20× of the $K_A$ of bevacizumab or of ranibizumab, a $K_A$ of 4×-50× of the $K_A$ of bevacizumab or of ranibizumab, a $K_A$ of 2×-20× of the $K_A$ of bevacizumab or of ranibizumab, or any value or range that can be calculated from the $k_{on}$ and $k_{off}$ rates disclosed herein.

In other embodiments, an anti-VEGF antibody of the disclosure binds to VEGF a $K_D$ ($k_{off}/k_{on}$) ranging from ranging from 0.001× to 10× of the $K_D$ of bevacizumab or of ranibizumab, for example a $K_D$ of 0.001× of the $K_D$ of bevacizumab or of ranibizumab, a $K_D$ of 0.005× of the $K_D$ of bevacizumab or of ranibizumab, a $K_D$ of 0.01× of the $K_D$ of bevacizumab or of ranibizumab, a $K_D$ of 0.05× of the $K_D$ of bevacizumab or of ranibizumab, a $K_D$ of 0.075× of the $K_D$ of bevacizumab or of ranibizumab, a $K_D$ of 0.1× of the $K_D$ of bevacizumab or of ranibizumab, a $K_D$ of 0.2× of the $K_D$ of bevacizumab or of ranibizumab, a $K_D$ of 0.3× of the $K_D$ of bevacizumab or of ranibizumab, a $K_D$ of 0.4× of the $K_D$ of bevacizumab or of ranibizumab, a $K_D$ of 0.5× of the $K_D$ of bevacizumab or of ranibizumab, a $K_D$ of 0.6× of the $K_D$ of bevacizumab or of ranibizumab, a $K_D$ of 0.7× of the $K_D$ of bevacizumab or of ranibizumab, a $K_D$ of 0.8× of the $K_D$ of bevacizumab or of ranibizumab, a $K_D$ of 0.9× of the $K_D$ of bevacizumab or of ranibizumab, a $K_D$ of 1× of the $K_D$ of bevacizumab or of ranibizumab, a $K_D$ of 1.5× of the $K_D$ of bevacizumab or of ranibizumab, a $K_D$ of 2× of the $K_D$ of bevacizumab or of ranibizumab, a $K_D$ of 4× of the $K_D$ of bevacizumab or of ranibizumab, a $K_D$ of 7.5× of the $K_D$ of bevacizumab or of ranibizumab, a $K_D$ of 10× of the $K_D$ of bevacizumab or of ranibizumab or a $K_D$ ranging between any pair of the foregoing values, e.g., a $K_D$ of 0.01×-2× of the $K_D$ of bevacizumab or of ranibizumab, a $K_D$ of 0.1×-1.5× of the $K_D$ of bevacizumab or of ranibizumab, a $K_D$ of 0.7×-4× of the $K_D$ of bevacizumab or of ranibizumab, a $K_D$ of 0.2×-2× of the $K_D$ of bevacizumab or of ranibizumab or any value or range that can be calculated from the $k_{on}$ and $k_{off}$ rates disclosed herein.

In some embodiments, an anti-VEGF antibody of the disclosure binds to VEGF and inhibits the binding of VEGF to Flt-1, Flk-1 or both, or neutralize the activity of VEGF at an $IC_{50}$ value ranging from 0.001× to 10× of the $IC_{50}$ of bevacizumab or of ranibizumab, for example an $IC_{50}$ of 0.001× of the $IC_{50}$ of bevacizumab or of ranibizumab, an $IC_{50}$ of 0.005× of the $IC_{50}$ of bevacizumab or of ranibizumab, an $IC_{50}$ of 0.01× of the $IC_{50}$ of bevacizumab or of ranibizumab, an $IC_{50}$ of 0.05× of the $IC_{50}$ of bevacizumab or of ranibizumab, an $IC_{50}$ of 0.075× of the $IC_{50}$ of bevacizumab or of ranibizumab, an $IC_{50}$ of 0.1× of the $IC_{50}$ of bevacizumab or of ranibizumab, an $IC_{50}$ of 0.2× of the $IC_{50}$ of bevacizumab or of ranibizumab, an $IC_{50}$ of 0.3× of the $IC_{50}$ of bevacizumab or of ranibizumab, an $IC_{50}$ of 0.4× of the $IC_{50}$ of bevacizumab or of ranibizumab, an $IC_{50}$ of 0.5× of the $IC_{50}$ of bevacizumab or of ranibizumab, an $IC_{50}$ of 0.6× of the $IC_{50}$ of bevacizumab or of ranibizumab, an $IC_{50}$ of 0.7× of the $IC_{50}$ of bevacizumab or of ranibizumab, an $IC_{50}$ of 0.8× of the $IC_{50}$ of bevacizumab or of ranibizumab, an $IC_{50}$ of 0.9× of the $IC_{50}$ of bevacizumab or of ranibizumab, an $IC_{50}$ of 1× of the $IC_{50}$ of bevacizumab or of ranibizumab, an $IC_{50}$ of 1.5× of the $IC_{50}$ of bevacizumab or of ranibizumab, an $IC_{50}$ of 2× of the $IC_{50}$ of bevacizumab or of ranibizumab, an $IC_{50}$ of 4× of the $IC_{50}$ of bevacizumab or of ranibizumab, an $IC_{50}$ of 7.5× of the $IC_{50}$ of bevacizumab or of ranibizumab, an $IC_{50}$ of 10× of the $IC_{50}$ of bevacizumab or of ranibizumab or an $IC_{50}$ ranging between any pair of the foregoing values, e.g., an $IC_{50}$ of 0.01×-2× of the $IC_{50}$ of bevacizumab or of ranibizumab, an $IC_{50}$ of 0.1×-1.5× of the $IC_{50}$ of bevacizumab or of ranibizumab, an $IC_{50}$ of 0.7×-4× of the $IC_{50}$ of bevacizumab or of ranibizumab, an $IC_{50}$ of 0.2×-2× of the $IC_{50}$ of bevacizumab or of ranibizumab. In certain embodiments, a single CDR substitution can result in the foregoing differences in $IC_{50}$ as compared to bevacizumab or ranibizumab, whereas an anti-VEGF antibody of the disclosure can comprise such substitution and up to 16 additional CDR substitutions as compared to bevacizumab or ranibizumab.

6.5 Reduced Immunogenicity of Anti-VEGF Antibodies

In certain aspects, the present disclosure provides anti-VEGF antibodies having reduced immunogenicity as compared to bevacizumab or ranibizumab. The present disclosure provides anti-VEGF antibodies having single or multiple amino acid substitutions in their CDRs and/or framework regions as compared to the CDRs of bevacizumab, wherein at least one substitution reduces the immunogenicity of the antibody as compared to bevacizumab or ranibizumab. In certain embodiments, the reduced immunogenicity results from one or more amino acid substitutions that result in eliminating or mitigating one or more T cell epitopes.

In certain aspects, the anti-VEGF antibodies of the disclosure having reduced immunogenicity have comparable or improved biological activity as compared to bevacizumab or ranibizumab, e.g., affinity towards VEGF or neutralization of VEGF activity. Such properties can be tested, for example, by the methods described in Section 6.3 above.

In certain embodiments, the immunogenicity of an anti-VEGF antibody of the disclosure is reduced relative to bevacizumab or ranibizumab antibody. Such antibodies generally have variant sequences relative to the heavy and/or light chain variable region in regions corresponding to SEQ ID NO:25, SEQ ID NO:62 and/or SEQ ID NO:74. The antibodies will generally have one, two or three amino acid substitutions in one, two or all three sequences corresponding to SEQ ID NO:25, SEQ ID NO:62, and SEQ ID NO:74, although up to four or five substitutions in one, two or all three regions are contemplated herein.

As used in the present disclosure, a variant with "reduced immunogenicity" refers to an anti-VEGF antibody with a variant sequence in a region corresponding to SEQ ID NO:25, SEQ ID NO:62, and/or SEQ ID NO:74 that elicits a reduced proliferative response in peripheral blood mononuclear cells as compared to a peptide of SEQ ID NO:25, SEQ ID NO:62, or SEQ ID NO:74, respectively. An exemplary proliferation assay that can be used to evaluate the proliferative response is set forth in Section 7 below. The reduced proliferative response can be reflected in terms of the percentage of responders, the stimulation index, or both.

In other embodiments, as compared to a peptide having the sequence of SEQ ID NO:25, SEQ ID NO:62, or SEQ ID NO:74, the variant sequence results in at least 25% fewer responders, in at least 30% fewer responders, in at least 35% fewer responders, in at least 40% fewer responders, in at least 45% fewer responders, in at least 50% fewer responders, in at least 60% fewer responders, in at least 65% fewer responders, in at least 70% fewer responders, in at least 75% fewer responders, in at least 80% fewer responders, in at least 85% fewer responders, in at least 90% fewer responders, in at least 95% fewer responders, 100% fewer responders, or a reduction in responders in a range between any of the foregoing values, e.g., 25%-75% fewer responders, 50%-90% fewer responders, 60%-100% fewer responders, 70%-90% fewer responders, or the like.

In other embodiments, the variant sequence results in a stimulation index that is at least 5% less, at least 10% less, at least 15% less, at least 20% less, at least 25% less, at least 30% less, at least 35% less, or at least 40% less than the stimulation index elicited by a peptide of SEQ ID NO:25, SEQ ID NO:62, or SEQ ID NO:74, respectively, or results in a stimulation index reduced by a range between any of the foregoing values as compared to a peptide of SEQ ID NO:25, SEQ ID NO:62, or SEQ ID NO:74, e.g., 5%-20% less, 10%-30% less, 25%-35% less, 30%-40% less, or the like.

Exemplary embodiments of candidate anti-VEGF antibodies with reduced immunogenicity as compared to bevacizumab or ranibizumab comprise one or more of the CDR substitutions or combinations of substitutions set forth in FIG. 10. Optionally, anti-VEGF antibodies with reduced immunogenicity as compared to bevacizumab or ranibizumab comprise one or more additional substitutions, such as the CDR mutations in any of FIGS. 11-17, singly or in combination.

Yet further exemplary embodiments of candidate anti-VEGF antibodies with reduced immunogenicity as compared to bevacizumab or ranibizumab comprise one or more of the CDR substitutions or combinations of substitutions set forth in FIGS. 18-20. Some preferred embodiments of anti-VEGF antibodies with reduced immunogenicity as compared to bevacizumab or ranibizumab are provided in FIG. 23.

6.6 Antibody Conjugates

The anti-VEGF antibodies of the disclosure include antibody conjugates that are modified, e.g., by the covalent attachment of any type of molecule to the antibody, such that covalent attachment does not interfere with binding to VEGF.

In certain aspects, an anti-VEGF antibody of the disclosure can be conjugated to an effector moiety or a label. The term "effector moiety" as used herein includes, for example, antineoplastic agents, drugs, toxins, biologically active proteins, for example enzymes, other antibody or antibody fragments, synthetic or naturally occurring polymers, nucleic acids (e.g., DNA and RNA), radionuclides, particularly radioiodide, radioisotopes, chelated metals, nanoparticles and reporter groups such as fluorescent compounds or compounds which can be detected by NMR or ESR spectroscopy.

In one example, anti-VEGF antibodies can be conjugated to an effector moiety, such as a cytotoxic agent, a radionuclide or drug moiety to modify a given biological response. The effector moiety can be a protein or polypeptide, such as, for example and without limitation, a toxin (such as abrin, ricin A, *Pseudomonas* exotoxin, or *Diphtheria* toxin), a signaling molecule (such as α-interferon, β-interferon, nerve growth factor, platelet derived growth factor or tissue plasminogen activator), a thrombotic agent or an anti-angiogenic agent (e.g., angiostatin or endostatin) or a biological response modifier such as a cytokine or growth factor (e.g., interleukin-1 (IL-1), interleukin-2 (IL-2), interleukin-6 (IL-6), granulocyte macrophage colony stimulating factor (GM-CSF), granulocyte colony stimulating factor (G-CSF), or nerve growth factor (NGF)).

In another example the effector moieties can be cytotoxins or cytotoxic agents. Examples of cytotoxins and cytotoxic agents include taxol, cytochalasin B, gramicidin D, ethidium bromide, emetine, mitomycin, etoposide, tenoposide, vincristine, vinblastine, colchicin, doxorubicin, daunorabicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector moieties also include, but are not limited to, antimetabolites (e.g. methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C5 and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, anthramycin (AMC), calicheamicins or duocarmycins), and anti-mitotic agents (e.g., vincristine and vinblastine).

Other effector moieties can include radionuclides such as, but not limited to, $^{111}$In and $^{90}$Y, Lu$^{177}$, Bismuth$^{213}$, Californium$^{252}$, Iridium$^{192}$ and Tungsten$^{188}$/Rhenium$^{188}$ and drugs such as, but not limited to, alkylphosphocholines, topoisomerase I inhibitors, taxoids and suramin.

Techniques for conjugating such effector moieties to antibodies are well known in the art (see, e.g., Hellstrom et al., Controlled Drug Delivery, 2nd Ed., at pp. 623-53 (Robinson et al., eds., 1987)); Thorpe et al., 1982, Immunol. Rev. 62:119-58 and Dubowchik et al., 1999, Pharmacology and Therapeutics 83:67-123).

In one example, the anti-VEGF antibody or fragment thereof is fused via a covalent bond (e.g., a peptide bond), through the antibody's N-terminus or C-terminus or internally, to an amino acid sequence of another protein (or portion thereof; for example at least a 10, 20 or 50 amino acid portion of the protein). The antibody, or fragment thereof, can linked to the other protein at the N-terminus of the constant domain of the antibody. Recombinant DNA procedures can be used to create such fusions, for example as described in WO 86/01533 and EP0392745. In another example the effector molecule can increase half-life in vivo, and/or enhance the delivery of an antibody across an epithelial barrier to the immune system. Examples of suitable effector molecules of this type include polymers, albumin, albumin binding proteins or albumin binding compounds such as those described in WO 2005/117984.

In certain aspects, an anti-VEGF antibody is conjugated to a small molecule toxin. In certain exemplary embodiments, an anti-VEGF antibody of the disclosure is conjugated to a dolastatin or a dolostatin peptidic analogs or derivatives, e.g., an auristatin (U.S. Pat. Nos. 5,635,483 and 5,780,588). The dolastatin or auristatin drug moiety may be attached to the antibody through its N (amino) terminus, C (carboxyl) terminus or internally (WO 02/088172). Exemplary auristatin embodiments include the N-terminus linked monomethylauristatin drug moieties DE and DF, as disclosed in U.S. Pat. No. 7,498,298, which is hereby incorporated by reference in its entirety (disclosing, e.g., linkers and methods of preparing monomethylvaline compounds such as MMAE and MMAF conjugated to linkers).

In other exemplary embodiments, small molecule toxins include but are not limited to calicheamicin, maytansine (U.S. Pat. No. 5,208,020), trichothene, and CC1065. In one embodiment of the disclosure, the antibody is conjugated to one or more maytansine molecules (e.g., about 1 to about 10 maytansine molecules per antibody molecule). Maytansine may, for example, be converted to May-SS-Me which may be reduced to May-SH3 and reacted with an antibody (Chari et al., 1992, Cancer Research 52: 127-131) to generate a maytansinoid-antibody or maytansinoid-Fc fusion conjugate. Structural analogues of calicheamicin that can also be used include but are not limited to $\gamma_1^1$, $\gamma_3^1$, N-acetyl-$\gamma_1^1$, PSAG, and $\theta_1^1$, (Hinman et al., 1993, Cancer Research 53:3336-3342; Lode et al., 1998, Cancer Research 58:2925-2928; U.S. Pat. No. 5,714,586; U.S. Pat. No. 5,712,374; U.S. Pat. No. 5,264,586; U.S. Pat. No. 5,773,001).

Antibodies of the disclosure can also be conjugated to liposomes for targeted delivery (See, e.g., Park et al., 1997, Adv. Pharmacol. 40:399-435; Marty & Schwendener, 2004, Methods in Molecular Medicine 109:389-401).

In one example antibodies of the present disclosure can be attached to poly(ethyleneglycol) (PEG) moieties. In one particular example the antibody is an antibody fragment and the PEG moieties can be attached through any available amino acid side-chain or terminal amino acid functional group located in the antibody fragment, for example any free amino, imino, thiol, hydroxyl or carboxyl group. Such amino acids can occur naturally in the antibody fragment or can be engineered into the fragment using recombinant DNA methods. See for example U.S. Pat. No. 5,219,996. Multiple sites can be used to attach two or more PEG molecules. PEG moieties can be covalently linked through a thiol group of at least one cysteine residue located in the antibody fragment. Where a thiol group is used as the point of attachment, appropriately activated effector moieties, for example thiol selective derivatives such as maleimides and cysteine derivatives, can be used.

In a specific example, an anti-VEGF antibody conjugate is a modified Fab' fragment which is PEGylated, i.e., has PEG (poly(ethyleneglycol)) covalently attached thereto, e.g., according to the method disclosed in EP0948544. See also Poly(ethyleneglycol) Chemistry, Biotechnical and Biomedical Applications, (J. Milton Harris (ed.), Plenum Press, New York, 1992); Poly(ethyleneglycol) Chemistry and Biological Applications, (J. Milton Harris and S. Zalipsky, eds., American Chemical Society, Washington D.C., 1997); and Bioconjugation Protein Coupling Techniques for the Biomedical Sciences, (M. Aslam and A. Dent, eds., Grove Publishers, New York, 1998); and Chapman, 2002, Advanced Drug Delivery Reviews 54:531-545. PEG can be attached to a cysteine in the hinge region. In one example, a PEG-modified Fab' fragment has a maleimide group covalently linked to a single thiol group in a modified hinge region. A lysine residue can be covalently linked to the maleimide group and to each of the amine groups on the lysine residue can be attached a methoxypoly(ethyleneglycol) polymer having a molecular weight of approximately 20,000 Da. The total molecular weight of the PEG attached to the Fab' fragment can therefore be approximately 40,000 Da.

The word "label" when used herein refers to a detectable compound or composition which can be conjugated directly or indirectly to an anti-VEGF antibody of the disclosure. The label can itself be detectable (e.g., radioisotope labels or fluorescent labels) or, in the case of an enzymatic label, can catalyze chemical alteration of a substrate compound or composition which is detectable. Useful fluorescent moieties include, but are not limited to, fluorescein, fluorescein isothiocyanate, rhodamine, 5-dimethylamine-1-napthalenesulfonyl chloride, phycoerythrin and the like. Useful enzymatic labels include, but are not limited to, alkaline phosphatase, horseradish peroxidase, glucose oxidase and the like.

Additional anti-VEGF antibody conjugates that are useful for, inter alia, diagnostic purposes, are described in Section 6.7 below.

6.7 Diagnostic Uses of Anti-VEGF Antibodies

The anti-VEGF antibodies of the disclosure, including those antibodies that have been modified, e.g., by biotinylation, horseradish peroxidase, or any other detectable moiety (including those described in Section 6.6), can be advantageously used for diagnostic purposes.

In particular, the anti-VEGF antibodies can be used, for example, but not limited to, to purify or detect VEGF, including both in vitro and in vivo diagnostic methods. For example, the antibodies have use in immunoassays for qualitatively and quantitatively measuring levels of VEGF in biological samples. See, e.g., Harlow et al., Antibodies: A Laboratory Manual, Second Edition (Cold Spring Harbor Laboratory Press, 1988), which is incorporated by reference herein in its entirety.

The present disclosure further encompasses antibodies or fragments thereof conjugated to a diagnostic agent. The antibodies can be used diagnostically, for example, to detect expression of a target of interest in specific cells, tissues, or serum; or to monitor the development or progression of an immunologic response as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the antibody (or fragment thereof) or indirectly, through an intermediate (such as, for example, a linker known in the art) using techniques known in the art. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, acetylcholinesterase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{111}In$ or $^{99}Tc$.

The disclosure provides for the detection of expression of VEGF, comprising contacting a biological sample (cells, tissue, or body fluid of an individual) using one or more anti-VEGF antibodies of the disclosure (optionally conjugated to detectable moiety), and detecting whether or not the sample is positive for VEGF expression, or whether the sample has altered (e.g., reduced or increased) expression as compared to a control sample.

Diseases that can be diagnosed using the present methods include, but are not limited to, the diseases described herein. In certain embodiments, the tissue or body fluid is peripheral blood, peripheral blood leukocytes, biopsy tissues such as lung or skin biopsies, and tissue.

6.8 Therapeutic Methods Using Anti-VEGF Antibodies

6.8.1 Clinical Benefits

The anti-VEGF antibodies of the disclosure can be used to treat various neoplasms or non-neoplastic conditions characterized by pathological angiogenesis.

The antibodies of the disclosure are useful in the treatment of tumors in which angiogenesis plays an important role in tumor growth, including cancers and benign tumors. Examples of cancer to be treated herein include, but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. More particularly, cancers that are amenable to treatment by the antibodies of the disclosure include breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, melanoma, ovarian cancer, mesothelioma, and multiple myeloma. In some embodiments, the anti-VEGF antibodies of the disclosure are used to treat colorectal cancer in a human patient.

The present disclosure encompasses anti-angiogenic therapy, a cancer treatment strategy aimed at inhibiting the development of tumor blood vessels required for providing nutrients to support tumor growth. Because angiogenesis is involved in both primary tumor growth and metastasis, the antiangiogenic treatment provided by the disclosure is capable of inhibiting the neoplastic growth of tumor at the primary site as well as preventing metastasis of tumors at the secondary sites.

Non-neoplastic conditions that are amenable to treatment with the antibodies of the disclosure include retinal diseases (e.g., age-related macular degeneration) and immune and inflammatory diseases (e.g., rheumatoid arthritis, psoriasis, atherosclerosis, diabetic and other proliferative retinopathies including retinopathy of prematurity, retrolental fibroplasia, neovascular glaucoma, age-related macular degeneration, thyroid hyperplasias (including Grave's disease), corneal and other tissue transplantation, chronic inflammation, lung inflammation, nephrotic syndrome, preeclampsia, ascites, pericardial effusion (such as that associated with pericarditis), and pleural effusion).

Accordingly, the present disclosure provides methods of treating any of the foregoing diseases in a patient in need thereof, comprising: administering to the patient an anti-VEGF antibody of the disclosure. Optionally, said administration is repeated, e.g., after one day, two days, three days, five days, one week, two weeks, three weeks, one month, five weeks, six weeks, seven weeks, eight weeks, two months or three months. The repeated administration can be at the same dose or at a different dose. The administration can be repeated once, twice, three times, four times, five times, six times, seven times, eight times, nine times, ten times, or more. For example, according to certain dosage regimens a patient receives anti-VEGF therapy for a prolonged period of time, e.g., 6 months, 1 year or more. The amount of anti-VEGF antibody administered to the patient is in certain embodiments a therapeutically effective amount. As used herein, a "therapeutically effective" amount of VEGF antibody can be administered as a single dose or over the course of a therapeutic regimen, e.g., over the course of a week, two weeks, three weeks, one month, three months, six months, one year, or longer. Exemplary therapeutic regimens are described in Section 6.11 below.

According to the present disclosure, treatment of a disease encompasses the treatment of patients already diagnosed as having any form of the disease at any clinical stage or manifestation; the delay of the onset or evolution or aggravation or deterioration of the symptoms or signs of the disease; and/or preventing and/or reducing the severity of the disease.

A "subject" or "patient" to whom the anti-VEGF antibody of the disclosure is administered is preferably a mammal such as a non-primate (e.g., cow, pig, horse, cat, dog, rat, etc.) or a primate (e.g., monkey or human). In certain embodiments, the subject or patient is a human. In certain aspects, the human is a pediatric patient. In other aspects, the human is an adult patient.

6.9 Pharmaceutical Compositions and Routes of Administration

Compositions comprising an anti-VEGF antibody of the disclosure and, optionally one or more additional therapeutic agents, such as the combination therapeutic agents described in Section 6.10 below, are provided herein. The compositions will usually be supplied as part of a sterile, pharmaceutical composition that will normally include a pharmaceutically acceptable carrier. This composition can be in any suitable form (depending upon the desired method of administering it to a patient).

The anti-VEGF antibodies of the disclosure can be administered to a patient by a variety of routes such as orally, transdermally, subcutaneously, intranasally, intravenously, intramuscularly, intraocularly, topically, intrathecally and intracerebroventricularly. The most suitable route for administration in any given case will depend on the particular antibody, the subject, and the nature and severity of the disease and the physical condition of the subject.

For treatment of indications other than retinal diseases, the effective dose of an anti-VEGF antibody of the disclosure can range from about 0.1 to about 75 mg/kg per single (e.g., bolus) administration, multiple administrations or continuous administration, or to achieve a serum concentration of 0.01-5000 µg/mL serum concentration per single (e.g., bolus) administration, multiple administrations or continuous administration, or any effective range or value therein depending on the condition being treated, the route of administration and the age, weight and condition of the subject. In certain embodiments, e.g. for the treatment of cancer, each dose can range from about 0.1 mg to about 50 mg per kilogram of body weight, for example from about 3 mg to about 25 mg per kilogram body weight. The antibody can be formulated as an aqueous solution and administered by subcutaneous injection.

For treatment of retinal diseases (e.g., age-related macular degeneration (AMD), the dosage suitably results in aqueous humor concentration of the anti-VEGF antibody the injected eye of 1-50 µg/mL. For treatment of AMD, each dose can be from 0.1 mg to about 1 mg, for example from about 0.25 to about 0.5 mg. The antibody can be formulated as an aqueous solution and administered by intravitreal injection.

Pharmaceutical compositions can be conveniently presented in unit dose forms containing a predetermined amount of an anti-VEGF antibody of the disclosure per dose. Such a unit can contain for example but without limitation 0.1 mg to 5 g, for example 1 mg to 1 g, or 10 to 50 mg. Pharmaceutically acceptable carriers for use in the disclosure can take a wide variety of forms depending, e.g., on the condition to be treated or route of administration.

Therapeutic formulations of the anti-VEGF antibodies of the disclosure can be prepared for storage as lyophilized formulations or aqueous solutions by mixing the antibody having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed.

Buffering agents help to maintain the pH in the range which approximates physiological conditions. They can be present at concentration ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium gly-uconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Non-ionic surfactants can be present in a range of about 0.05 mg/mL to about 1.0 mg/mL, for example about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), and cosolvents.

The formulation herein can also contain a combination therapeutic agent in addition to the anti-VEGF antibody of the disclosure. Examples of suitable combination therapeutic agents are provided in Section 6.10 below.

The dosing schedule for subcutaneous administration can vary from once every six months to daily depending on a number of clinical factors, including the type of disease, severity of disease, and the patient's sensitivity to the anti-VEGF antibody.

The dosage of an anti-VEGF antibody of the disclosure to be administered of will vary according to the particular antibody, the type of disease (e.g., cancer, inflammatory, etc.), the subject, and the severity of the disease, the physical condition of the subject, the therapeutic regimen (e.g., whether a combination therapeutic agent is used), and the selected route of administration; the appropriate dosage can be readily determined by a person skilled in the art.

It will be recognized by one of skill in the art that the optimal quantity and spacing of individual dosages of an anti-VEGF antibody of the disclosure will be determined by the nature and extent of the condition being treated, the form, route and site of administration, and the age and condition of the particular subject being treated, and that a physician will ultimately determine appropriate dosages to be used. This dosage can be repeated as often as appropriate. If side effects develop the amount and/or frequency of the dosage can be altered or reduced, in accordance with normal clinical practice.

6.10 Combination Therapy

Described below are combinatorial methods in which the anti-VEGF antibodies of the disclosure can be utilized. The combinatorial methods of the disclosure involve the administration of at least two agents to a patient, the first of which is an anti-VEGF antibody of the disclosure, and the second of which is a combination therapeutic agent. The anti-VEGF antibody and the combination therapeutic agent can be administered simultaneously, sequentially or separately.

The combinatorial therapy methods of the present disclosure can result in a greater than additive effect, providing therapeutic benefits where neither the anti-VEGF antibody or combination therapeutic agent administered in an amount that is alone therapeutically effective.

In the present methods, the anti-VEGF antibody of the disclosure and the combination therapeutic agent can be administered concurrently, either simultaneously or successively. As used herein, the anti-VEGF antibody of the disclosure and the combination therapeutic agent are said to be administered successively if they are administered to the patient on the same day, for example during the same patient visit. Successive administration can occur 1, 2, 3, 4, 5, 6, 7 or 8 hours apart. In contrast, the anti-VEGF antibody of the disclosure and the combination therapeutic agent are said to be administered separately if they are administered to the patient on the different days, for example, the anti-VEGF antibody of the disclosure and the combination therapeutic agent can be administered at a 1-day, 2-day or 3-day, one-week, 2-week or monthly intervals. In the methods of the present disclosure, administration of the anti-VEGF antibody of the disclosure can precede or follow administration of the combination therapeutic agent.

As a non-limiting example, the anti-VEGF antibody of the disclosure and combination therapeutic agent can be administered concurrently for a period of time, followed by a second period of time in which the administration of the anti-VEGF antibody of the disclosure and the combination therapeutic agent is alternated.

Because of the potentially synergistic effects of administering an anti-VEGF antibody of the disclosure and a combination therapeutic agent, such agents can be administered in amounts that, if one or both of the agents is administered alone, is/are not therapeutically effective.

In certain aspects, the combination therapeutic agent is an anti-angiogenic agent, an anti-rheumatic drug, an anti-inflammatory agent, a chemotherapeutic agent, a radiotherapeutic, an immunosuppressive agent, or a cytotoxic drug.

It is contemplated that when used to treat various diseases, the anti-VEGF antibodies of the disclosure can be combined with other therapeutic agents suitable for the same or similar diseases. When used for treating cancer, antibodies of the present disclosure may be used in combination with conventional cancer therapies, such as surgery, radiotherapy, chemotherapy or combinations thereof.

In some other aspects, other therapeutic agents useful for combination tumor therapy with the antibody of the disclosure include antagonists, e.g., antibodies, of other factors that are involved in tumor growth, such as EGFR, ErbB2 (also known as Her2), ErbB3, ErbB4, or TNF-α.

Sometimes, for treatment of cancers and immune diseases, it may be beneficial to also administer one or more cytokines to the patient. In a preferred embodiment, the VEGF antibody is co-administered with a growth inhibitory agent.

Suitable dosages for the growth inhibitory agent are those presently used and may be lowered due to the combined action (synergy) of the growth inhibitory agent and anti-VEGF antibody.

For treatment of cancers, immune diseases and retinal diseases, anti-inflammatory agents can suitably be used in combination with the anti-VEGF antibodies of the disclosure. Anti-inflammatory agents include, but are not limited to, acetaminophen, diphenhydramine, meperidine, dexamethasone, pentasa, mesalazine, asacol, codeine phosphate, benorylate, fenbufen, naprosyn, diclofenac, etodolac and indomethacin, aspirin and ibuprofen.

For treatment of cancers, chemotherapeutic agents can suitably be used in combination with the anti-VEGF antibodies of the disclosure. Chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, an anti-α5β1 integrin antibody, alkylating agents, allopurinol sodium, altretamine, amifostine, anastrozole, anthramycin (AMC)), anti-mitotic agents, cis-dichlorodiamine platinum (II) (DDP) cisplatin, diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, $E.\ coli$ L-asparaginase, eolociximab, emetine, epoetin-α, Erwinia L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Any anti-angiogenic agent can be used in conjunction with the anti-VEGF antibodies of the disclosure, including those listed by Carmeliet and Jain, 2000, Nature 407:249-257. In certain embodiments, the anti-angiogenic agent is another VEGF antagonist or a VEGF receptor antagonist such as VEGF variants, soluble VEGF receptor fragments, aptamers capable of blocking VEGF or VEGFR, neutralizing anti-VEGFR antibodies, low molecule weight inhibitors of VEGFR tyrosine kinases and any combinations thereof. Alternatively, or in addition, two or more anti-VEGF antibodies may be co-administered to the patient.

In certain embodiments, hormone therapy can be used in conjunction with anti-VEGF antibodies of the disclosure. In some embodiments, the hormone therapy includes one or more agents that inhibit estrogen and/or progesterone from promoting cancer cell growth, e.g., a selective estrogen-receptor modulator such as tamoxifen, an aromatase inhibitor such as anastrozole (Arimidex®) or letrozole (Femara), an aromatase inactivator such as exemestane (Aromasin®), or an agent that inhibits estrogen production such as goserelin (Zoladex). In other embodiments, the hormone therapy is one or more agents that inhibit production of hormones from the ovaries.

In some aspects, an anti-VEGF antibody can be used in conjunction with a small molecule protein tyrosine kinase (PTK) inhibitor. In some embodiments, the PTK inhibitor is specific for a VEGF receptor tyrosine kinase. In other embodiments, the PTK inhibitor binds to more than one of the VEGF receptor family of tyrosine kinases (e.g., VEGFR-1, VEGFR-2). In other embodiments, protein tyrosine kinase inhibitors useful in the compositions and methods of the invention include PTK inhibitors that do not bind selectively to the VEGF family of receptor tyrosine kinases, but also bind to the tyrosine kinase domains of other families of proteins such as HER2, HER3, HER4, PDGFR, and/or Raf.

In some embodiments, the tyrosine kinase is a receptor tyrosine kinase, i.e., is an intra-cellular domain of a larger protein that has an extra-cellular ligand binding domain and is activated by the binding of one or more ligands. In certain embodiments, the protein tyrosine kinase is a non-receptor tyrosine kinase. PTK inhibitors for use in the methods of the present disclosure include, but are not limited to, gefitinib (ZD-1839, Iressa®), erlotinib (OSI-1774, Tarceva™), canertinib (CI-1033), vandetanib (ZD6474, Zactima®), tyrphostin AG-825 (CAS 149092-50-2), lapatinib (GW-572016), sorafenib (BAY43-9006), AG-494 (CAS 133550-35-3), RG-13022 (CAS 149286-90-8), RG-14620 (CAS 136831-49-7), BIBW 2992 (Tovok), tyrphostin 9 (CAS 136831-49-7), tyrphostin 23 (CAS 118409-57-7), tyrphostin 25 (CAS 118409-58-8), tyrphostin 46 (CAS 122520-85-8), tyrphostin 47 (CAS 122520-86-9), tyrphostin 53 (CAS 122520-90-5), butein (1-(2,4-dihydroxyphenyl)-3-(3,4-dihydroxyphenyl)-2-propen-1-one 2',3,4,4'-Tetrahydroxychalcone; CAS 487-52-5), curcumin ((E,E)-1,7-bis(4-Hydroxy-3-methoxyphenyl)-1,6-heptadiene-3,5-dione; CAS 458-37-7), N4-(1-Benzyl-1H-indazol-5-yl)-N6,N6-dimethyl-pyrido-[3,4-d]-pyrimidine-4,6-diamine (202272-68-2), AG-1478, AG-879, Cyclopropanecarboxylic acid-(3-(6-(3-trifluoromethyl-phenylamino)-pyrimidin-4-ylamino)-phenyl)-amide (CAS 879127-07-8), N8-(3-Chloro-4-fluorophenyl)-N2-(1-methylpiperidin-4-yl)-pyrimido[5,4-d]pyrimidine-2,8-diamine, 2HCl (CAS 196612-93-8), 4-(4-Benzyloxyanilino)-6,7-dimethoxyquinazoline (CAS 179248-61-4), N-(4-((3-Chloro-4-fluorophenyl)amino)pyrido[3,4-d]pyrimidin-6-yl)-2-butynamide (CAS 881001-19-0), EKB-569, HKI-272, and HKI-357.

In a specific embodiment, an anti-VEGF antibody of the disclosure is used in combination with intravenous 5-fluorouracil-based chemotherapy. This combination is suitable for, inter alia, first- or second-line treatment of patients with metastatic carcinoma of the colon or rectum.

In another specific embodiment, an anti-VEGF antibody of the disclosure is used in combination with carboplatin and paclitaxel. This combination is suitable for, inter alia, first-line treatment of patients with unresectable, locally advanced, recurrent or metastatic non-squamous, non-small cell lung cancer.

In yet another specific embodiment, an anti-VEGF antibody of the disclosure is used in combination with paclitaxel. This combination is suitable for, inter alia, treatment of patients who have not received chemotherapy for metastatic HER2-negative breast cancer.

For treatment of retinal diseases, the anti-VEGF antibodies of the disclosure can be used in combination with E10030, an anti-platelet-derived growth factor (PDGF) pegylated aptamer; with ARC1905, a pegylated aptamer targeting the C5 component of the complement cascade; and volociximab, a monoclonal antibody targeting the α5β1 integrin transmembrane receptor; photodynamic therapy with Visudyne® (PDT); or Macugen®, an aptamer (pegaptanib sodium).

6.11 Therapeutic Regimens

The present disclosure provides therapeutic regimens involving the administration of the anti-VEGF antibodies of the disclosure. The therapeutic regimen will vary depending on the patient's age, weight, and disease condition. The therapeutic regimen can continue for 2 weeks to indefinitely. In specific embodiments, the therapeutic regimen is continued for 2 weeks to 6 months, from 3 months to 5 years, from 6 months to 1 or 2 years, from 8 months to 18 months, or the like. The therapeutic regimen can be a non-variable dose regimen or a multiple-variable dose regimen.

For the dosage exemplary regimens described below, the anti-VEGF antibody can be administered as a sterile, preservative-free solution for subcutaneous administration.

For treatment of metastatic colorectal cancer, an anti-VEGF antibody of the disclosure is administered intravenously at a dose of 0.5-15 mg/kg every 2 weeks with bolus-IFL (irinotecan, 5-fluorouracil and leucovorin regimen). In specific embodiments, the dose is 1-4 mg/kg, 2-6 mg/kg, 0.5-3 mg/kg, 1-10 mg/kg, 3-4.8 mg/kg or 1-4.5 mg/kg every two weeks with bolus-IFL.

In another embodiment for treatment of metastatic colorectal cancer, an anti-VEGF antibody of the disclosure is administered intravenously at a dose of 1-30 mg/kg every 2 weeks with FOLFOX4 (oxaliplatin, leucovorin, and fluorouracil regimen). In specific embodiments, the dose is 2-9 mg/kg, 3-12 mg/kg, 1-7.5 mg/kg, 2-20 mg/kg, 6-9.75 mg/kg or 4-9.5 mg/kg every two weeks with FOLFOX4.

For treatment of non-squamous non-small cell lung cancer, an anti-VEGF antibody of the disclosure is administered intravenously at a dose of 2-40 mg/kg every three weeks with carboplatin/paclitaxel. In specific embodiments, the dose is 5-14 mg/kg, 4-20 mg/kg, 10-17.5 mg/kg, 7-14 mg/kg, 10-30 mg/kg or 3-30 mg/kg every three weeks with carboplatin/paclitaxel.

For treatment of metastatic breast cancer, an anti-VEGF antibody of the disclosure is administered intravenously at a dose of 0.5-20 mg/kg every two weeks with paclitaxel. In specific embodiments, the dose is 1-4 mg/kg, 2-6 mg/kg, 0.5-3 mg/kg, 1-10 mg/kg, 3-4.8 mg/kg or 1-4.5 mg/kg every two weeks with paclitaxel.

For treatment of metastatic breast cancer, an anti-VEGF antibody of the disclosure is administered intravenously at a dose of 0.5-20 mg/kg every two weeks as monotherapy. In specific embodiments, the dose is 1-4 mg/kg, 2-6 mg/kg, 0.5-3 mg/kg, 1-10 mg/kg, 3-4.8 mg/kg or 1-4.5 mg/kg every two weeks as monotherapy.

For treatment of age-related macular degeneration (AMD), an anti-VEGF antibody of the disclosure is administered at a dose of 0.1-1 mg by intravitreal injection once a month (approximately 28 days). In specific embodiments, the dose is 0.1-0.4 mg, 0.2-0.6 mg, 0.1-0.25 mg, 0.25-0.5 mg, 0.25-0.75 mg, or 0.3-0.45 mg by intravitreal injection once a month (approximately 28 days). In a specific embodiment, a patient treated with an anti-VEGF antibody of the disclosure has wet AMD. In another specific embodiment, a patient has dry AMD.

6.12 Diagnostic and Pharmaceutical Kits

Encompassed by the present disclosure are pharmaceutical kits containing the anti-VEGF antibodies (including antibody conjugates) of the disclosure. The pharmaceutical kit is a package comprising the anti-VEGF antibody of the disclosure (e.g., either in lyophilized form or as an aqueous solution) and one or more of the following:

A combination therapeutic agent, for example as described in Section 6.10 above;
A device for administering the anti-VEGF antibody, for example a pen, needle and/or syringe; and
Pharmaceutical grade water or buffer to resuspend the antibody if the antibody is in lyophilized form.

In certain aspects, each unit dose of the anti-VEGF antibody is packaged separately, and a kit can contain one or more unit doses (e.g., two unit doses, three unit doses, four unit doses, five unit doses, eight unit doses, ten unit doses, or more). In a specific embodiment, the one or more unit doses are each housed in a syringe or pen.

Diagnostic kits containing the anti-VEGF antibodies (including antibody conjugates) of the disclosure are also encompassed herein. The diagnostic kit is a package comprising the anti-VEGF antibody of the disclosure (e.g., either in lyophilized form or as an aqueous solution) and one or more reagents useful for performing a diagnostic assay. Where the anti-VEGF antibody is labeled with an enzyme, the kit can include substrates and cofactors required by the enzyme (e.g., a substrate precursor which provides the detectable chromophore or fluorophore). In addition, other additives can be included, such as stabilizers, buffers (e.g., a block buffer or lysis buffer), and the like. In certain embodiments, the anti-VEGF antibody included in a diagnostic kit is immobilized on a solid surface, or a solid surface (e.g., a slide) on which the antibody can be immobilized is included in the kit. The relative amounts of the various reagents can be varied widely to provide for concentrations in solution of the reagents which substantially optimize the sensitivity of the assay. In a specific embodiment, the antibody and one or more reagents can be provided (individually or combined) as dry powders, usually lyophilized, including excipients which on dissolution will provide a reagent solution having the appropriate concentration.

7. EXAMPLE 1

Identification of T-Cell Epitopes of Bevacizumab

7.1 Materials & Methods
7.1.1 Peptides

Peptides were synthesized using a multi-pin format by Mimotopes (Adelaide, Australia). The sequences of the bevacizumab light and heavy chain V regions were synthesized as 15-mer peptides overlapping by 12 amino acids (FIGS. 7 and 8) for a total of 69 peptides. Peptides arrived lyophilized and were re-suspended in DMSO (Sigma-Aldrich) at approximately 1-2 mg/mL. Stock peptides were kept frozen at −20° C.

7.1.2 Human Peripheral Blood Mononuclear Cells

Community donor buffy coat products were purchased from the Stanford Blood Center, Palo Alto, Calif. Buffy coat material was diluted 1:1 v:v with DPBS containing no calcium or magnesium. Diluted buffy coat material (25-35 mls) was underlayed in 50 ml conical centrifuge tubes (Sarsted or Costar) with 12.5 mls of FicollPaque-PLUS (GE Healthcare). The samples were centrifuged at 900 g for 30 minutes at room temperature. Peripheral blood mononuclear cells (PBMC) were collected from the interface. DPBS was added to bring the final volume to 50 mls and the cells were centrifuged at 350 g for 5 minutes. Pelleted cells were resuspended in DPBS and counted.

7.1.3 Dendritic Cells

For isolation of dendritic cells, T75 culture flasks (Costar) were seeded with $10^8$ freshly isolated PBMC in a total volume of 30 mls AIM V media (Invitrogen). Excess PBMC were frozen at −80° C. in 90% fetal calf serum (FCS), 10% DMSO at $5 \times 10^7$ cells/mL. T75 flasks were incubated at 37° C. in 5% $CO_2$ for 2 hours. Nonadherent cells were removed, and the adherent monolayer was washed with DPBS. To differentiate dendritic cells from monocytes, 30 mls of AIM V media containing 800 units/mL of GM-CSF (R and D Systems) and 500 units/mL IL-4 (R and D Systems) was added. Flasks were incubated for 5 days. On day 5 IL-1α (Endogen) and TNFα (Endogen) were added to 50 pg/mL and 0.2 ng/mL. Flasks were incubated two more days. On day 7, dendritic cells were collected by the addition of 3 mls of 100 mM EDTA containing 0.5 to 1.0 mg Mitomycin C (Sigma-Aldrich) for a final concentration of 10 mM EDTA and 16.5 to 33 µg/mL Mitomycin C. Flasks were incubated an additional hour at 37° C. and 5% $CO_2$. Dendritic cells were collected, and washed in AIM V media 2-3 times.

7.1.4 Cell Culture

On day 7, previously frozen autologous PBMC were thawed quickly in a 37° C. water bath. Cells were immediately diluted into DPBS or AIM V media and centrifuged at 350 g for 5 minutes. $CD4^+$ cells were enriched by negative selection using magnetic beads (Easy-Sep $CD4^+$ kit, Stem Cell Technologies). Autologous $CD4^+$ T cells and dendritic cells were cocultured at $2 \times 10^5$ $CD4^+$ T cells per $2 \times 10^4$ dendritic cells per well in 96 well round bottomed plates (Costar 9077). Peptides were added at approximately 5 µg/mL. Control wells contained the DMSO (Sigma) vehicle alone at 0.25% v:v. Positive control wells contained DMSO at 0.25% and tetanus toxoid (List Biologicals or CalBioChem) at 1 µg/mL. Cultures were incubated for 5 days. On day 5, 0.25 µCi per well of tritiated thymidine (Amersham or GE Healthcare) was added. Cultures were harvested on day 6 to filtermats using a Packard Filtermate Cell harvester. Scintillation counting was performed using a Wallac MicroBeta 1450 scintillation counter (Perkin Elmer).

7.1.5 Data Analysis

Average background CPM values were calculated by averaging individual results from 6 to 12 replicates. The CPM values of the four positive control wells were averaged. Replicate or triplicate wells for each peptide were averaged. Stimulation index values for the positive control and the peptide wells were calculated by dividing the average experimental CPM values by the average control values. In order to be included in the dataset, a stimulation index of greater than 3.0 in the tetanus toxoid positive control wells was required. A response was noted for any peptide resulting in a stimulation index of 2.95 or greater. Peptides were tested using peripheral blood samples from a group of 99 donors. Responses to all peptides were compiled. For each peptide tested, the percentage of the donor set that responded with a stimulation index of 2.95 or greater was calculated. In addition, the average stimulation index for all donors was also calculated.

Figures 3A, 3B:
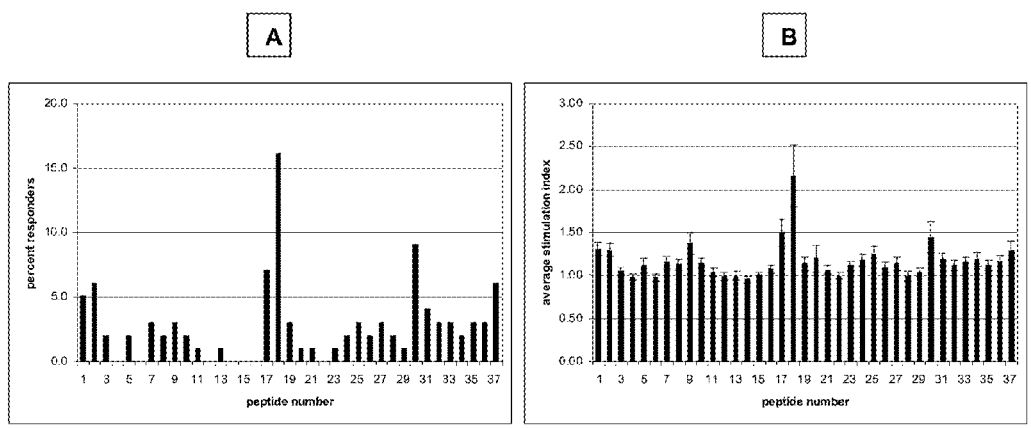

7.2 Results 7.2.1 Identification Of CD4+ T Cell Epitopes in the Bevacizumab VH And VL Regions $CD4^+$ T cell epitope peptides were identified by an analysis of the percent responses to the peptides within the set of 99 donors. The average percent response and standard deviation were calculated for all peptides tested describing the bevacizumab heavy chain and light chain V regions. A response rate greater than or equal to the average background response plus three standard deviations was considered a potential $CD4^+$ T cell epitope. For the bevacizumab light chain V region, 32 peptides were tested (FIG. 7) which resulted in an average background percent response of 2.1±2.7%. Three standard deviations above background was determined to be 10.2%. One peptide at position 13 (Q40-T54) displayed this level of response in the bevacizumab light chain peptide dataset, with a response rate of 15.2% (FIG. 2A). For the bevacizumab heavy chain V region, 37 peptides were tested (FIG. 8). The average background percent response was 2.8±3.1%. Three standard deviations above background was 12.1%. One peptide within the bevacizumab heavy chain dataset, #18 (N52-R56), achieved a percent response of 16.2% (FIG. 3A). A second peptide at position #30 in the heavy chain dataset achieved a response rate of 9.1%, and was considered an epitope due to an increased stimulation index (see below).

The average stimulation index was calculated for all peptides in the dataset. Light chain peptide 13 had a high average stimulation index of 1.82±0.24 s.e.m. (FIG. 2B). Heavy chain peptide #18 had an average stimulation index value of 2.16±0.35 s.e.m. (FIG. 3B). The peptide at position #30 returned an average stimulation index of 1.45+0.18 s.e.m. (FIG. 3B) due to an elevated average stimulation index and an above average response rate. The peptide at position #30 was included when determining $CD4^+$ T cell epitope content of this antibody V region. All of these stimulation index values are significantly higher than the average stimulation index for all peptides in the two datasets (1.14±0.07 for all 69 heavy chain and light chain peptides).

These data indicate that there are three CD4+ T cell epitope regions in the bevacizumab V regions (FIG. 9). In the VL region, an epitope is found at peptide position 13 that encompasses framework 2 and two amino acids from CDR2. The sequence contains a murine back-mutation (V46) inserted into the sequence during humanization. In FIG. 9, the CDR-derived amino acids are underlined. In the heavy chain, two epitope peptide regions were identified. The stronger epitope at position #18 encompasses all of CDR2. The second epitope peptide region contains both framework 3 and CDR3 amino acids.

7.2.2 Reduced Immunogenicity Variants of Bevacizumab Variant Antibodies

Bevacizumab was subjected to mutational analysis (see Example 2 below). Based on antigen-binding studies performed in conjunction with the mutational analysis, a set of candidate amino acid substitutions within the CDR-H2 and CDR-H3 region were identified that did not significantly reduce the affinity of the antibody to VEGF (FIG. 10). These amino acid substitutions were tested singly and in combination to identify variants of bevacizumab with reduced immunogenicity as compared to the wild type antibody.

8. EXAMPLE 2

Identification of Variants of Bevacizumab with Increased Affinity to VEGF

The bevacizumab antibody was subjected to comprehensive mutational analysis to identify mutants that had increased affinity to VEGF as compared to bevacizumab. The increased affinity of candidate high affinity mutants to VEGF as compared to bevacizumab was analyzed by BIAcore to confirm their binding characteristics.

8.1 Materials & Methods 8.1.1 BIAcore

Fifteen variant bevacizumab VH region constructs were cloned along with the unmodified VL region into a human IgG$_1$-containing plasmid, expressed in 293T/17 cell lines by transient transfection, and antibodies purified by Protein A or Protein G affinity. The affinity of the antibodies for VEGF (R&D systems, Minneapolis, Minn.) was determined by using a BIAcore 2000 and 3000 surface plasmon resonance system (BIAcore, GE Healthcare, Piscataway, N.J.). Polyclonal goat anti-human Fc antibody (Jackson Immunoresearch) was first immobilized to the biosensor surface using standard BIAcore amine coupling reagents (N-ethyl-N'-dimethylamino-propylcarbodiimide, EDC; N-hydroxysuccinimide, NHS; and ethanolamine HCl, pH 8.5), followed by the capture of anti-VEGF antibodies (bevacizumab and bevacizumab variants) on parallel surfaces at a low flow rate of 5 μL/min. RL was kept low to minimize avidity due to the dimeric nature of VEGF. No capture of the antibody was made on the reference surface to serve as a negative control. Subsequently, VEGF was injected to all flow cells at a flow rate of 50 μL/min for two minutes to monitor association followed by a 25-minute flow of HBS-P running buffer (10 mM HEPES, 150 mM sodium chloride, 0.005% P-20, pH 7.4) to monitor the dissociation phase. At each cycle, VEGF, in 6 different concentrations of VEGF ranging between 0 nM and 512 nM and at four-fold increments, was injected over the surface. The surface was regenerated with 1.5% $H_3PO_4$ at a flow rate of 100 μL/min in two brief pulses at the end of each cycle. Binding data were fit to the 1:1 Langmuir model to extract binding constants from the BIAevaluate software. Double referencing was applied in each analysis to eliminate background responses from the reference surface and buffer only control. All the binding kinetics data were analyzed at least three separate determinations.

8.2 Results

Results are displayed as absolute numbers and as fold improvement over wild-type. Almost all the variants listed have improved association ($k_{on}$) and dissociation ($k_{off}$) rates when compared to bevacizumab or wild-type (FIG. 11). The final affinity values for the variants were in the 0.1 nM range and reach as low as 0.08 nM for the variant corresponding to SEQ ID NO:82. These values contrast to bevacizumab which has a measured affinity in these experiments of 1.9 nM.

FIGS. 12 and 13 show additional heavy chain variants that preliminary binding studies show have a greater affinity to VEGF than bevacizumab (data not shown). FIG. 14 shows heavy chain variants that preliminary studies indicate have an affinity to VEGF similar to that of bevacizumab (data not shown). FIG. 15 shows light chain variants that that preliminary studies indicate have an affinity to VEGF similar to that of bevacizumab (data not shown).

9. EXAMPLE 3

Selection of Deimmunized Variant Peptides

Variant peptides corresponding to the immunogenic regions of bevacizumab (see Example 1) were generated (FIGS. 18-20). The variant peptides were selected on the basis of comprehensive mutational analysis described in Example 2, in which CDR modifications were identified that did not substantially reduce the binding affinity of bevacizumab to VEGF.

Figure 4A:
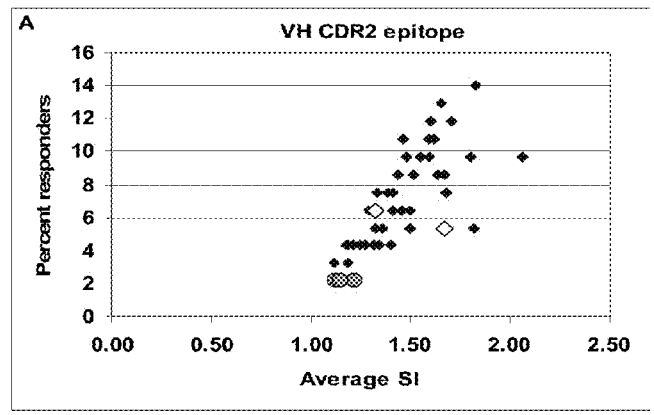
Figure 4B:
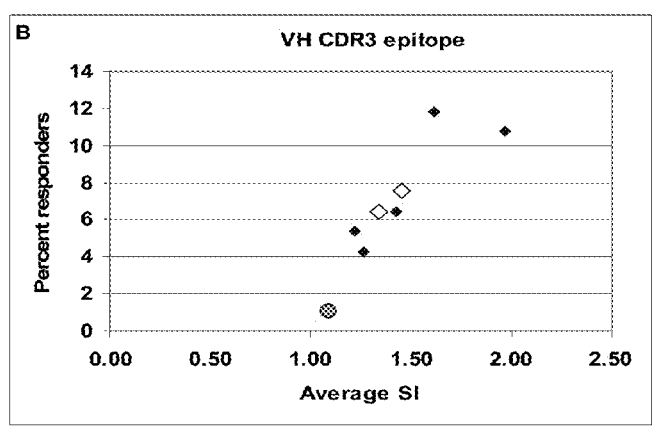
Figure 4C:
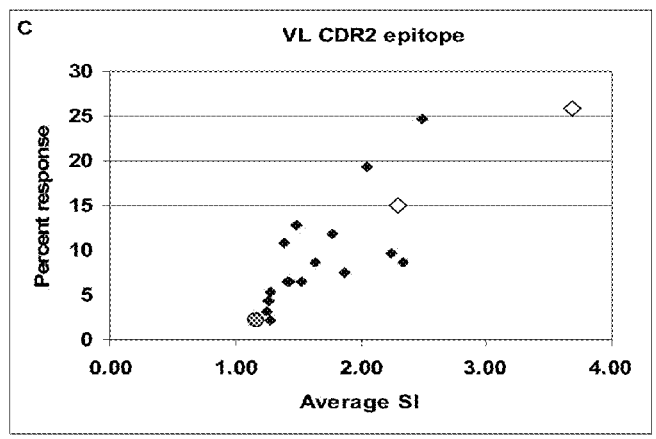

A total of 77 peptides were synthesized and tested based on the antigen-binding studies, including two syntheses of each of the parent 15-mer peptides. A total of 93 donors were tested with the parent and variant peptides utilizing the method described in Section 7.1 and the results are shown in FIGS. 4A-4C. In particular, FIGS. 4A-4C show CD4+ T cell responses to mutant bevacizumab epitope peptides. Average responses to the unmodified parent epitope sequences are indicated with open marks. Large circles indicate selected peptides referred to in FIG. 21 (see below). FIG. 4A shows VH CDR2 peptides; FIG. 4B shows VH CDR3 peptides; and FIG. 4C shows VL CDR2 peptides. Immunogenicity data for selected peptides are shown in FIG. 21.

For the heavy chain variable region CDR2 peptides, the average percent response to the parent peptides in this study was 5.38% and 6.45%. Three mutant peptides demonstrated a reduced overall response rate and average stimulation index as compared to the parent peptides.

The parent peptide response rates for the heavy chain variable region CDR3 epitope peptides in this study were 7.53% and 6.45%. A single mutant peptide sequence was found that demonstrated reduced overall responses as compared to the parent peptide.

Finally, the light chain variable region CDR2 peptide parent response rates in this study were 25.8% and 15%. One mutant peptide was identified that demonstrated a reduced overall immunogenicity as compared to the parent peptide.

To demonstrate that the deimmunizing mutations maintained affinity to VEGF as compared to bevacizumab, flow cytometry was used to compare the binding properties of variant antibodies incorporating mutations in the modified epitope peptides (either as single or double amino-acid modifications and bevacizumab). Several deimmunizing mutations had comparable or increased affinity to VEGF as compared to bevacizumab.

In one study, transiently transfected 293c18 cells expressing surface-bound forms of the bevacizumab variants were stained with Alexa647-conjugated rHuVEGF (Invitrogen Cat #PHG0143) at 3 nM and goat-anti-human-kappa-RPE (Southern Biotech Cat#2063-09) at a 1:400 dilution. Data were gathered by way of flow cytometry using a DakoCytomation CyAn ADP flow cytometer and was analyzed using Treestar's FloJo analysis program. The mean fluorescence intensities (MFI) measured in this work are set forth in FIG. 22.

In another study, the $EC_{50}$ of bevacizumab and variant antibody binding to VEGF was measured. Antibody titration plots were generated using bevacizumab and its variants with Alexas647-conjugated rHu VEGF as described above, with the VEGF serially diluted two-fold from 5 μM to 0.01 μM. The $EC_{50}$ values are shown in FIG. 23.

10. SPECIFIC EMBODIMENTS, CITATION OF REFERENCES

All publications, patents, patent applications and other documents cited in this application are hereby incorporated by reference in their entireties for all purposes to the same extent as if each individual publication, patent, patent application or other document were individually indicated to be incorporated by reference for all purposes. While various specific embodiments have been illustrated and described, it will be appreciated that various changes can be made without departing from the spirit and scope of the invention(s).

What is claimed is:

1. A monoclonal antibody or a binding fragment thereof which:
   (a) specifically binds to human VEGF;
   (b) comprises a heavy chain amino acid sequence having at least 95% sequence identity to SEQ ID NO:1 and a light chain amino acid sequence having at least 95% sequence identity to SEQ ID NO:2; and
   (c) has at least one amino acid substitution or combination of amino acid substitutions selected from:
   (i) K64S in CDR-H2;
   (ii) H97E and Y98F in CDR-H3;
   (iii) N31F in CDR-H1, H97D in CDR-H3, Y99D in CDR-H3, and S100aG in CDR-H3;
   (iv) N31F in CDR-H1, H97P in CDR-H3, Y99D in CDR-H3, and S100aG in CDR-H3;
   (v) N31F in CDR-H1, H97P in CDR-H3, and Y99E in CDR-H3;
   (vi) N31F in CDR-H1, H97E in CDR-H3, and Y99E in CDR-H3;
   (vii) N31F in CDR-H1, H97D in CDR-H3, and Y99E in CDR-H3;
   (viii) N31F in CDR-H1, H97E in CDR-H3, Y99D in CDR-H3, and S100aG in CDR-H3;
   (ix) N31F in CDR-H1, Y99D in CDR-H3, and S100aG in CDR-H3;
   (x) N31F in CDR-H1, H97P in CDR-H3, and Y99D in CDR-H3;
   (xi) N31F in CDR-H1, H97D in CDR-H3, and S100aG in CDR-H3;
   (xii) N31F in CDR-H1 and S100aG in CDR-H3;
   (xiii) N31F in CDR-H1, H97P in CDR-H3, and S100aG in CDR-H3; and
   (xiv) N31F in CDR-H1;
   wherein the substitutions occur at positions corresponding to Kabat numbering in the heavy chain of SEQ ID NO: 1 wherein the antibody or binding fragment thereof reduced immunogenicity or increased affinity to VEGF as compared to bevacizumab or ranibizumab.

2. The monoclonal antibody or binding fragment of claim 1, wherein the heavy chain amino acid sequence has at least 98% sequence identity to SEQ ID NO:1 and the light chain amino acid sequence has at least 98% sequence identity to SEQ ID NO:2.

3. The monoclonal antibody or binding fragment of claim 1, wherein the heavy chain amino acid sequence has at least 99% sequence identity to SEQ ID NO:1 and the light chain amino acid sequence has at least 99% sequence identity to SEQ ID NO:2.

4. The monoclonal antibody or binding thereof fragment of claim 1, wherein said amino acid substitution includes the substitution K64S.

5. The monoclonal antibody or binding thereof fragment of claim 1, wherein said amino acid substitution includes the substitution N31F.

6. The monoclonal antibody or binding thereof fragment of claim 1, wherein said amino acid substitutions include the substitutions H97E and Y98F.

7. The monoclonal antibody or binding fragment thereof of claim 1, wherein the antibody or binding fragment thereof is human or humanized antibody.

8. The monoclonal antibody or binding fragment thereof of claim 1, wherein the antibody is an IgG.

9. The monoclonal antibody or binding fragment thereof of claim 1, wherein the antibody or binding fragment thereof has the heavy chain framework sequences of the $V_H$ sequence of SEQ ID NO:1 and the light chain framework sequences of the $V_L$ sequence of SEQ ID NO:2.

10. The monoclonal antibody or binding fragment thereof of claim 1, wherein the antibody or binding fragment thereof has the heavy chain framework sequences of the $V_H$ sequence of SEQ ID NO:9 and the light chain framework sequences of the $V_L$ sequence of SEQ ID NO:10.

11. An antibody-drug conjugate comprising the anti-VEGF antibody or anti-VEGF binding fragment according to claim 1.

* * * * *

UNITED STATES PATENT AND TRADEMARK OFFICE
CERTIFICATE OF CORRECTION

PATENT NO. : 9,079,953 B2
APPLICATION NO. : 12/817800
DATED : July 14, 2015
INVENTOR(S) : Fiona A. Harding et al.

It is certified that error appears in the above-identified patent and that said Letters Patent is hereby corrected as shown below:

IN THE CLAIMS

Column 204, claim 1, line 43, should read "thereof has reduced immunogenicity or increased affinity"

Column 204, claim 4, line 56, should read "The monoclonal antibody or binding fragment thereof of"

Column 204, claim 5, line 59, should read "The monoclonal antibody or binding fragment thereof of"

Column 204, claim 6, line 62, should read "The monoclonal antibody or binding fragment thereof of"

Signed and Sealed this
Twenty-fourth Day of November, 2015

Michelle K. Lee
*Director of the United States Patent and Trademark Office*